US012734239B2

(12) United States Patent
Ang et al.

(10) Patent No.: US 12,734,239 B2
(45) Date of Patent: Sep. 15, 2026

(54) K562 UNIVERSAL ANTIGEN PRESENTING CELLS AND USES THEREOF

(71) Applicant: Board of Regents, The University of Texas System, Austin, TX (US)

(72) Inventors: Sonny O. T. Ang, Houston, TX (US); Enli Liu, Houston, TX (US); Elizabeth Shpall, Houston, TX (US); Katy Rezvani, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1131 days.

(21) Appl. No.: 16/970,930

(22) PCT Filed: Feb. 21, 2019

(86) PCT No.: PCT/US2019/018989

§ 371 (c)(1),
(2) Date: Aug. 18, 2020

(87) PCT Pub. No.: WO2019/165097

PCT Pub. Date: Aug. 29, 2019

(65) Prior Publication Data

US 2020/0390815 A1 Dec. 17, 2020

Related U.S. Application Data

(60) Provisional application No. 62/633,587, filed on Feb. 21, 2018.

(51) Int. Cl.

| | |
|---|---|
| ***A61K 45/06*** | (2006.01) |
| ***A61K 39/00*** | (2006.01) |
| ***A61K 39/395*** | (2006.01) |
| ***A61K 40/15*** | (2025.01) |
| ***A61K 40/31*** | (2025.01) |
| ***A61K 40/41*** | (2025.01) |
| ***C07K 14/54*** | (2006.01) |
| ***C07K 14/705*** | (2006.01) |
| ***C07K 16/28*** | (2006.01) |
| ***C12N 5/0783*** | (2010.01) |
| ***C12N 15/86*** | (2006.01) |

(52) U.S. Cl.

CPC ........ *A61K 45/06* (2013.01); *A61K 39/39541* (2013.01); *A61K 40/15* (2025.01); *A61K 40/31* (2025.01); *A61K 40/418* (2025.01); *C07K 14/54* (2013.01); *C07K 14/70503* (2013.01); *C07K 14/70575* (2013.01); *C07K 16/2887* (2013.01); *C12N 5/0636* (2013.01); *C12N 5/0646* (2013.01); *C12N 15/86* (2013.01); *A61K 2039/505* (2013.01); *A61K 2239/48* (2023.05); *C12N 2500/90* (2013.01); *C12N 2501/2302* (2013.01); *C12N 2502/30* (2013.01); *C12N 2740/10043* (2013.01)

(58) Field of Classification Search

CPC .. A61K 35/17; A61K 39/39541; A61K 45/06; A61K 2039/505; A61K 2239/48; A61K 35/28; A61K 35/51; A61K 38/177; A61K 39/4613; A61K 39/4631; A61K 39/46434; C07K 14/54; C07K 14/70503; C07K 14/70575; C07K 16/2887; C07K 14/7051; C07K 2319/03; C07K 2319/60; C07K 14/70596; C07K 14/5443; C07K 14/705; C07K 14/70525; C07K 14/70528; C07K 16/2803; C07K 16/2866; C12N 5/0636; C12N 5/0646; C12N 15/86; C12N 2500/90; C12N 2501/2302; C12N 2502/30; C12N 2740/10043; C12N 2501/599; C12N 2501/51; C12N 2510/00; C12N 5/0694; A61P 3/10; A61P 11/06; A61P 19/02; A61P 35/00

See application file for complete search history.

(56) References Cited

U.S. PATENT DOCUMENTS

| | | | |
|---|---|---|---|
| 4,536,468 | A | 8/1985 | Yasui et al. |
| 4,981,784 | A | 1/1991 | Evans et al. |
| 5,164,897 | A | 11/1992 | Clark et al. |
| 5,171,671 | A | 12/1992 | Evans et al. |
| 5,342,929 | A | 8/1994 | Ernst et al. |
| 5,552,303 | A | 9/1996 | Grabstein et al. |
| 5,571,696 | A | 11/1996 | Evans et al. |
| 5,602,009 | A | 2/1997 | Evans et al. |
| 5,686,281 | A | 11/1997 | Roberts |

(Continued)

FOREIGN PATENT DOCUMENTS

| | | | |
|---|---|---|---|
| CA | 2519535 A1 * | 2/2007 | ............. A61K 35/17 |
| CA | 2994751 | 2/2017 | |

(Continued)

OTHER PUBLICATIONS

Paul et al. ("The Molecular Mechanism of Natural Killer Cells Function and Its Importance in Cancer Immunotherapy", Front. Immunol., Sep. 13, 2017 Sec. Cancer Immunity and Immunotherapy vol. 8—2017) (Year: 2017).*

(Continued)

*Primary Examiner* — Gary B Nickol
*Assistant Examiner* — Amy M. Chattin
(74) *Attorney, Agent, or Firm* — Norton Rose Fulbright US LLP

(57) ABSTRACT

Provided herein are universal antigen presenting cells. Also provided herein are methods of expanding immune cells using the UAPCs and methods for the treatment of a disease, such as cancer, using the expanded immune cells.

59 Claims, 15 Drawing Sheets

Specification includes a Sequence Listing.

(56) References Cited

U.S. PATENT DOCUMENTS 5,696,233 A 12/1997 Evans et al.
5,707,798 A 1/1998 Brann
5,723,329 A 3/1998 Mangelsdorf et al.
5,747,292 A 5/1998 Greenberg et al.
5,789,187 A 8/1998 Ross et al.
5,843,728 A 12/1998 Seed et al.
5,851,828 A 12/1998 Seed et al.
5,906,936 A 5/1999 Eshhar et al.
5,912,132 A 6/1999 Brann
5,912,170 A 6/1999 Seed et al.
5,912,172 A 6/1999 Eshhar et al.
5,981,195 A 11/1999 Fuller et al.
6,001,973 A 12/1999 Strom et al.
6,004,811 A 12/1999 Seed et al.
6,077,675 A 6/2000 Stormann et al.
6,083,751 A 7/2000 Feldhaus et al.
6,090,914 A 7/2000 Linsley et al.
6,103,521 A 8/2000 Capon et al.
6,120,669 A 9/2000 Bradley
6,284,240 B1 9/2001 Seed et al.
6,361,714 B1 3/2002 Iwabuchi et al.
6,376,198 B1 4/2002 Kopin et al.
6,392,013 B1 5/2002 Seed et al.
6,410,014 B1 6/2002 Seed et al.
6,410,319 B1 6/2002 Raubitschek et al.
6,416,957 B1 7/2002 Evans et al.
6,451,308 B1 9/2002 Strom et al.
6,500,672 B1 12/2002 Sladek et al.
6,509,016 B1 1/2003 Chatterjee et al.
6,534,289 B1 3/2003 Fuller et al.
6,607,879 B1 8/2003 Cocks et al.
6,706,867 B1 3/2004 Lorenz
6,747,665 B1 6/2004 Stoval, III et al.
6,797,263 B2 9/2004 Strom et al.
6,824,974 B2 11/2004 Pisharody et al.
6,937,446 B2 8/2005 Kamiguchi et al.
6,958,236 B2 10/2005 Pascal et al.
6,998,476 B2 2/2006 Strom et al.
7,001,733 B1 2/2006 Ferrick et al.
7,041,467 B2 5/2006 Ferrick et al.
7,049,136 B2 5/2006 Seed et al.
7,052,906 B1 5/2006 Lawson et al.
7,070,995 B2 7/2006 Jensen
7,089,052 B2 8/2006 Kodama et al.
7,094,599 B2 8/2006 Seed et al.
7,105,644 B2 9/2006 Rosen et al.
7,118,751 B1 10/2006 Ledbetter et al.
7,135,603 B2 11/2006 Messenger
7,196,164 B2 3/2007 Rosen et al.
7,196,877 B2 3/2007 Yoshikawa et al.
7,235,190 B1 6/2007 Wilcoxon et al.
7,258,853 B2 8/2007 Strom et al.
7,294,468 B2 11/2007 Bell et al.
7,319,140 B2 1/2008 Bakker et al.
7,320,787 B2 1/2008 Seed et al.
7,332,574 B2 2/2008 Bakker et al.
7,341,944 B2 3/2008 Harutyunyan
7,347,995 B2 3/2008 Strom et al.
7,354,762 B2 4/2008 Jensen
7,379,278 B2 5/2008 Koui et al.
7,446,179 B2 11/2008 Jensen et al.
7,446,190 B2 11/2008 Sadelain et al.
7,468,248 B2 12/2008 DeNise et al.
7,485,600 B2 2/2009 Harutyunyan et al.
7,514,537 B2 4/2009 Jensen
7,569,664 B2 8/2009 Jakobsen et al.
7,569,670 B2 8/2009 Novak et al.
7,572,772 B2 8/2009 Linsley et al.
7,579,439 B2 8/2009 Strom et al.
7,628,986 B2 12/2009 Weber et al.
7,629,171 B2 12/2009 Meagher et al.
7,659,093 B2 2/2010 Bakker et al.
7,700,728 B2 4/2010 Bates et al.
7,723,111 B2 5/2010 Hwu et al.
7,732,133 B2 6/2010 Yabuta et al.
7,732,149 B2 6/2010 Kojima et al.
7,736,644 B2 6/2010 Weber et al.
7,741,465 B1 6/2010 Eshhar et al.
7,834,152 B2 11/2010 Strom et al.
7,919,086 B2 4/2011 Nakano et al.
7,948,154 B2 5/2011 Ifuku et al.
7,964,349 B2 6/2011 Bell et al.
7,968,687 B2 6/2011 McDonagh et al.
7,972,438 B2 7/2011 Fei et al.
7,998,736 B2 8/2011 Morgan et al.
8,008,029 B2 8/2011 Lefevre
8,026,097 B2 9/2011 Campana et al.
8,088,589 B2 1/2012 Muraca
8,105,769 B2 1/2012 Bell et al.
8,120,239 B2 2/2012 Cheon et al.
8,124,084 B2 2/2012 Lefrancois et al.
8,124,361 B2 2/2012 Slack et al.
8,129,125 B2 3/2012 Muraca
8,158,360 B2 4/2012 Heise et al.
8,178,660 B2 5/2012 Weiner et al.
8,263,375 B2 9/2012 Abassi et al.
8,329,421 B2 12/2012 Powell et al.
8,350,108 B2 1/2013 Cortright et al.
8,367,882 B2 2/2013 Cortright et al.
8,399,645 B2 3/2013 Campana et al.
8,435,762 B2 5/2013 Sternson et al.
8,450,112 B2 5/2013 Li et al.
8,465,743 B2 6/2013 Rosenberg et al.
8,465,916 B2 6/2013 Bell et al.
8,535,672 B2 9/2013 Kaempfer et al.
8,591,858 B2 11/2013 Harutyunyan et al.
8,592,567 B2 11/2013 Weiner et al.
8,679,492 B2 3/2014 Blein et al.
8,710,186 B2 4/2014 Li et al.
8,771,664 B2 7/2014 Berraondo Lopez et al.
8,796,421 B2 8/2014 Li et al.
8,802,374 B2 8/2014 Jensen
8,822,196 B2 9/2014 Rosenberg et al.
8,822,647 B2 9/2014 Jensen
8,859,275 B2 10/2014 Notka et al.
8,871,114 B2 10/2014 Miyagawa et al.
8,871,191 B2 10/2014 Pavlakis et al.
8,877,199 B2 11/2014 Rader et al.
8,883,992 B2 11/2014 Damschroder et al.
8,900,816 B2 12/2014 Schmittling et al.
8,900,820 B2 12/2014 Muraca
8,906,682 B2 12/2014 June et al.
8,911,993 B2 12/2014 June et al.
8,912,385 B2 12/2014 Meagher
8,916,381 B1 12/2014 June et al.
8,940,288 B2 1/2015 Lefrancois et al.
8,975,071 B1 3/2015 June et al.
9,035,036 B2 5/2015 Bell et al.
9,040,669 B2 5/2015 Cheung et al.
9,062,287 B2 6/2015 Ideno et al.
9,101,584 B2 8/2015 June et al.
9,102,760 B2 8/2015 June et al.
9,102,761 B2 8/2015 June et al.
9,115,171 B2 8/2015 Ong et al.
9,156,915 B2 10/2015 Waldman et al.
9,163,258 B2 10/2015 Riddell et al.
9,169,328 B2 10/2015 Spriggs et al.
9,175,308 B2 11/2015 Shiku et al.
9,181,527 B2 11/2015 Sentman
9,187,732 B2 11/2015 Wolschek et al.
9,212,104 B2 12/2015 Qiao et al.
9,212,229 B2 12/2015 Schonfeld et al.
9,220,728 B2 12/2015 Sadelain et al.
9,233,125 B2 1/2016 Davila et al.
9,260,696 B2 2/2016 Kaufman et al.
9,266,960 B2 2/2016 Morgan et al.
9,272,002 B2 3/2016 Powell, Jr. et al.
9,273,283 B2 3/2016 Sentman
9,315,585 B2 4/2016 Cheung et al.
9,328,156 B2 5/2016 June et al.
9,359,447 B2 6/2016 Feldman et al.
9,365,630 B2 6/2016 Lefrancois et al.
9,365,641 B2 6/2016 June et al.
9,371,368 B2 6/2016 Lefrancois et al.

(56) References Cited

U.S. PATENT DOCUMENTS 9,393,268 B2 7/2016 Waldman et al.
9,394,368 B2 7/2016 Brogdon et al.
9,402,865 B2 8/2016 Powell et al.
9,422,351 B2 8/2016 Scholler et al.
9,422,360 B2 8/2016 Suo et al.
9,446,105 B2 9/2016 Powell, Jr.
9,447,194 B2 9/2016 Jensen
9,453,075 B2 9/2016 Cheung et al.
9,464,140 B2 10/2016 June et al.
9,476,028 B2 10/2016 Karlsson-Parra et al.
9,481,728 B2 11/2016 June et al.
9,487,800 B2 11/2016 Schonfeld et al.
9,492,499 B2 11/2016 Jaynes et al.
9,493,740 B2 11/2016 Brenner et al.
9,499,629 B2 11/2016 June et al.
9,499,823 B2 11/2016 De Lorenzo et al.
9,511,092 B2 12/2016 Campana et al.
9,518,119 B2 12/2016 Bergstein
9,518,123 B2 12/2016 June et al.
9,518,132 B2 12/2016 Li et al.
9,522,955 B2 12/2016 Rosenberg et al.
9,540,445 B2 1/2017 June et al.
9,555,105 B2 1/2017 Riley et al.
9,562,087 B2 2/2017 Ring et al.
9,572,836 B2 2/2017 June et al.
9,572,837 B2 2/2017 Wu
9,573,988 B2 2/2017 Brogdon et al.
9,580,685 B2 2/2017 Jensen
9,587,020 B2 3/2017 Wu et al.
9,597,357 B2 3/2017 Gregory et al.
9,605,049 B2 3/2017 Campana et al.
9,617,336 B2 4/2017 Cojocaru et al.
9,623,049 B2 4/2017 Eshhar et al.
9,623,082 B2 4/2017 Copik et al.
9,624,276 B2 4/2017 Young et al.
9,624,306 B2 4/2017 Morgan et al.
9,629,877 B2 4/2017 Cooper et al.
9,650,428 B2 5/2017 Sampath et al.
9,657,105 B2 5/2017 Forman et al.
9,663,763 B2 5/2017 Sentman
9,670,281 B2 6/2017 Lim et al.
9,677,136 B2 6/2017 Denise et al.
9,685,295 B2 6/2017 King et al.
9,688,740 B2 6/2017 Choi et al.
9,688,760 B2 6/2017 Kufer et al.
9,701,758 B2 7/2017 Cooper et al.
9,708,384 B2 7/2017 Scholler et al.
9,714,278 B2 7/2017 June et al.
9,725,492 B2 8/2017 Felber et al.
9,725,519 B2 8/2017 Masuko et al.
9,745,368 B2 8/2017 Milone et al.
9,765,142 B2 9/2017 Dimitrov et al.
9,765,342 B2 9/2017 Kochenderfer
9,777,061 B2 10/2017 Ebersbach et al.
9,783,591 B2 10/2017 June et al.
9,790,261 B2 10/2017 Felber et al.
9,790,278 B2 10/2017 Sentman et al.
9,790,282 B2 10/2017 Orentas et al.
9,809,581 B2 11/2017 Chen et al.
9,815,901 B2 11/2017 Brogdon et al.
9,815,908 B2 11/2017 Schonfeld et al.
9,821,011 B1 11/2017 Sentman
9,821,012 B2 11/2017 Wu et al.
9,822,340 B1 11/2017 Sentman
9,828,399 B2 11/2017 Tremblay et al.
9,828,435 B2 11/2017 Evans et al.
9,833,476 B2 12/2017 Zhang et al.
9,833,480 B2 12/2017 Junghans et al.
9,834,545 B2 12/2017 Chen et al.
9,834,590 B2 12/2017 Campana et al.
9,845,362 B2 12/2017 Mukherjee
9,855,297 B2 1/2018 Duchateau et al.
9,855,298 B2 1/2018 Bot et al.
9,856,176 B2 1/2018 Harris et al.
9,856,322 B2 1/2018 Campana et al.
9,856,497 B2 1/2018 Qi et al.
9,868,774 B2 1/2018 Orentas et al.
9,889,160 B2 2/2018 Jantz et al.
9,889,161 B2 2/2018 Jantz et al.
9,913,882 B2 3/2018 Slawin et al.
9,914,909 B2 3/2018 Brown et al.
9,920,132 B2 3/2018 Wels et al.
9,931,347 B2 4/2018 Cowley et al.
9,931,377 B2 4/2018 Pavlakis et al.
9,932,387 B2 4/2018 Lefrancois et al.
9,932,405 B2 4/2018 Xiao et al.
9,932,572 B2 4/2018 Spencer et al.
9,938,497 B2 4/2018 Sentman
9,944,702 B2 4/2018 Galetto
9,944,709 B2 4/2018 Galetto
9,944,931 B2 4/2018 Wucherpfennig et al.
9,950,010 B1 4/2018 Jantz et al.
9,950,011 B1 4/2018 Jantz et al.
9,951,118 B2 4/2018 Kitchen et al.
9,957,480 B2 5/2018 Sentman
9,963,497 B2 5/2018 Kaempfer et al.
9,969,790 B2 5/2018 Lefrancois et al.
9,987,308 B2 6/2018 Riddell et al.
10,011,658 B2 7/2018 Liu et al.
10,023,648 B2 7/2018 Hombach et al.
10,040,846 B2 8/2018 Frigault et al.
10,071,118 B2 9/2018 Katz et al.
10,072,078 B2 9/2018 Orentas et al.
10,117,897 B2 11/2018 Sadelain et al.
10,166,255 B2 1/2019 Moriarity et al.
10,351,612 B2 7/2019 Schonfeld et al.
10,406,177 B2 9/2019 Moriarity et al.
10,464,989 B2 11/2019 Walcheck et al.
11,104,735 B2 8/2021 Huntington et al.
11,696,927 B2 7/2023 Copik et al.
2002/0102264 A1 8/2002 Cheung
2003/0148982 A1 8/2003 Brenner et al.
2004/0038886 A1 2/2004 Finney et al.
2006/0110360 A1 5/2006 Klingemann
2007/0071759 A1 3/2007 Shin et al.
2008/0050341 A1 2/2008 Morgan et al.
2009/0041804 A1 2/2009 Schlom et al.
2010/0105136 A1 4/2010 Carter et al.
2010/0152421 A1 6/2010 Nishimura et al.
2011/0014162 A1 1/2011 Lowdell
2011/0236411 A1 9/2011 Scholler et al.
2011/0286980 A1 11/2011 Brenner
2012/0040452 A1 2/2012 Nishimura et al.
2012/0148552 A1 6/2012 Jensen
2012/0171173 A1* 7/2012 Ideno ..................... A61P 31/06 435/375
2012/0308986 A1 12/2012 Deng et al.
2013/0001376 A1 1/2013 Peled et al.
2013/0280221 A1 10/2013 Schonfeld et al.
2013/0308986 A1 11/2013 Sato
2014/0044714 A1 2/2014 Ho et al.
2014/0212446 A1 7/2014 Riley et al.
2014/0220053 A1 8/2014 Muraca et al.
2014/0255363 A1 9/2014 Metelitsa et al.
2014/0322216 A1 10/2014 Kaplan
2015/0190429 A1 7/2015 Beelen et al.
2015/0224143 A1 8/2015 Malmberg et al.
2015/0368360 A1 12/2015 Liang et al.
2015/0376296 A1 12/2015 Fedorov et al.
2016/0145337 A1 5/2016 Galetto et al.
2016/0151491 A1 6/2016 Rabinovich et al.
2016/0158285 A1 6/2016 Cooper et al.
2016/0207989 A1 7/2016 Short
2017/0008963 A1 1/2017 Brogdon et al.
2017/0067021 A1 3/2017 Moriarity et al.
2017/0081405 A1 3/2017 Adusumilli et al.
2017/0119682 A1 5/2017 De La Rosa et al.
2017/0119865 A1 5/2017 Lee et al.
2017/0152480 A1 6/2017 Jensen
2017/0319659 A1 11/2017 Copik et al.
2017/0335281 A1 11/2017 Loew et al.
2018/0142035 A1 5/2018 Lobb et al.
2019/0046659 A1 2/2019 Wang et al.
2019/0345217 A1 11/2019 Ma et al.

(56) References Cited

U.S. PATENT DOCUMENTS

2020/0009193 A1 1/2020 Han et al.
2020/0046766 A1 2/2020 Niazi et al.
2020/0046779 A1 2/2020 Niazi et al.
2020/0390816 A1 12/2020 Kerbauy et al.
2021/0230548 A1 7/2021 Daher et al.

FOREIGN PATENT DOCUMENTS

CA 3046576 6/2018
CN 103483453 1/2014
CN 105861430 8/2016
CN 106397593 2/2017
CO 2021014353 1/2022
CO 2021013127 3/2022
EA 201791442 A1 5/2018
EP 2614151 7/2013
EP 2995682 3/2016
EP 3333192 6/2018
EP 3154581 2/2019
EP 2877187 6/2019
JP 2015-502756 A 1/2015
JP 2015-519890 A 7/2015
JP 2016-504324 A 2/2016
JP 2017-532353 A 11/2017
RU 2422513 6/2011
TW 201615832 A 5/2016
WO WO 1995/001994 1/1995
WO WO 2005/007199 1/2005
WO 2005/042774 A2 5/2005
WO WO 2006/133398 12/2006
WO 2007/136673 A2 11/2007
WO WO 2008/060510 5/2008
WO 2009/015842 A2 2/2009
WO 2009/153992 A1 12/2009
WO WO 2010/042189 4/2010
WO WO-2010037395 A2 * 4/2010 ......... A61K 39/0011
WO 2010/049935 A1 5/2010
WO WO 2012/033885 3/2012
WO WO 2012/136231 10/2012
WO WO 2013/040371 3/2013
WO WO 2013/070468 5/2013
WO WO 2013/094988 6/2013
WO WO 2013/163171 10/2013
WO WO 2014/093948 6/2014
WO WO 2014/138314 9/2014
WO WO 2014/184744 11/2014
WO WO 2014/186469 11/2014
WO WO 2015/051247 4/2015
WO WO-2015132415 A1 * 9/2015 ........... A01N 1/0263
WO 2015/154012 A1 10/2015
WO WO 2016/044811 3/2016
WO WO 2016/069607 5/2016
WO WO-2016070119 A1 * 5/2016 .............. A61P 35/00
WO WO 2016/102965 6/2016
WO WO 2016/109668 7/2016
WO WO 2016/172606 10/2016
WO WO 2016/174405 11/2016
WO WO 2016/210293 12/2016
WO WO-2016197108 A1 * 12/2016 ......... A61K 40/4211
WO WO 2017/001572 1/2017
WO WO 2017/020812 2/2017
WO WO 2017/023801 2/2017
WO WO 2017/023803 2/2017
WO WO 2017/027843 2/2017
WO 2017/037083 A1 3/2017
WO 2017/042393 A1 3/2017
WO WO 2017/048809 3/2017
WO WO 2017/048902 3/2017
WO WO 2017/096329 6/2017
WO WO 2017/100861 6/2017
WO WO 2017/123556 7/2017
WO WO 2017/123956 7/2017
WO 2017/132358 A1 8/2017
WO WO 2017/160986 B1 9/2017
WO WO 2017/173384 10/2017
WO WO 2017/205810 11/2017
WO WO 2017/220704 12/2017
WO WO 2017/222593 12/2017
WO 2018/014038 A1 1/2018
WO WO 2018/013797 1/2018
WO 2018022646 A1 2/2018
WO WO 2018/027155 2/2018
WO WO 2018/053885 3/2018
WO WO 2018/071682 4/2018
WO WO 2018/081470 5/2018
WO WO 2018/108859 6/2018
WO WO 2018/195339 10/2018
WO WO 2018/208670 11/2018
WO WO 2018208606 11/2018
WO WO 2019/089884 5/2019
WO WO 2019/099927 5/2019
WO WO-2019090355 A1 * 5/2019 ............ C07K 14/71
WO WO 2019/157130 8/2019
WO WO 2019/169141 9/2019
WO WO 2019/210832 11/2019
WO WO 2019/213610 11/2019
WO WO 2019/217512 11/2019
WO 2020/043670 A1 3/2020
WO 2020/073029 A1 4/2020
WO 2020/112493 A1 6/2020
WO WO 2020/187340 9/2020
WO WO 2020/198675 10/2020
WO WO 2020/205359 10/2020

OTHER PUBLICATIONS

Sarvaria et al. ("Umbilical Cord Blood Natural Killer Cells, Their Characteristics, and Potential Clinical Applications" Front. Immunol., Mar. 23, 2017 Sec. Alloimmunity and Transplantation vol. 8—2017) (Year: 2017).*

Anand et al. ("Cancer is a Preventable Disease that Requires Major Lifestyle Changes". Pharm Res 25, 2097-2116 (2008)) (Year: 2008).*

Dickens et al. ("Principles of cancer treatment by chemotherapy", Surgery (Oxford), vol. 36, Issue 3, 2018, pp. 134-138 (Year: 2018).*

Denman CJ, et al. Membrane-bound IL-21 promotes sustained ex vivo proliferation of human natural killer cells. PLoS One. 2012;7(1):e30264. doi: 10.1371/journal.pone.0030264. Epub Jan. 18, 2012. PMID: 22279576; PMCID: PMC3261192. (Year: 2012).*

González-Cabrero J, Wise CJ, Latchman Y, Freeman GJ, Sharpe AH, Reiser H. CD48-deficient mice have a pronounced defect in CD4(+) T cell activation. Proc Natl Acad Sci U S A. Feb. 2, 1999;96(3):1019-23. doi: 10.1073/pnas.96.3.1019. PMID: 9927686; PMCID: PMC15343. (Year: 1999).*

Kumaresan PR, Lai WC, Chuang SS, Bennett M, Mathew PA. CS1, a novel member of the CD2 family, is homophilic and regulates NK cell function. Mol Immunol. Sep. 2002;39(1-2):1-8. doi: 10. 1016/s0161-5890(02)00094-9. PMID: 12213321. (Year: 2002).*

Butler MO, Hirano N. Human cell-based artificial antigen-presenting cells for cancer immunotherapy. Immunol Rev. Jan. 2014;257(1):191-209. doi: 10.1111/imr. 12129. PMID: 24329798; PMCID: PMC3869003. (Year: 2014).*

Shah N et al. Antigen presenting cell-mediated expansion of human umbilical cord blood yields log-scale expansion of natural killer cells with anti-myeloma activity. PLoS One. Oct. 18, 2013;8(10):e76781. doi: 10.1371/journal.pone.0076781. PMID: 24204673; PMCID: PMC3800010. (Year: 2013).*

Kim JV, Latouche JB, Rivière I, Sadelain M. The ABCs of artificial antigen presentation. Nat Biotechnol. Apr. 2004;22(4):403-10. doi: 10.1038/nbt955. PMID: 15060556. (Year: 2004).*

BD Biosciences ("BD"), "Human and Mouse CD Markers Handbook", HLDA10 meeting markers, 2016. (Year: 2016).*

Denman CJ, et al.Membrane-boundIL-21 promotes sustained ex vivo proliferation of human natural killer cells. PLoSOne. 2012;7(1): e30264. doi: 10.13710030264. Epub Jan. 18, 2012. PMID: 22279576; PMCID: PMC 3261192. (Year: 2012).*

Gonzalez-Cabrero J, et al. CD48-deficient mice have a pronounced defect in CD4(+) T cell activation. Proc Natl Acad Sci USA. Feb. 2, 1999; 96(3):1019-23. PMID: 9927686; PMC ID: PMC 15343 (Year: 1999).*

(56) References Cited

OTHER PUBLICATIONS

Kumaresan PR, et al. CS1, a novel member of the CD2 family, is homophilic and regulates NK cell function. Mol Immunol. Sep. 2002; 39(1-2): 1-8. PMID: 12213321. (Year: 2002).*
Butler MO, et al. Human cell-based artificial antigen-presenting cells for cancer immunotherapy. Immunol Rev. Jan. 2014; 257(1): 191-209. PMID: 24329798; PMC ID: PMC 3869003. (Year: 2014).*
Shah N et al. Antigen presenting cell-mediated expansion of human umbilical cord blood yields log-scale expansion of natural killer cells with anti-myeloma activity. PLoSOne. Oct. 18, 2013; 8(10): e76781.PMID:24204673; PMC ID: PMC 3800010. (Year: 2013).*
Kim JV, et al. The ABCs of artificial antigen presentation. Nat Biotechnol. Apr. 2004;22(4):403-10. PMID: 15060556 (Year: 2004).*
McNerney et al. 2B4 (CD244)-CD48 interactions provide a novel MHC class I-independent system for NK-cell self-tolerance in mice. Blood. Aug. 15, 2005;106(4):1337-40. (Year: 2005).*
Nakajima et al. Activating interactions in human NK cell recognition: the role of 2B4-CD48. Eur. J. Immunol. 1999. 29: 1676-1683. (Year: 2006).*
Wang et al. Membrane-bound interleukin-21 and CD137 ligand induce functional human natural killer cells from peripheral blood mononuclear cells through STAT-3 activation. Clinical and Experimental Immunology, 172: 104-112, 2012. (Year: 2012).*
Shah et al. Antigen Presenting Cell-Mediated Expansion of Human Umbilical Cord Blood Yields Log-Scale Expansion of Natural Killer Cells with Anti-Myeloma Activity. PLOS One. Oct. 2013, vol. 8, Issue 10, e76781. (Year: 2013).*
Butler and Hirano. Human cell-based artificial antigen-presenting cells for cancer immunotherapy. Immunol Rev. Jan. 2014; 257(1):. doi:10.1111/imr.12129. (Year: 2014).*
Chu et al. Targeting CD20+ Aggressive B-cell Non-Hodgkin Lymphoma by Anti-CD20 CAR mRNA-Modified Expanded Natural Killer Cells In Vitro and in NSG Mice. Cancer Immunol Res; 3(4) Apr. 2015. (Year: 2015).*
Springer Protocols. Natural Killer Cells: Methods and Protocols. Editor: Srinivas S. Somanchi. 2016. (Year: 2016).*
Chabannon et al. Manufacturing natural Killer Cells as Medicinal Products. Frontiers in Immunology. Nov. 2016, vol. 7, Article 504. (Year: 2016).*
Joseph D Malaer, Porunelloor A Mathew. CS1 (SLAMF7, CD319) is an effective immunotherapeutic target for multiple myeloma. Am J Cancer Res 2017;7(8):1637-1641. (Year: 2017).*
Ayello et al. Genetically re-engineered K562 cells significantly expand and functionally activate cord blood natural killer cells: Potential for adoptive cellular immunotherapy. Experimental Hematology 2017;46:38-47. (Year: 2017).*
Daher et al., "Targeting a cytokine checkpoint enhances the fitness of armored cord blood CAR-NK cells," Blood, 137(5):624-636, 2021.
Extended European Search Report issued in European Patent Application No. 19757670.5, dated Nov. 12, 2021.
Liu et al., "GMP-Compliant Universal Antigen Presenting Cells (uAPC) Promote the Metabolic Fitness and Antitumor Activity of Armored Cord Blood CAR-NK Cells," Frontiers in Immunology, 12:626098, 14 pages, 2021.
Suhoski et al., "Engineering artificial antigen-presenting cells to express a diverse array of co-stimulatory molecules," Molecular Therapy, 15(5):981-988, 2007.
English translation of Office Communication issued in Russian Patent Application No. 2021118674, dated Jan. 9, 2024.
Office Communication issued in U.S. Appl. No. 16/970,937 dated Jan. 11, 2024.
Office Communication issued in Chinese Patent Application No. 202080032042.7, dated Sep. 29, 2023.
Office Communication issued in Korean Patent Application No. 10-2019-7034119, dated Oct. 6, 2023.
Srivastava et al., "Engineering CAR-T cells: Design concepts," Trends Immunol., 36(8):494-502, Aug. 2015.
Viel et al., "TGF-β inhibits the activation and functions of NK cells by repressing the mTOR pathway," Sci Signal., 9(415):ra19, Feb. 16, 2016.
English translation of Office Communication issued in Eurasian Patent Application No. dated Aug. 18, 2023.
Caruana et al., "Boosting in vivo CAR-redirected virus-specific CTLs with universal-artificial antigen presenting cells." Blood 2013, 122(21), p. 4204.
Chu et al., "Genetic Modification of T Cells Redirected toward CS1 Enhances Eradication of Myeloma Cells." Clinical Cancer Research 2014, 20(15), 3989-4000.
Mcardel et al., "Roles of CD48 in regulating immunity and tolerance." Clinical Immunology 2016, 164, 10-20.
Rushworth et al., "Universal Artificial Antigen Presenting Cells to Selectively Propagate T Cells Expressing Chimeric Antigen Receptor Independent of Specificity." Journal of Immunotherapy 2014, 37(4), 203-213.
Search Report issued in Corresponding Singapore Application No. 11202008008U, dated Jan. 20, 2022.
Liu et al., "Cord blood derived natural killer cells engineered with a chimeric antigen receptor targeting CD19 and expressing IL-15 have long term persistence and exert potent anti-leukemia activity," Blood, 126(23):3091, 2015.
Amati et al., "Generation of mesenchymal stromal cells from cord blood: evaluation of in vitro quality parameters prior to clinical use," Stem Cell Research & Therapy, 8:14, pp. 1-15, 2017.
Badri et al., "Optimization of radiation dosing schedules for proneural glioblastoma," J. Math. Biol., 72(5):1301-1336, 2016.
Baylot et al., "TCTP has a Crucial Role in the Different Stages of Prostate Cancer Malignant Progression," Results and Problems in Cell Differentiation, 64:225-261, 2017.
Bhatta et al., "Education: The Key to Curb HIV and AIDS Epidemic," Kathmandu University Medical Journal, 42(2):158-161, 2013.
Chongbi et al., "Principle and Technology of Molecular Immunological Methods," Science and Technology Documentation Press, pp. 222-223, 2016. (English summary).
De Witte et al., "Cytokine treatment optimises the immunotherapeutic effects of umbilical cord-derived MSC for treatment of inflammatory liver disease," Stem Cell Research & Therapy, 8:140, pp. 1-12, 2017.
English machine translation of Office Communication issued in Colombian Patent Application No. NC2021/0007657, dated Jul. 31, 2023.
English translation of Office Communication issued in Chinese Patent Application No. 201980089617.6, dated Jul. 26, 2023.
English translation of Office Communication issued in Japanese Patent Application No. 2021-518730, dated Aug. 29, 2023.
English translation of Office Communication issued in Russian Patent Application No. 2021131582, dated Aug. 24, 2023.
Kloß et al., "Optimization of human NK cell manufacturing: Fully-automated separation, improved ex vivo expansion using IL-21 with autologous feeder cells and generation of anti-CD123-CAR-expressing effector cells," Human Gene Therapy, 28(10):897-913, 2017.
Quatrini et al., "The Immune Checkpoint PD-1 in Natural Killer Cells: Expression, Function and Targeting in Tumour Immunotherapy," Cancers, 12(11):3285, 20 pages, 2020.
Stretlsova et al., "Characteristics of Populations and Clones NK-Cells Obtained by Stimulation Interleukin 2 and Genetic Modified Feeder Cells K562, Expressing Membrane-Bound Interleukin 21," Medical Immunology, 19(5):62-63, 2017.
Tongjing et al., "Basic and Clinic of Th Genus Cell Polarization Colony," Military Medical Science Press, p. 77, 2002. (English summary).
Weimin et al., "Methodology for Cytokine Research," People's Medical Publishing House, p. 463, 1999. (English summary).
Wu et al., "Development and Functional Control of Natural Killer Cells by Cytokines," Frontiers in Immunology, 8(930), 18 pages, 2017.

(56) References Cited

OTHER PUBLICATIONS

Caruana et al., "K562-Derived Whole-Cell Vaccine Enhances Antitumor Responses of CAR-Redirected Virus-Specific Cytotoxic T Lymphocytes In Vivo," Clinical Cancer Research, 21(13):2952-2962, 2015.
English translation of Search Report issued in ROC (Taiwan) Patent Application No. 108105835, date of completion of search Apr. 18, 2023.
Stark and Watzl, "2B4 (CD244), NTB-A and CRACC (CS1) stimulate cytotoxicity but no proliferation in human NK cells," International Immunology, 18(2):241-247, 2006.
Tomchuck et al., "Enhanced Cytotoxic Function of Natural Killer and CD3+CD56+ Cells in Cord Blood Following Culture," Biol. Blood Marrow Transplant, 21(1):39-49, 2015.
Bihi et al., "Mechanisms of NK cell activation: CD4+ T cells enter the scene," Cell. Mol. Life Sci., 68:3457-3467, 2011.
English translation of Office Communication issued in Russian Patent Application No. 2021118674, dated Mar. 23, 2023.
Kaartinen et al., "Low interleukin-2 concentration favors generation of early memory T cells over effector phenotypes during chimeric antigen receptor T-cell expansion," Cytotherapy, 19:689-702, 2017.
Kambayashi et al., "Atypical MHC class II-expressing antigen-presenting cells: can anything replace a dendritic cell?" Nature Reviews: Immunology, 14:719-730, 2014.
Nogrady, "Nature Killer Cell Therapies Catch Up to CAR T," The Scientist, 7 pages, 2020.
Rybachuk et al., "Immunophenotype of NK Cells During Long-Term Cultivation of Mononuclear Cells," Genes & Cells, 17(3): 199-200, 2022. (English Machine Translation).
Söderström et al., "Nature killer cells trigger osteoclastogenesis and bone destruction in arthritis," PNAS, 107(29):13028-13033, 2010.
English translation of Office Communication issued in Japanese Patent Application No. 2020-544206, dated Jan. 6, 2023.
Extended European Search Report issued in European Patent Application No. 19869661.9, dated May 18, 2022.
English summary/translation of Chu, Yi Wei, edited, In: Medical Immunology, Fudan University Press, p. 281, Nov. 2015.
English translation of Office Communication issued in Chinese Patent Application No. 201980089617.6, dated Jan. 26, 2024.
English translation of Office Communication issued in Colombian Patent Application No. NC2020/0015168, dated Jan. 23, 2024.
Messmer et al., "CD48 Stimulation by 2B4 (CD244)-Expressing Targets Activates Human NK Cells," The Journal of Immunology, 176:4646-4650, 2006.
Office Communication issued in Russian Patent Application No. 2020130838, dated Apr. 29, 2022.
Bajgain et al., "Optimizing the production of suspension cells using the G-Rex "M" series," Methods & Clinical Development, 1:14015, 9 pages, 2014.
Bin et al. edited, "Treatment of Femoral-Head Necrosis by Integrated traditional Chinese and Western Medicine", Shandong Science and Technology Press, publication date: Mar. 2018, p. 33. (Partial English Translation).
Capelli et al., "Clinical grade expansion of MSCs," Immunology Letters, 168(2):222-227, 2015.
Kandoi et al., "Evaluation of platelet lysate as a substitute for FBS in explant and enzymatic isolation methods of human umbilical cord MSCs," Scientific Reports, 8(1):12439, 12 pages, 2018.
Lechanteur et al., "Large-Scale Clinical Expansion of Mesenchymal Stem Cells in the GMP-Compliant, Closed Automated Quantum® Cell Expansion System: Comparison with Expansion in Traditional T-Flasks," J. Stem. Cell. Res. Ther., 4(8):1-11, 2014.
Mazarzaei et al., "Memory and CAR-NK cell-based novel approaches for HIV vaccination and eradication," J. Cell. Physiol., 234(9):14812-14817, 2019.
Rambaldi, "Umbilical Cord Derived Mesenchymal Stromal Cells for the Treatment of Severe Steroid-resitant Graft versus Host Disease (PCT-UC-MSC)," ClinicalTrials.gov identifier: NCT02032446. Updated Jan. 18, 2019. Accessed Nov. 20, 2024. Available at https://clinicaltrials.gov/study/NCT02032446.
Rham et al., "The proinflammatory cytokines IL-2, IL-15 and IL-21 modulate the repertoire of mature human natural killer cell receptors," Arthritis Res. Ther., 9(6):R125, 2007.
The University of Texas MD Anderson Cancer Center, General Donor Information, available at https://www.mdanderson.org/donors-volunteers/other-ways-to-help/give-blood/donation-instructions.html, retrieved from the web on Dec. 10, 2024.
Zhongli et al. edited, "Orthopedic Course of China-Japanese Friendship Hospital," Jilin University Press, publication date: Sep. 2009, p. 194. (Partial English Translation).
Zongliu et al. edited, "Basic and Clinical Applications of Perinatal Adult Stem Cells", Yunnan Science and Technology Press, publication date: Aug. 2018, p. 5. (Partial English Translation).
English translation of Office Communication issued in Japanese Patent Application No. 2021-557909, dated May 7, 2024.
Imai et al., "Translational Research on the Use of Genetically Modified Human Natural Killer Cells for Refractory Leukemia," KAKEN, Grant-in-Aid for Scientific Research, Project No. 21591349, Project Period: 2009-2012, retrieved from Internet: https://kaken.nii.ac.jp/en/grant/KAKENHI-PROJECT-21591349/, 6 pages, 2014. (English Abstract).
Ding et al., "Signaling pathways in rheumatoid arthritis: implications for targeted therapy," Signal Transduction Target Ther., 8(1):68, 24 pages, 2023.
English translation of Office Communication issued in Russian Patent Application No. 2021131582, dated Jul. 9, 2024.
Gur et al., "LGR5 expressing skin fibroblasts define a major cellular hub perturbed in scleroderma," Cell, 185:1373-1388, 2022.
Kebriaei et al., "Adult Human Mesenchymal Stem Cells Added to Corticosteroid Therapy for the Treatment of Acute Graft-versus-Host Disease," Biol. Blood Marrow Transplant., 15 804-811, 2009.
Locatelli et al., "Graft versus host disease prophylaxis with low-dose cyclosporine-A reduces the risk of relapse in children with acute leukemia given HLA-identical sibling bone marrow transplantation: results of a randomized trial," Blood, 95(5):1572-1579, 2000.
Min et al., "Efficient method for isolation of human umbilical cord mesenchymal stem cells," Chinese Journal of Tissue Engineering Research, 45:8406-8412, 2012.
Office Communication issued in U.S. Appl. No. 17/281,853, dated Jun. 12, 2024.
Volovitz et al., "A non-aggressive, highly efficient, enzymatic method for dissociation of human brain-tumors and brain-tissues to viable single-cells," BMC Neurosci., 17(1):30, 10 pages, 2016.
Seo et al., "Current Strategies to Enhance Adipose Stem Cell Function: An Update," Int. J. Mol. Sci., 20:3827, 32 pages, 2019.
Zhang et al., "Exosomes originating from MSCs stimulated with TGF-β and IFN-γ promote Treg differentiation," J. Cell. Physiol., 233:6832-6840, 2018.
Office Communication issued in U.S. Appl. No. 17/593,085, dated Aug. 19, 2024.
Reddy et al., "Strategies to Prevent EBV Reactivation and Post-transplant Lymphoproliferative Disorders (PTLD) after Allogeneic Stem Cell Transplantation in High-Risk Patients," Bio. Blood Marrow Transplant., 17:591-597, 2011.
Chlewicki et al., "Molecular Basis of the Dual Functions of 2B4 (CD244)[1]," J Immunol., 180(12):8159-67, 2008.
Mcnerney et al., "2B4 (CD244)-CD48 interactions provide a novel MHC class I-independent system for NK-cell self-tolerance in mice," Blood, 106(4):1337-40, 2005.
Sivori et al., "Early expression of triggering receptors and regulatory role of 2B4 in human natural killer cell precursors undergoing in vitro differentiation," PNAS, 99(7):31, 2002.
Imamura et al., "Autonomous growth and increased cytotoxicity of natural killer cells expressing membrane-bound interleukin-15," Blood, 124(7):1081-1088, 2014.
Mehta et al., "NK cell therapy for hematologic malignancies," International Journal of Hematology, 107:262-270, 2018.
Pasha et al., "Development and testing of a stepwise thaw and dilute protocol for cyrorserved umbilical cord blood units," Transfusion, 57(7):1744-1754, 2017.
Office Communication issued in Canadian Patent Application No. 3,091,671, dated Aug. 27, 2025.

(56) References Cited

OTHER PUBLICATIONS

Spolski and Leonard, "Interleukin-21: basic biology and implications for cancer and autoimmunity," Annu. Rev. Immunol., 26:57-79, 2008.
Extended European Search Report issued in Corresponding European Application No. 19757916.2, dated Oct. 15, 2021.
Fang et al., "NK cell-based immunotherapy for cancer" *Seminars in Immunology* 2017, 31, 37-54.
Knorr et al., "Clinical utility of natural killer cells in cancer therapy and transplantation" *Seminars in Immunology* 2014, 26, 161-172.
Lusty et al. "IL-18/IL-15/IL-12 synergy induces elevated and prolonged IFN-[gamma] production byex vivoexpanded NK cells which is not due to enhanced STAT4 activation" *Molecular Immunology* 2017, 88, 138-147.
Avello, Janet et al: "Genetically re-engineered K562 cells significantly expand and functionally activate cord blood natural killer cells: Potential for adoptive cellular immunotherapy", Experimental Hematology, vol. 46, Oct. 17, 2016 (Oct. 17, 2016), pp. 38-47, Elsevier Inc, US.
Broekman et al: "TNF-? and IL-1?-activated human mesenchymal stromal cells increase airway epithelial wound healing in vitro via activation", Respiratory Research (2016) 17:3.
Denman et al: "Membrane-Bound IL-21 Promotes Sustained Ex Vivo Proliferation of Human Natural Killer Cells", PLoS One, Jan. 2012, vol. 7, Issue 1, e30264.
Depombo et al: "3198 Large-Scale, Bioreactor-Generated Expansion of Umbilical Cord Blood Tissue-Derived Mesenchymal Stromal Cells for Clinical Use", Cell Collection and Processing Program: Oral and Poster Abstracts, Session: 711. Cell Collection and Processing: Poster II, Sunday, Dec. 10, 2017, 6:00 PM-8:00 PM.
Fazzina et al: "A new standardized clinical-grade protocol for banking human umbilical cord tissue cells", Transfusion, vol. 55, Dec. 2015, pp. 2864-2873.
Han et al. "Interleukin-17 enhances immunosuppression by mesenchymal stem cells", Cell Death Differ, Jul. 18, 2014, vol. 21, No. 11, pp. 1758-1768.
Klingemann, Hans "Cellular therapy of cancer with natural killer cells-where do we stand?", Cytotherapy, vol. 15, No. 10, Oct. 1, 2013 (Oct. 1, 2013), pp. 1185-1194.
Lee et al: "Expansion of cytotoxic natural killer cells using irradiated autologous peripheral blood mononuclear cells and anti-CD16 antibody", Scientific Reports, 7: 11075.
Leong et al. "Preactivation with IL-12, IL-15, and IL-18 Induces CD25 and a Functional High-Affinity IL-2 Receptor on Human Cytokine-Induced Memory-like Natural Killer Cells" Biol Blood Marrow Transplant, Apr. 2014, vol. 20, No. 4, pp. 463-473.
Liu, E. et al: "Cord blood NK cells engineered to express IL-15 and a CD19-targeted CAR show long-term persistence and potent antitumor activity", Leukemia, vol. 32, No. 2, Jul. 20, 2017 (Jul. 20, 2017), pp. 520-531.
Martins et al. "Towards an advanced therapy medicinal product based on mesenchymal stromal cells isolated from the umbilical cord tissue: quality and safety data", Stem Cell Res Ther, Jan. 17, 2014, vol. 5, article 9, pp. 1-15.
Meyer et al: "Isolation and characterisation of mesenchymal stem cells in Wharton's jelly of the human umbilical cord: potent cells for cell-based therapies in paediatric surgery?" Eur Surg (2008) 40/5: 239-244.
Pelekanos et al., "Isolation and Expansion of Mesenchymal Stem/Stromal Cells Derived from Human Placenta Tissue", J. Vis. Exp. Jun. 2016 | 112 | e54204.
Polchert et al., "IFN-? activation of mesenchymal stem cells for treatment and prevention of graft versus host disease", Eur J Immunol., Jun. 2008; 38(6): 1745-1755.
Rezvani et al: "Engineering Natural Killer Cells for Cancer Immunotherapy", A Molecular Therapy : The Journal of the American Society of Gene Therapy, vol. 25, No. 8, Aug. 1, 2017 (Aug. 1, 2017), pp. 1769-1781.
Sarvaria et al: "Umbilical Cord Blood Natural Killer Cells, Their Characteristics, and Potential Clinical Applications", Frontiers in Immunology, vol. 8, Mar. 23, 2017 (Mar. 23, 2017), pp. 1-6.
Shah et al: "Antigen Presenting Cell-Mediated Expansion of Human Umbilical Cord Blood Yields Log-Scale Expansion of Natural Killer Cells with Anti-Myeloma Activity", Plos One, vol. 8, No. 10, Oct. 18, 2013 (Oct. 18, 2013), p. e76781.
Shah, Nina: "Ex Vivo Expanded Cord Blood Natural Killer Cells as a Novel Therapeutic for Multiple Myeloma", Texas Mediacl Center Library: Dissertations and Theses, Aug. 1, 2015 (Aug. 1, 2015), pp. 1-47.
Sivanathan et al: "Transcriptome Profiling of IL-17A Preactivated Mesenchymal Stem Cells: A Comparative Study to Unmodified and IFN-γ Modified Mesenchymal Stem Cells", Stem Cells International, vol. 2017, Article ID 1025820, 16 pages, https://doi.org/10.1155/2017/1025820.
Webb et al., "Ex vivo induction and expansion of Natural Killer T cells by CD1d1-Ig coated artificial antigen presenting cells" Journal of Immunological Methods, 2009, vol. 346, No. 1-2, pp. 38-44.
Liu et al. "Manufacture of Clinical-Grade Universal Antigen Presenting Cells (UAPC) for the Ex Vivo Expansion and Activation of Natural Killer (NK) Cells," Blood, Nov. 21, 2018 (Nov. 21, 2018), vol. 132, Suppl 1, p. 2061.
Kis-Toth et al. "Engagement of SLAMF2/CD48 prolongs the time frame of effective T cell activation by supporting nature dendritic cell survival," J Immunol, Mar. 26, 2014 (Mar. 26, 2014), vol. 192, pp. 4436 4442.
Agrawal et al., "14G2a anti-GD2 crossreactivity with the CD166 antigen," J Immunother., 33(9):1014-1015, 2010.
Baev et al., "Distinct homeostatic requirements of CD4+ and CD4− subsets of Va24− invariant natural killer T cells in humans," Blood, 104(13):4150-4156, 2004.
Batra et al., "Armored Glypican-3-Specific CAR T Cells for the Immunotherapy of Hepatocellular Carcinoma," Molecular Therapy, 26(5), Suppl. 1, p. 441, 2018.
Bendelac et al., "CD1 Recognition by Mouse NK1+ T Lymphosytes," Science, 268: 863-865, 1995.
Bendelac et al., "The Biology of NKT Cells," Annu. Rev. Immunol., 25:297-336, 2007.
Brocker and Karjalainen, "Signals through T Cell Receptor-z Chain Alone Are Insufficient to Prime Resting T Lymphocytes," J. Exp. Med., 181:1653-1659, 1995.
Brudno et al., "Toxicities of Chimeric antigen Receptor T Cells: Recognition and Management," Blood, 127(26): 3321-3330, 2016.
Cartellieri et al., "Chimeric Antigen Receptor-Engineered T Cells for Immunotherapy of Cancer," Journal of Biomedicine and Biotechnology, 2010:956304, 13 pages, 2010.
Chan et al., "Immunohistochemical Expression of Glypican-3 in Pediatric Tumors: An Analysis of 414 Cases," Pediatric and Developmental Pathology, 16:272-277, 2013.
Chang et al., "Sustained expansion of NKT cells and antigen-specific T cells after injection of a-galactosyl-ceramide loaded mature dendritic cells in cancer patients," J. Exp. Med., 201(9):1503-1517, 2005.
Cheresh et al., "Biosynthesis and Expression of the Disialoganglioside GD2, a Relevant Target Antigen on Small Cell Lung Carcinoma for Monoclonal Antibody-mediated Cytolysis1," Cancer Research, 46:5112-5118, 1986.
Cohen et al., "Shared and distinct transcriptional programs underlie the hybrid nature of iNKT cells," Nat Immunol., 14(1):90-99, 2013.
Crowe et al., "Differential antitumor immunity mediated by NKT cell subsets in vivo," J. Exp. Med., 202(9):1279-1288, 2005.
Delconte et al. "NK Cell Priming From Endogenous Homeostatic Signals Is Modulated by CIS,". Front Immunol., 11(75), 16 pages, 2020.
Delconte et al., "CIS is a potent checkpoint in NK cell-mediated tumor immunity," Nature Immunology, 17:816-824, 2016.
Dhodapkar, "Harnessing human CD1d restricted T cells for tumor immunity: progress and challenges," Front Biosci., 14:796-807, 2009.
Di Stasi et al., "Inducible Apoptosis as a Safety Switch for Adoptive Cell Therapy," N. Engl. J. Med., 365:1673-1683, 2011.

(56) References Cited

OTHER PUBLICATIONS

Dotti et al., "Design and development of therapies using chimeric antigen receptorexpressing T cells," Immunol Rev., 257(1):107-126, 2014.
Dotti et al., "Fifteen Years of Gene Therapy Based on Chimeric Antigen Receptors: "Are We Nearly There Yet?"", Human Gene Therapy, 20:1229-1239, 2009.
Einsele, "Immunotherapy and cellular therapy," COMy Announcement, Multiple Myeloma 2017 highlights: A post International Myeloma Workshop (IMW) summary, Paris, France, 61 pages, Apr. 21-22, 2017.
English translation of Office Action issued in Japanese Patent Application No. 2019-556918, dated May 25, 2022.
English translation of Office Communication issued in Eurasian Patent Application No. 202092588, dated Mar. 21, 2023.
English translation of Office Communication issued in Japanese Patent Application No. 2020-561821, dated May 9, 2023.
Exley et al., "Selective activation, expansion, and monitoring of human iNKT cells with a monoclonal antibody specific for the TCR a-chain CDR3 loop," Eur. J. Immunol., 38:1756-1766, 2008.
Extended European Search Report issued in European Patent Application No. 20782753.6, dated Dec. 5, 2022.
Fehniger et al., "Fatal Leukemia in Interleukin 15 Transgenic Mice Follows Early Expansions in Natural Killer and Memory Phenotype CD8+ T Cells," J. Exp. Med., 193(2):219-231, 2001.
Furukawa et al., "Biosignals Modulated by Tumor-Associated Carbohydrate Antigens," Ann. N.Y. Acad. Sci., 1086:185-198, 2006.
Gan et al., "The epidermal growth factor receptor variant III (EGFRvlll): where wild things are altered," The FEBS Journal, 280(21):5350-5370, 2013.
Gao et al., "Development of T Cells Redirected to Glypican-3 for the Treatment of Hepatocellular Carcinoma," Clinical Cancer Research, 20(24):6418-6428, 2014.
Gao et al., "Supplementary Data: Development of T Cells Redirected to Glypican-3 for the Treatment of Hepatocellular Carcinoma," Clinical Cancer Research, Figures Only, pp. 6418-6642, retrieved from Internet: http://clincancerres.aacrjournals.org/content/20/24/6418, 2014.
Godfrey and Kronenberg, "Going both ways: immune regulation via CD1d-dependent NKT cells," Journal of Clinical Investigation, 114(10): 379-1388, 2004.
Godfrey et al., "NTK cells: what's in a name?" Nature Reviews Immunology; Nature Publishing Group; 4:231-237, 2004.
Godfrey et al., "Raising the NKT cell family," Nat Rev Immun, 11(3):197-206, 2010.
Graef et al., "Serial transfer of single-cell-derived immunocompetence reveals sternness of CDS(+)central memory T cells," Immunity, 41(1)116-126, 2014.
Guillerey et al. "Targeting natural killer cells in cancer immunotherapy," Nature Immulogy, 17(9):1025-1036, 2016.
Guittard et al. "The Cish SH2 domain is essential for PLC-γ1 regulation in TCR stimulated CD8 30 T cells," Sci Rep., 8(1):5336, 2018.
Heczey et al., "Invariant NKT cells with chimeric antigen receptor provide a novel platform for safe and effective cancer immunotherapy," Blood, 124(18):2824-2833, 2014.
Heczey et al., "NKT cells as a novel platform for cancer immunotherapy with chimeric antigen receptors (P2038)," The Journal of Immunol., 190:132.9, 1 page, 2013.
Hofflin et al. "Generation of COB+ T cells expressing two additional T-cell receptors (TETARs) for personalised melanoma therapy," Cancer Biology & Therapy, 16(9):1323-1331, 2015.
Hsu et al., "Cytokine-independent growth and clonal expansion of a primary human CD8+ T-cell clone following retroviral transduction with the IL-15 gene," Blood, 109(12):5168-5177, 2007.
Huang et al., "Interleukin-armed chimeric antigen receptor-modified T cells for cancer immunotherapy," Gene Therapy, 25(3):192-197, 2017.
Imai et al., "Complement-Mediated Mechanisms in Anti-GD2 Monoclonal Antibody Therapy for Murine Metastatic Cancer," American Association for Cancer Research, 10562-10568, 2005.
International Search Report and Written Opinion issued in Application No. PCT/US16/28693, mailed Jul. 21, 2016.
International Search Report and Written Opinion issued in International Patent Application No. PCT/US2019/030721, dated Aug. 22, 2019.
Ishikawa et al., "A Phase I Study of a-Galactosylceramide (KRN7000)-Pulsed Dendritic Cells in Patients with Advanced and Recurrent Non-Small Cell Lung Cancer," Clin. Cancer Res., 11:1910-1917, 2005.
Johnson et al., "Rational development and characterization of humanized anti-EGFR variant III chimeric antigen receptor T cells for glioblastoma," Science Translational Medicine, 7(275):192-197, 2015.
Kalos et al., "Adoptive T cell transfer for cancer immunotherapy in the era of synthetic biology," Immunity, 39(1):49-60, 2013.
Kambayashi et al., "Emergence of D8+ T Cells Expressing NI Cell Receptors in Influenza A virus-infected mice," The Journal of Immunology; 165:4964-4969, 2000.
Kershaw et al., "A Phase I Study on Adoptive Immunotherapy Using Gene-Modified T cells for Ovarian Cancer," Clin. Cancer Res., 12:6106-6115, 2006.
Khor et al., "CISH and Susceptibility to Infectious Diseases," New England Journal of Medicine, 362(22):2092-2101, 2010.
Kim et al., "4-1BB Engagement Costimulates NKT Cell Activation and Exacerbates NKT Cell Ligand-Induced Airway Hyperresponsiveness and Inflammation," J. Immunol., 180:2062-2068, 2008.
Kronenberg et al., "The unconventional lifestyle of NKT cells," Nat. Rev. Immunol., 2:557-568, 2002.
Kunii et al., "Combination therapy of in vitro-expanded natural killer T cells and a-galactosylceramide-pulsed antigen-presenting cells in patients with recurrent head and neck carcinoma," Cancer Sci., 100(6):1092-1098, 2009.
Lantz et al., "An Invariant T Cell Receptor a Chain Is Used by a Unique Subset of Major Histocompatibility Complex Class I-specific CD4+ and CD4-8− T Cells in Mice and Himans," J. Exp. Med., 180:1097-1106, 1994.
Lappas et al., "Adenosine A2A receptor activation reduces hepatic ischemia reperfusion injury by inhibiting CD1d-dependent NKT cell activation," J. Experimental Medicine, 203(12):2639-2648, 2006.
Levy et al., "Expression of glypican-3 in undifferentiated embryonal sarcoma and mesenchymal hamartoma of the liver," Human Pathology, 43:695-791, 2012.
Li et al., "Immunotherapy of Hepatocellular Carcinoma with T Cells Engineered To Express Glypican-3-Specific Chimeric Antigen Receptors," Molecular Therapy, 23(Suppl. I): SI64-SI65.; and 18th Annual Meeting of the American-Society-of-Gene-and-Cell-Therapy (ASGCT); New Orleans, LA, USA; May 13-16, 2015.
Li et al., "In vitro validation of human glypican-3 specific chimeric antigen receptors for hepatocellular carcinoma," Hepatology, 60(Suppl. 1): Sp. Iss. SI, Oct. 2014, p. 870A, XP002780485; and 65th Annual Meeting of the American-Association-for-the-Study-of-Liver-Diseases; Boston, MA, USA; Nov. 7-11, 2014.
Li et al., "NKT Cell Activation Mediates Neutrophil IFN-γ Production and Renal Ischemia-Reperfusion Injury," The Journal of Immunology, 178:5899-5911, 2007.
Li et al., "Validation of glypican-3-specific scFv isolated from paired display/secretory yeast display library," BMC Biotechnology, 12(1):23, 2012.
Liu et al., "IL-15 protects NKT cells from inhibition by tumor-associated macrophages and enhances antimetastatic activity," The Journal of Clinical Investigation, 122(6):2221-2233, 2012.
Lo et al., "Anti-GD3 chimeric sFv-CD28/T-cell receptor zeta designer T cells for treatment of metastatic melanoma and other neuroectodermal tumors," Cancer Res., 16(10):2769-2780, 2010.
Louis et al., "NK cell-derived GM-CSF potentiates inflammatory arthritis and is negatively regulated by CIS." J Exp Med., 217(5): e20191421, 2020.

(56) References Cited

OTHER PUBLICATIONS

Louis et al., "Treatment of High-Risk Neuroblastoma with Adoptively Transferred T Lymphocytes Genetically Engineered to Recognize GD2," Biology of Blood and Marrow Transplantation, 15(2):26, 2009.
Macdonald, "Nkt cells: In the Beginning . . . ," Eur. J. Immunol., 37:S111-115, 2007.
Maher et al., "Human T-lymphocyte cytotoxicity and proliferation directed by a single chimeric TCRz/CD28 receptor," Nat. Biotechol., 20:70-75, 2002.
Male et al., In: Immunology, Seventh Edition. Canada: Elsevier Limited, pp. 11 and 527, published 2007.
Mantovani et al., "Cancer-related inflammation," Nature, 454:24:436-444, 2008.
Matsuda et al., "Homeostasis of V alpha 14i NKT cells," Nat. Immunol., 3(10):966-974, 2002.
Menger et al., "TALEN-mediated genetic inactivation of the glucocorticoid receptor in cytomegalovirus-specific T cells," Blood, 126(26):2781-2789, 2015.
Metelitsa et al., "Human NKT Cells Mediate Antitumor Cytotoxicity Directly by Recognizing Target Cell CD1d with Bound Ligand or Indirectly by Producing IL-2 to Activate NK Cells," Journal of Immunology, 167:3114-3122; 2001.
Metelitsa et al., "Natural Killer T Cells Infiltrate Neuroblastomas Expressing the Chemokine CCL2," J. Exp. Med., 199(9):1213-1221, 2004.
Metelitsa, "Anti-tumor potential of type-I NKT cells against CD1d-positive and CD1d-negative tumors in humans," Clinical Immunology, 140:119-129, 2011.
Molling et al., "Low Levels of Circulating Invariant Natural Killer T Cells Predict Poor Clinical Outcome in Patients with Head and Neck Squamous Cell Carcinoma," J. Clin. Oncol., 25(7):862-868, 2007.
Motohashi et al., "A Phase I-II Study of a-Galactosylceramide-Pulsed IL-2/GM-CSF-Cultured Peripheral Blood Mononuclear Cells in Patients with Advanced and Recurrent Non-Small Cell Lung Cancer," J. Immunol., 182:2492-2501, 2009.
Mujoo et al., "Functional Properties and Effect on Growth Suppression of Human Neuroblastoma Tumors by Isotype Switch Variants of Monoclonal Antiganglioside GD2," American Association for Cancer Research, 49(11):2857-2861, 1989.
Nandagopal et al., "The critical role of IL-15-PI3K-mTOR pathway in natural killer cell effector functions," Frontiers in Immunology, 5(187), pp. 1-12, 2014.
Navid et al., "Anti-GD2 antibody therapy for GD2-expressing tumors," Curr. Cancer Drug Target, 10(2):200-209, 2010.
Nguyen et al., "Glypican-3-Specific Car Nkt Cells Armored with IL-15 Exhibit Potent and Sustained Anti-Tumor Activity against Hepatocellular Carcinoma," Molecular Therapy, 26(5), Suppl. 1, p. 62, 2018.
Nieda et al., "Therapeutic activation of Va24+Vb11+ NKT cells in human subjects results in highly coordinated secondary activation of acquired and innate immunity," Blood, 103(2):383-389, 2004.
Office Communication issued in European Patent Application No. 18787208.0, dated May 23, 2023.
Office Communication issued in Singapore Patent Application No. 11202010763V, dated Jul. 4, 2022.
Palmer et al., "Cish actively silences TCR signaling in CD8+ T cells to maintain tumor tolerance." J. Exp. Med., 212(12):2095-2113, 2015.
Peralbo et al., "Invariant NKT and NKT-like lymphocytes: Two different T cell subsets that are differentially affected by ageing," Experimental Gerontology, 42(8):703-8, 2007.
Porcelli et al., "Analysis of T Cell Antigen Receptor (TCR) Expression by Human Peripheral Blood CD4-8– a/b T Cell Demonstrates Preferential Use of Several Vb genes and an Invariant TCR a Chain," J. Exp. Med., 178, pp. 1-16, 1993.
Porter et al., "Chimeric Antigen Receptor-Modified T Cells in Chronic Lymphoid Leukemia," N. Engl. J. Med., 365(8):725-733, 2011.
Pule et al., "A Chimeric T Cell Antigen Receptor That Augments Cytokine Release and Supports Clonal Expansion of Primary Human T Cells," Molecular Therapy, 12:933-941, 2005.
Pule et al., "Virus-specific T cells engineered to coexpress tumor-specific receptors: persistence and antitumor activity in individuals with neuroblastoma," Nat. Med., 14(11):1264-1270, 2008.
Putz et al., "Targeting cytokine signaling checkpoint CIS NK cells to protect from tumor initiation and metastasis," Oncoimmunology, 6(2), pp. 1-10, 2017.
Qian et al., "The novel anti-CD19 chimeric antigen receptors with humanized scFv (single-chain variable fragment) trigger leukemia cell killing," Cellular Immunology, 304:49-54, 2016.
Quintarelli et al., "Co-expression of sytokine and suicide genes to enhance the activity and safety of tumor-specific cytotoxic T lymphosytes," Blood, 110(8):2793-2802, 2007.
Rautela et al., "Drug target validation in primary human natural killer cells using CRISPR RNP," J. Leukoc. Biol., 108(4):13971408, 2020.
Ren et al., "A versatile system of rapid multiplex genome-edited CAR T cell generation," Oncotarget, 8(10):17002-17011, 2017.
Ren et al., "Advancing chimeric antigen receptor T cell therapy with CRISPR/Cas9," Protein Cell, 8(9):634-643, 2017.
Rettig et al., "Transduction and Selection of Human T Cells with Novel CD34/Thymidine Kinase Chimeric Suicide Genes for the Treatment of Graft-versus-Host Disease," Molecular Ther., 8(1):29-41, 2003.
Riedl et al., "The apoptosome: signalling platform of cell death," Nat. Rev. Mol. Cell Biol., 8:405-413, 2007.
Rossig et al., "Targeting of GD2-Positive Tumor Cells by Human T Lymphocytes Engineered to Express Chimeric T-Cell Receptor Genes," Int. J. Cancer, 94:228-236, 2001.
Rossig et al., "Epstein-Barr virus-specific human T lymphocytes expressing antitumer chimeric T-cell receptors: potential for improved immunotherapy," Blood, 99(6):2009-2016, 2002.
Rossjohn et al., "Recognition of CD1d-restricted antigens by natural killer T cells," Nat. Rev. Immunol., 12(12):845-857, 2012.
Sadelain et al., "The promise and potential pitfalls of chimeric antigen receptors," Current Opinion in Immunology, 21:215-223, 2009.
Sahm et al., "Expression of IL-15 in NK cells results in rapid enrichment and selective cytotoxicity of gene-modified effectors that carry a tumor-specific antigen receptor," Cancer Immunology Immunotherapy, 61:1451-1461, 2012.
Sato et al., "Development of an IL-15—autocrine CD8 T-cell leukemia in IL-15—transgenic mice requires the cis expression of IL-15Ra," Blood, 117:4032-4040, 2011.
Savoldo et al., "CD28 costimulation improves expansion and persistence of chimeric antigen receptor-modified T cells in lymphoma patients," J. Clin. Invest., 112(5):1822-1826, 2011.
Shah, "T-Cell Development in Thymus," British Society for Immunology, London, retrieved from the Internet: www.immunology.org/public-information/bitesized-immunology/immune-development/t-cell-development-thymus, retrieved on Sep. 16, 2008.
Sica and Bronte, "Altered macrophage differentiation and immune dysfunction in tumor development," J. Clin. Invest., 117(5):1155-1166, 2007.
Sica et al., "Macrophage polarization in tumour progression," Seminars in Cancer Biology, 18:349-355, 2008.
Slifka et al., "NK Markers are Expressed on a High Percentage of Virus-Specific CD8+ and CD4+ T Cells," J. Immunol., 164:209-2015, 2000.
Sommermeyer et al., "Chimeric antigen receptor-modified T cells derived from defined COB and CD4 subsets confer superior anti-tumor reactivity in vivo," Leukemia, 30(2):492-500, 2015.
Song et al., "In Vivo Persistence, Tumor Localization, and Antitumor Activity of CAR-Engineered T Cells Is Enhanced by Costimulatory Signaling through CD137 (4-1 BB)," Cancer Research, 71(13):4617-4627, 2011.
Song et al., "Va24-invariant NKT cells mediate antitumor activity via killing of tumor-associated macrophages," J. Clin. Invest., 119(6):1524-1536, 2009.
Straathof et al., "An inducible caspase 9 safety switch for T-cell therapy," Blood, 105(11):4247-4254, 2005.

(56) References Cited

OTHER PUBLICATIONS

Supplementary European Search Report dated Jan. 21, 2022 issued in European Patent Application No. 19795874.7.
Suzukil et al., "Glypian-3 (GPC3) as a novel tumor for malignant ovarian tumors and malignant melanoma," Japan Molecular Tumor Markers Research Journal, 25:31-32, 2010. (English abstract).
Swann et al., "CD1-Restricted T Cells and Tumor Immunity," Curr. Top. Microbiol. Immunol., 314:293-321, 2007.
Tachibana et al., "Increased Intratumor Va24-Positive Natural Killer T Cells: A Prognostic Factor for Primary Colorectal Carcinomas," Clin. Cancer Res., 11(20):7322-7327, 2005.
Takahashi et al., "Cutting edge: analysis of human V alpha 24+CD8+ NK T cells activated by alpha-galactosylceramide-pulsed monocyte-derived dendritic cells;" The Journal of Immunology; 168(7):3140-3144, 2002.
Tey et al., "Inducible caspase 9 suicide gene to improve the safety of allodepleted T cells after haploidentical stem cell transplantation," Biol. Blood Marrow Transplant., 13(8):913-924, 2007.
Till et al., "Adoptive immunotherapy for indolent non-Hodgkin lymphoma and mantle cell lymphoma using genetically modified autologous CD20-specific T cells," Blood, 112(6):2261-2271, 2008.
Toretsky et al., "Glypican-3 Expression in Wilms Tumor and Hepatoblastoma," Journal of Pediatric Hematology/Onocolgy, 23(8):496-499, 2001.
Torikai et al., "Translational Implications for Off-the-shelf Immune Cells Expressing Chimeric Antigen Receptors," Molecular Therapy, 24(7):1178-1186, 2016.
Uldrich et al., "NKT cell stimulation with glycolipid antigen in vivo: co-stimulation-dependent expansion, Bim-dependent contraction, and hypo-responsiveness to further antigenic challenge," J. Immunol., 175(5):3092-3101, 2005.
Veluchamy et al., "The Rise of Allogeneic Natural Killer Cells as a Platform for Cancer Immunotherapy: Recent Innovations and Future Developments." Frontiers in Immunology, 8(631), pp. 1-20, 2017.
Vera et al., "591. Large Scale Production of Suspension Cells for Clinical Application Using a Novel Cell Bioreactor," Molecular Therapy, 19(Suppl. 1):S226, 2011.
Vera et al., "Accelerated production of antigen-specific T cells for preclinical and clinical applications using gas-permeable rapid expansion cultureware (G-Rex)," 33(3):305-315, 2010.
Vinay et al., "CD137-Deficient Mice Have Reduced NK/NKT Cell Numbers and Function, Are Resistant to Lipopolysaccharide-Induced Shock Syndromes, and Have Lower IL-4 Responses," J. Immunol., 173:4218-4229, 2004.
Wang et al., "A transgene-encoded surface polypeptide for selection, in vivo tracking, and ablation of engineerred A cells," Blood, 118(5):1255-1263, 2011.
Wang et al., "Phenotypic and functional attributes of lentivirus-modified CD19-specific human COB+central memory T cells manufactured at clinical scale," J. Immunother., 35(9):689-701, 2012.
Wang et al., "Tumor-derived soluble MICs impair CD3+CD56+ NKT-like cell cytotoxicity in cancer patients;" Elsevier Immunology Letters, 120(1-2):65-71, 2008.
Wilkie et al., "Retargeting of Human T Cells to Tumor-Associated MUC1: The Evolution of a Chimeric Antigen Receptor," J. Immunol., 180:4901-4909, 2008.
Xu and Dotti, "Selection bias: maintaining less-differentiated T cells for adoptive immunotherapy," J. Clinical Invest., 126(1):35-37, 2016.
Yoshida et al., "Ganglioside G(D2) in Small Cell Lung Cancer Cell Lines: Enhancement of Cell Proliferation and Mediation of Apoptosis," Cancer Research, 61(10):4244-4252, 2001.
Yvon et al., "Immunotherapy of Metastatic Melanoma Using Genetically Engineered GD3-Specific T cells," Clinical Cancer Research, 15(18):5852-5860, 2009.
Zaini et al., "OX40 ligand expressed by DCs costimulates NKT and CD4+ Th cell antitumor immunity in mice," J. Clin. Invest., 117(11):3330-3338, 2007.
Zhao et al., "GS2 Oligosaccharide: Target for Cytotoxic T Lymphocytes" The Journal of Experimental Medicine, 182:67-74, 1995.
Zhu et al. "Metabolic Reprograming via Deletion of CISH in Human iPSC-Derived NK Cells Promotes In Vivo Persistence and Enhances Anti-tumor Activity," Cell Stem Cell, 27(2):224-237.e6, 2020.
Zou et al., "Immunosuppressive networks in the tumour environment and their therapeutic relevance," Nat. Rev. Cancer, 5:263-274, 2005.

* cited by examiner

| fold NK increase | absolute NK produced (x 10e6) | absolute CD3 (x 10e6) |
|---|---|---|
| 4093 | 1471 | 4.50 |

K562 UNIVERSAL ANTIGEN PRESENTING CELLS AND USES THEREOF

This application is a national phase application under 35 U.S.C. § 371 that claims priority to International Application No. PCT/US2019/018989 filed Feb. 21, 2019, which claims the benefit of U.S. Provisional Application No. 62/633,587 filed Feb. 21, 2018, all of which are incorporated herein by reference in their entirety.

INCORPORATION OF SEQUENCE LISTING

The instant application contains a Sequence Listing, named "SL_UTSC_P1182US.txt" (21,739 bytes) which has been submitted electronically in ASCII format and is hereby incorporated by reference in its entirety.

BACKGROUND

The sequence listing that is contained in the file named "UTFCP1355WO_ST25.txt", which is KB (as measured in Microsoft Windows) and was created on Feb. 21, 2019, is filed herewith by electronic submission and is incorporated by reference herein

1. Field

The present invention relates generally to the fields of medicine and immunology. More particularly, it concerns antigen presenting cells and uses thereof, such as expanding natural killer (NK) cells.

2. Description of Related Art

Natural killer (NK) cells do not need previous exposure to antigens for activation which is in contrast to T cells, making them highly effective in immuno-surveillance against tumors. While prior activation is not required, the immense killing powers of NK cells need stringent controls to forestall unintended cytotoxicity and autoimmunity. Generation of clinically sufficient quantities and optimally functional NK cells is another impediment. Thus, there is a need to focus on the molecular machinery governing NK cell biology to discriminate "resistant" from "sensitive" target cells to design helper cells to enhance NK-cell mediated cancer immunotherapy.

SUMMARY

Accordingly, certain embodiments of the present disclosure provide methods and compositions concerning the manufacture, expansion, quality control, and functional characterization of clinical-grade NK cells intended for cell and immunotherapy.

In a first embodiment, there is provided a universal antigen presenting cell (UAPC) engineered to express (1) CD48 and/or CS1 (CD319), (2) membrane-bound interleukin-21 (mbIL-21), and (3) 41BB ligand (41BBL). In some aspects, the UAPC expresses CD48. In other aspects, the UAPC expresses CS1. In particular aspects, the UAPC expresses CD48 and CS1.

In some aspects, the UAPC has essentially no expression of endogenous HLA class I, II, or CD1d molecules. In certain aspects, the UAPC expresses ICAM-1 (CD54) and LFA-3 (CD58).

In certain aspects, the UAPC is further defined as a leukemia cell-derived aAPC. In some aspects, the leukemia-cell derived UAPC is further defined as a K562 cell.

In some aspects, engineered is further defined as retroviral transduction. In some aspects, the retroviral transduction is further defined as transduction of a viral construct of SEQ ID NO:1 and/or SEQ ID NO:2. In certain aspects, the UAPC is irradiated.

In a further embodiment, there is provided a method for expanding immune cells comprising culturing the immune cells in the presence of an effective amount of UAPCs of the embodiments (e.g., a universal antigen presenting cell (UAPC) engineered to express (1) CD48 and/or CS1 (CD319), (2) membrane-bound interleukin-21 (mbIL-21), and (3) 41BB ligand (41BBL)). In some aspects, the immune cells and UAPCs are cultured at a ratio of 3:1 to 1:3, such as 3:1, 3:2, 1:1, 1:2, or 1:3. In particular aspects, the immune cells and UAPCs are cultured at a ratio of 1:2.

In some aspects, the expanding is in the presence of IL-2. In specific aspects, the IL-2 is present at a concentration of 10-500 U/mL, such as 10-25, 25-50, 50-75, 75-10, 100-150, 150-200, 200-250, 250-300, 300-350, 350-400, or 400-500 U/mL. In certain aspects, the IL-2 is present at a concentration of 100-300 U/mL. In particular aspects, the IL-2 is present at a concentration of 200 U/mL. In some aspects, the IL-2 is recombinant human IL-2. In specific aspects, the IL-2 is replenished every 2-3 days, such as every 2 days or 3 days.

In certain aspects, the UAPCs are added at least a second time. In some aspects, the immune cells are NK cells or T cells. In particular aspects, the immune cells are NK cells.

In particular aspects, the immune cells are derived from cord blood (CB), peripheral blood (PB), stem cells, or bone marrow. In specific aspects, the stem cells are induced pluripotent stem cells. In some aspects, the immune cells are obtained from CB. In particular aspects, the CB is pooled from 2 or more individual cord blood units. In specific aspects, the CB is pooled from 3, 4, 5, 6, 7, or 8 individual cord blood units.

In some aspects, the NK cells are CB mononuclear cells (CBMCs). In certain aspects, the NK cells are further defined as $CD56^+$ NK cells.

In certain aspects, the method is performed in serum-free media.

In additional aspects, the immune cells are engineered to express a chimeric antigen receptor (CAR). In some aspects, the CAR comprises a CD19, CD123, mesothelin, CD5, CD47, CLL-1, CD33, CD99, U5snRNP200, CD200, CS1, BAFF-R, ROR-1, or BCMA antigen-binding domain. In some aspects, the CAR is a humanized CAR. In some aspects, the CAR is co-expressed with IL-15. In certain aspects, the CAR is co-expressed with a suicide gene. In some aspects, the suicide gene is CD20, CD52, EGFRv3, or inducible caspase 9.

Further provided herein is a population of expanded immune cells produced according to the embodiments (e.g., culturing the immune cells in the presence of an effective amount of UAPCs of the embodiments (e.g., a universal antigen presenting cell (UAPC) engineered to express (1) CD48 and/or CS1 (CD319), (2) membrane-bound interleukin-21 (mbIL-21), and (3) 41BB ligand (41BBL)).

In another embodiment, there is provided a pharmaceutical composition comprising the population of expanded immune cells of the embodiments and a pharmaceutically acceptable carrier. Further provided herein is a composition comprising an effective amount of the expanded immune cells of the embodiments for use in the treatment of a disease or disorder in a subject.

A further embodiment provides a method of treating a disease or disorder in a subject comprising administering a therapeutically effective amount of the expanded immune cells of the embodiments to the subject.

In some aspects, the disease or disorder is cancer, inflammation, graft versus host disease, transplant rejection, an autoimmune disorder, an immunodeficiency disease, a B cell malignancy, or an infection. In particular aspects, the cancer is a leukemia. In some aspects, the leukemia is an acute lymphoblastic leukemia (ALL), chronic lymphocytic leukemia (CLL), acute myelogenous leukemia (AML), or a chronic myelogenous leukemia (CIVIL). In particular aspects, the disorder is graft versus host disease (GVHD). In some aspects, the disorder is multiple sclerosis, inflammatory bowel disease, rheumatoid arthritis, type I diabetes, systemic lupus erythrematosus, contact hypersensitivity, asthma or Sjogren's syndrome. In some aspects, the subject is a human.

In certain aspects, the immune cells are allogeneic. In some aspects, the immune cells are autologous. In some aspects, the immune cells are NK cells or T cells.

In additional aspects, the method further comprises administering at least a second therapeutic agent. In some aspects, the at least a second therapeutic agent is a therapeutically effective amount of an anti-cancer agent, immunomodulatory agent, or an immunosuppressive agent. In certain aspects, the anti-cancer agent is chemotherapy, radiotherapy, gene therapy, surgery, hormonal therapy, anti-angiogenic therapy or immunotherapy.

In some aspects, the immunosuppressive agent is a calcineurin inhibitor, an mTOR inhibitor, an antibody, a chemotherapeutic agent irradiation, a chemokine, an interleukins or an inhibitor of a chemokine or an interleukin.

In further aspects, the immune cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion. In some aspects, the second therapeutic agent is an antibody. In certain aspects, the antibody if a monoclonal, bispecific, or trispecific antibody. In some aspects, the antibody is rituximab.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The present disclosure may be better understood by reference to one or more of these drawings in combination with the detailed description of specific embodiments presented herein.

(FIG. 2A-2B) Fold expansion of fresh or frozen NK cells with IL-2 or APCs. (FIG. 2C) Flow cytometry at Day 0, Day 7, or Day 14 for expression of CD3 and CD56 in NK cells. (FIG. 2D) Cell number of NT-NK or SG4-NK cells stimulated with APCs. (FIG. 2E) Growth kinetics of NK cells stimulated with Clone 9 APC or UAPC.

(FIG. 3A) Flow cytometry of parental K562 cells for indicated markers. No observed expression of mb-IL21, 41BBL, CD48, and SLAMF7 (CS1). (FIG. 3B) Flow cytometry analysis of APCs post-transduction of clone 46 (mbIL-21, 41BBL). (FIG. 3C) Flow cytometry analysis of APCs post-transduction of uAPC construct for expression of CD48 (nmIL-21, 41BBL, and CD48). (FIG. 3D) Flow cytometry analysis of APCs post-transduction of uAPC2 construct for expression of CS1 (mbIL-21, 41BBL, and CS1).

(FIG. 4A) Retroviral transfer vectors for mb-IL21. (FIG. 4B) Retroviral transfer vectors for 41BBL. (FIG. 4C) Retroviral transfer vectors for CD48-Katushka. (FIG. 4D) Retroviral transfer vectors for CS1-EGFP.

DESCRIPTION OF ILLUSTRATIVE EMBODIMENTS

Figure 1:
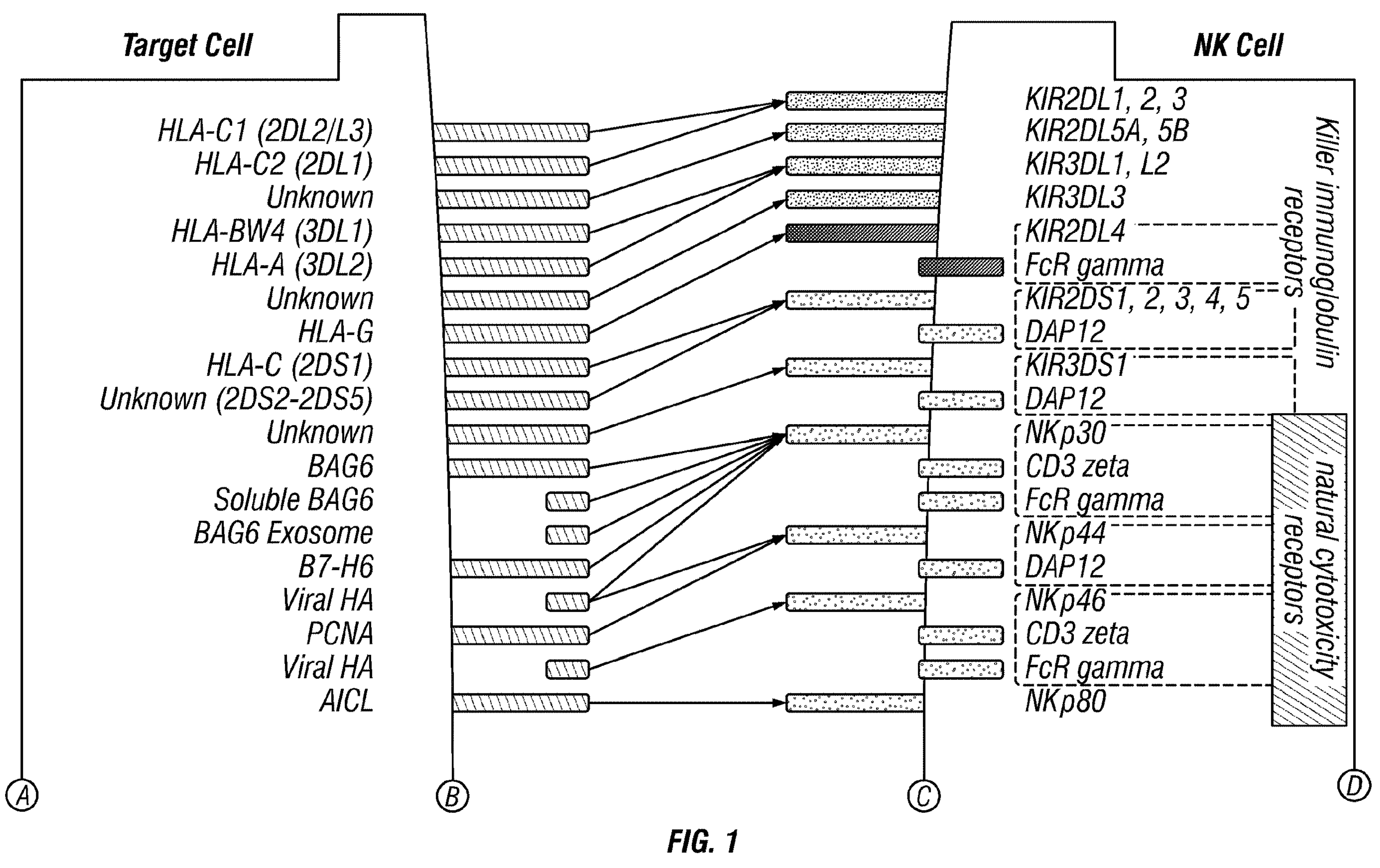
FIG. 1: Zipper model of human natural killer cell receptors and target cell ligand interactions. Human NK cells interact with target cells via many receptors, including killer immunoglobulin receptors (KIRs), natural cytotoxicity receptors (NCRs), NKG2 family of receptors, nectin binding receptors, SLAM family receptors and others. Receptors on NK cells are activating (KIR2DL4, KIR3DS1, NKp30, NKp44, NKp46, NKp80, CD94-NKG2C, DAP10, NKG2D, DAP10, CRTAM, DNAM, 2B4, NTB-A, CD3 zeta, CD100, CD160) or inhibitory (KIR2DL1/2/3/5A/5B, KIR3DL1/2/3, CD94-NKG2A, TIGIT, CD96, CEACAM-1, ILT2/LILRB1, KLRG1, LAIR1, CD161, Siglec-3/7/9)
Figure 1:
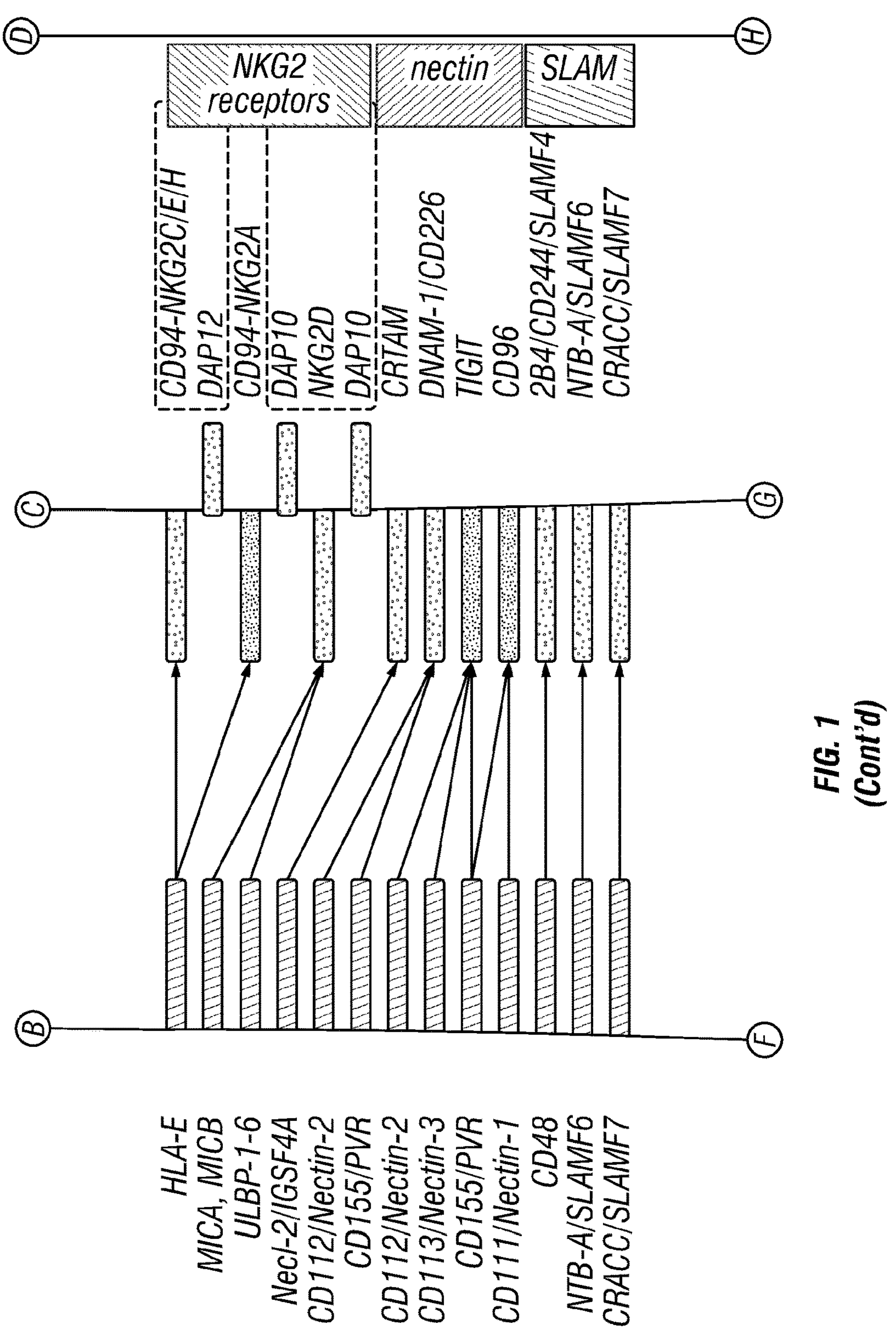
Figure 1:
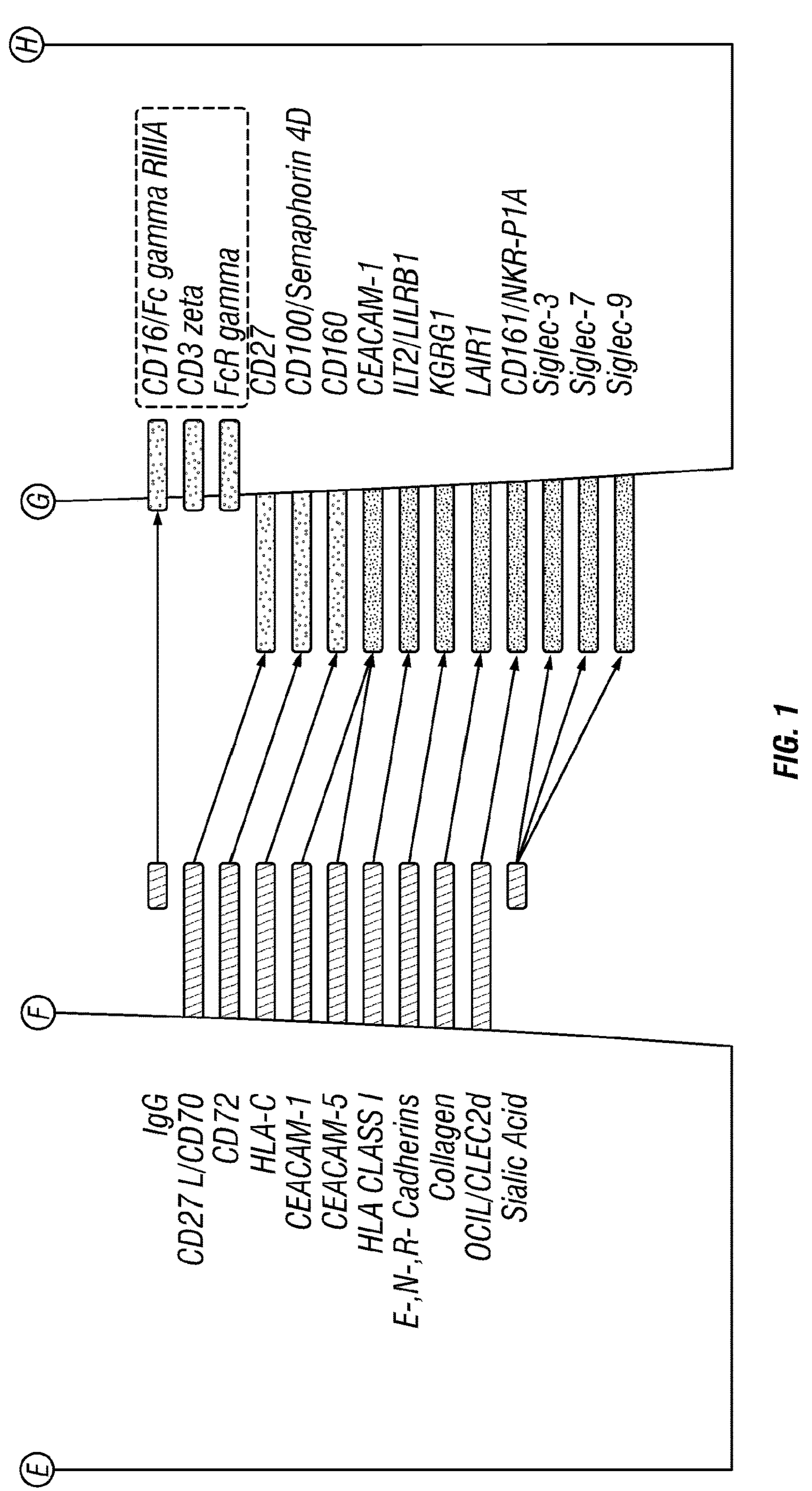

In the present studies, NK cells were initially characterized for their anti-tumoral and anti-allogeneic cytolytic functions, distinct from other components of the innate immunity compartment. A myriad of immunoreceptors governing the behaviors of NK cells are illustrated as a "zipper" graph in FIG. 1. The array of signal transducers can be broadly categorized into 2 large groups, namely activating versus inhibitory. Structural and signaling modalities further fractionate the categories into related families of immunoreceptors. Although the membrane proteome of NK cells has yet to be fully elucidated, the functional redundancies within the NK cell "zipper" were leveraged to modulate cytolytic functions while preserving the complex and dynamic balance between complementary and antagonistic pathways.

Accordingly, certain embodiments of the present disclosure provide methods and compositions concerning the manufacture, expansion, quality control, and functional characterization of clinical-grade NK cells intended for cell and immunotherapy. Growing and molding clinically relevant numbers of NK cells for infusion into patients while meeting time constraints are challenging even in the best of circumstances. In certain aspects, the disclosed methods and compositions detail the technical processes of NK cell manufacture, details and kinetics of achievable NK cell expansions, and molecular characterization to verify successful cellular molding.

In further embodiments, there is provided herein a robust platform technology embodied as universal antigen presenting cells (UAPC) to condition, mold, and weaponize human natural killer (NK) cells against tumors. "UAPC(s)" refer herein to antigen presenting cells designed for the optimized expansion of immune cells, such as NK cells. The present UAPCs were generated by a unique combination of co-stimulatory molecules to overcome inhibitory signals and induce optimal and specific NK cell killing function. Extensive testing showed UAPCs fine tunes NK cellular machinery and improved tumor elimination. The present UAPCs may be used for NK cell-mediated cancer immunotherapy.

Exemplary APCs are generated by enforced expression of membrane-bound interleukin 21 (mbIL-21) and 4-1BB ligand in the NK cell-sensitive K562 antigen-presenting cell line (APC) (referred to as clone 46). In another embodiment, UAPCs were produced by enforced expression of mbIL-21, 4-1BB ligand, and CD48 in K562 cells (termed universal APC (UAPC)). In another embodiment, UAPCs were generated by enforced expression of mbIL-21, 4-1BB ligand, and CS1 in K562 cells (termed UAPC2). The UAPCs may be generated to express mbIL-21, 41BBL, and an NK-cell specific antigen, such as a SLAM family antigen (Table 1).

The UAPC platform may also be applied to expand other immune effectors including T cells (e.g., alpha-beta and gamma-delta T cells). The immune cells, such as NK cells and T cells may be derived from peripheral blood, umbilical cord blood, bone marrow or stem cells (including induced pluripotent stem cells). These immune cells may be subjected to ex vivo expansion and activation using the present UAPCs, which is required for cultivation to reach meaningful quantities for clinically relevant applications such as cancer immunotherapy.

Thus, the present disclosure provides a series of helper cell lines designed and manufactured to condition, modulate, prime and expand human immune, such as NK, cells for cancer immunotherapy.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

An "immune disorder," "immune-related disorder," or "immune-mediated disorder" refers to a disorder in which the immune response plays a key role in the development or progression of the disease. Immune-mediated disorders include autoimmune disorders, allograft rejection, graft versus host disease and inflammatory and allergic conditions.

An "immune response" is a response of a cell of the immune system, such as a B cell, or a T cell, or innate immune cell to a stimulus. In one embodiment, the response is specific for a particular antigen (an "antigen-specific response").

An "autoimmune disease" refers to a disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

"Subject" and "patient" refer to either a human or non-human, such as primates, mammals, and vertebrates. In particular embodiments, the subject is a human.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "haplotyping or tissue typing" refers to a method used to identify the haplotype or tissue types of a subject, for example by determining which HLA locus (or loci) is expressed on the lymphocytes of a particular subject.

The HLA genes are located in the major histocompatibility complex (MHC), a region on the short arm of chromosome 6, and are involved in cell-cell interaction, immune response, organ transplantation, development of cancer, and susceptibility to disease. There are six genetic loci important in transplantation, designated HLA-A, HLA-B, HLA-C, and HLA-DR, HLA-DP and HLA-DQ. At each locus, there can be any of several different alleles.

A widely used method for haplotyping uses the polymerase chain reaction (PCR) to compare the DNA of the subject, with known segments of the genes encoding MHC antigens. The variability of these regions of the genes determines the tissue type or haplotype of the subject. Serologic methods are also used to detect serologically defined antigens on the surfaces of cells. HLA-A, -B, and -C determinants can be measured by known serologic techniques. Briefly, lymphocytes from the subject (isolated from fresh peripheral blood) are incubated with antisera that recognize all known HLA antigens. The cells are spread in a tray with microscopic wells containing various kinds of antisera. The cells are incubated for 30 minutes, followed by an additional 60-minute complement incubation. If the lymphocytes have on their surfaces antigens recognized by the antibodies in the antiserum, the lymphocytes are lysed. A dye can be added to show changes in the permeability of the cell membrane and cell death. The pattern of cells destroyed by lysis indicates the degree of histologic incompatibility. If, for example, the lymphocytes from a person being tested for HLA-A3 are destroyed in a well containing antisera for HLA-A3, the test is positive for this antigen group.

The term "antigen presenting cells (APCs)" refers to a class of cells capable of presenting one or more antigens in the form of a peptide-MHC complex recognizable by specific effector cells of the immune system, and thereby inducing an effective cellular immune response against the antigen or antigens being presented. The term "APC" encompasses intact whole cells such as macrophages, B cells, endothelial cells, activated T cells, and dendritic cells, or molecules, naturally occurring or synthetic capable of presenting antigen, such as purified MHC Class I molecules complexed to ÿ2-microglobulin.

II. Universal Antigen Presenting Cells

Some embodiments of the present disclosure concern the production and use of universal antigen present cells (UAPCS). The UAPCs may be used for the expansion of immune cells, such as NK cells and T cells. The UAPCs may be engineered to express membrane-bound IL-21 (mbIL-21) and 41BBL (CD137 ligand).

The UAPCs may be engineered to express CD ligand and/or a membrane-bound cytokine. The membrane-bound cytokine may be mIL-21 or mIL-15. In particular embodiments, the UAPCs are engineered to express CD137 ligand and mIL-21. The APCs may be derived from cancer cells, such as leukemia cells. The APCs may not have any expression of endogenous HLA class I, II, or CD1d molecules. The APCs may express ICAM-1 (CD54) and LFA-3 (CD58). In particular, the APCs may be K562 cells, such as K562 cells engineered to express CD137 ligand and mIL-21. The APCs may be irradiated. The engineering may be by any method known in the art, such as retroviral transduction.

Cytokines exert very potent controls over entire classes of immune cells (including NK cells), affecting cellular fate, activity and efficacy of cellular responses. The power of cytokine stimulation to activate NK cells confirms their "natural" effector functions are highly susceptible to environmental intervention, and that priming may regulate NK cell behaviors in vivo.

To address the issue of acquiring clinically relevant quantities of NK cells, the present methods may use interleukin (IL-21) as the driver for NK cell expansion in the present UAPC platform technology. In humans, NK-cell stimulation with IL-10 and IL-21 induces NKG2D expression in a STAT3-dependent manner. While the cytokine receptors share similar cellular signaling components in many immune cells, NK cell-specific signaling is dependent on the IL-21 receptor-STAT3 nexus for proliferation.

Cytokine signaling is important for maintenance of lymphocyte survival and proliferation. In vivo, IL-2 administration is the only FDA approved method for expanding NK cells. IL-15, another potent NK cell activator, is undergoing Phase I clinical trial as a possible alternative to IL-2, but may have significant toxicity following systemic administration. Apart from significant toxicities, these cytokines also induce proliferation of T cells while limiting the persistence of NK cells. Despite sharing the same receptor for signal transduction, IL-2, IL-4, IL-7, IL-9, IL-15, and IL-21 receptors have distinct and specific effects on diverse cells.

A. Membrane-Bound IL-21

In certain embodiments, for specifically energizing NK cells, IL-21 may be used for producing the present UAPCs. IL-21 receptor (IL21R), a close relation to the IL-2 receptor beta chain capable of transducing signals through its dimerization with the common cytokine receptor gamma chain (gamma(c), is upregulated in activated human NK cells (cells ready to be triggered). While IL-21, a type I cytokine, can modulate T, B, and NK cell functions, the present studies found that only human NK cells experience significant expansion via activation of the IL21 receptor signaling pathway (i.e., 1000-fold over 21 days). Conversely, IL21 plays an important role in the contraction of $CD8^+$ T cells.

IL21R signaling is powered mainly by STAT3, a highly potent cellular proliferation activator. The IL21R-STAT3 nexus is driven by IL-21-induced STAT3 DNA binding to GAS and cis-inducible elements as verified by immunoprecipitation and Western blotting with anti-phosphotyrosine antibody. The molecular basis of IL21 mediated proliferation can be specifically traced to tyrosine 510 (Y510) on IL21R, which mediates IL-21-induced phosphorylation of STAT1 and STAT33. This mechanism is underscored by dampened IL-21 responses in Stat1/Stat3 double knock-out mice.

IL21R signaling is important for NK cytotoxicity. Human IL21R deficiency is linked to impaired cytolysis of 51Cr-labeled K562 target cells, while antibody-dependent cellular cytotoxicity is unaffected. The monogenic non-embryonic lethal defect (loss-of-function mutation in IL21R) presents an excellent opportunity delineate, and thus useful in modeling, enhancing, and shaping innate NK cytolytic responses.

IL-21 signaling selectively molds NK cell subsets, even though both $CD56^{dim}$ and $CD56^{bright}$ cell populations harbor similar numbers of surface IL21R. IL-21 induction of STAT1 and STAT3 phosphorylation is higher in CD56bright vs CD56dim NK cells. In contrast, IL-21 has no effect on STATS activation, an IL-2 activation pathway which also drives T cell expansion. In addition to STAT3 activation, IL-21 signaling also involves the MAPK, and PI3K pathways and induces expression of innate immune responsive genes including IFN-gamma, T-bet, IL-12Rbeta2, and IL-18R in NK cells, priming them to kill tumor cells.

Figure 4A:
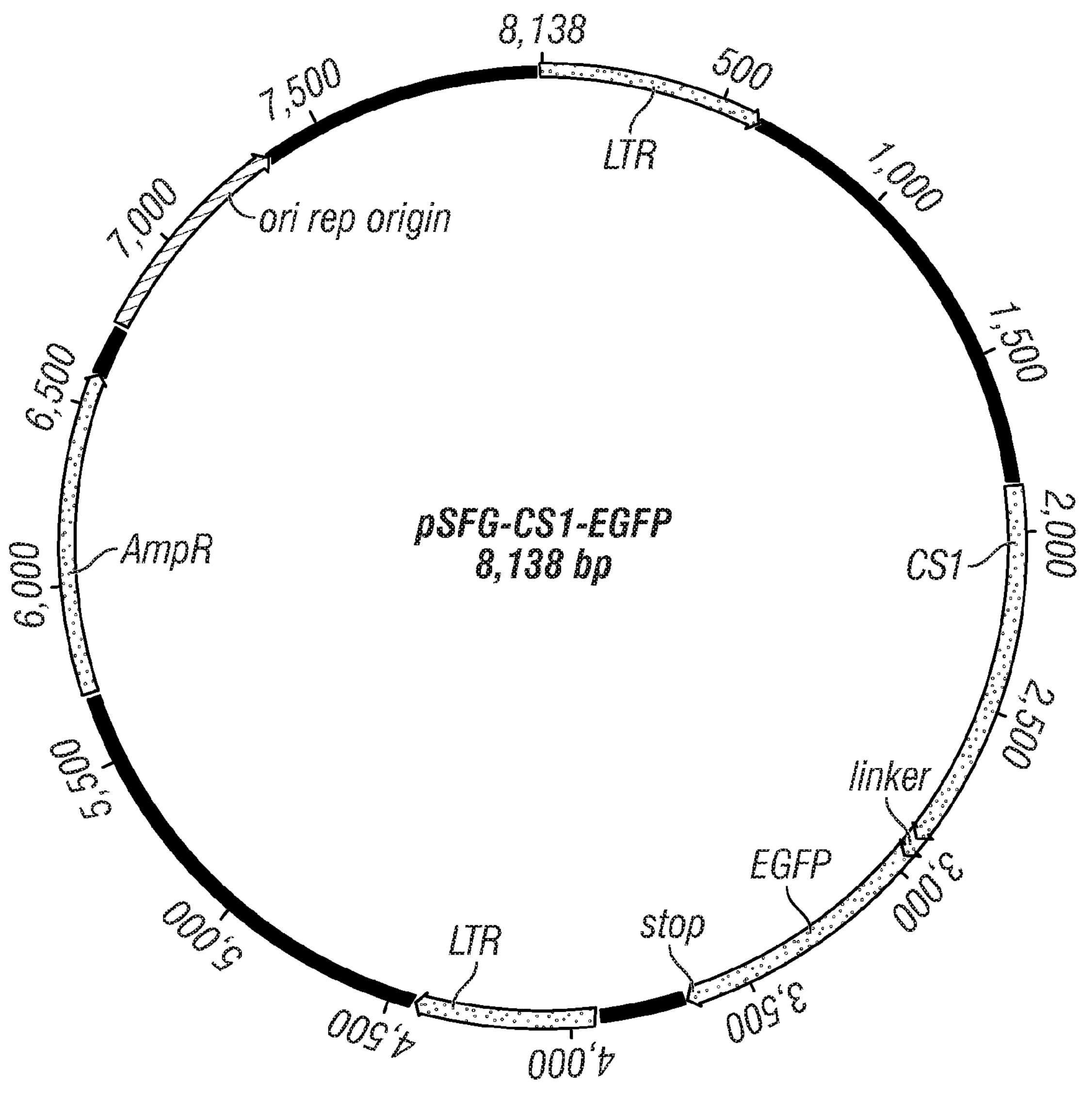
FIGS. 4A-4D: MMLV-retroviral transfer construct maps and annotations.
Figure 4B:
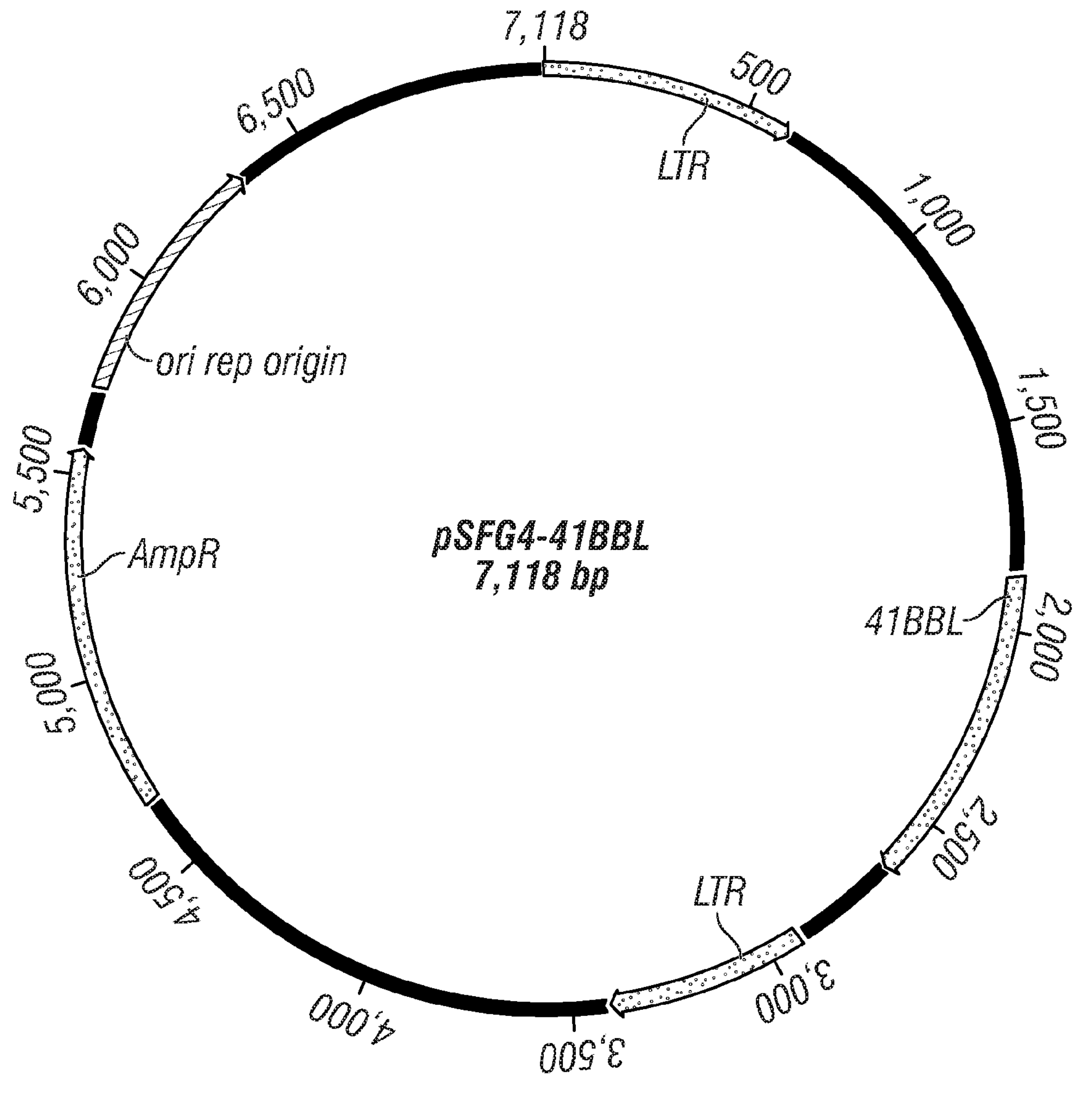
Figure 4C:
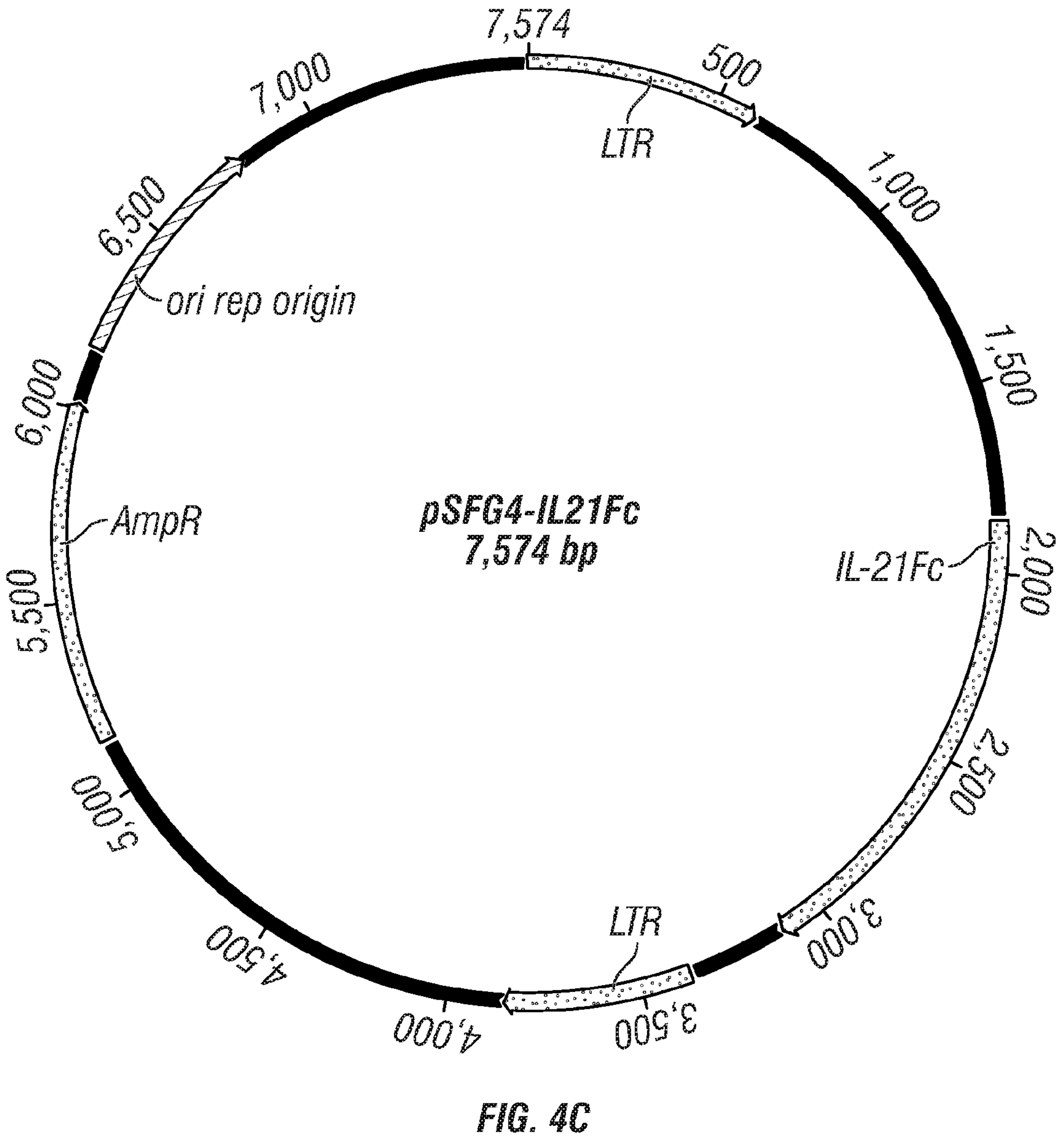
Figure 4D:
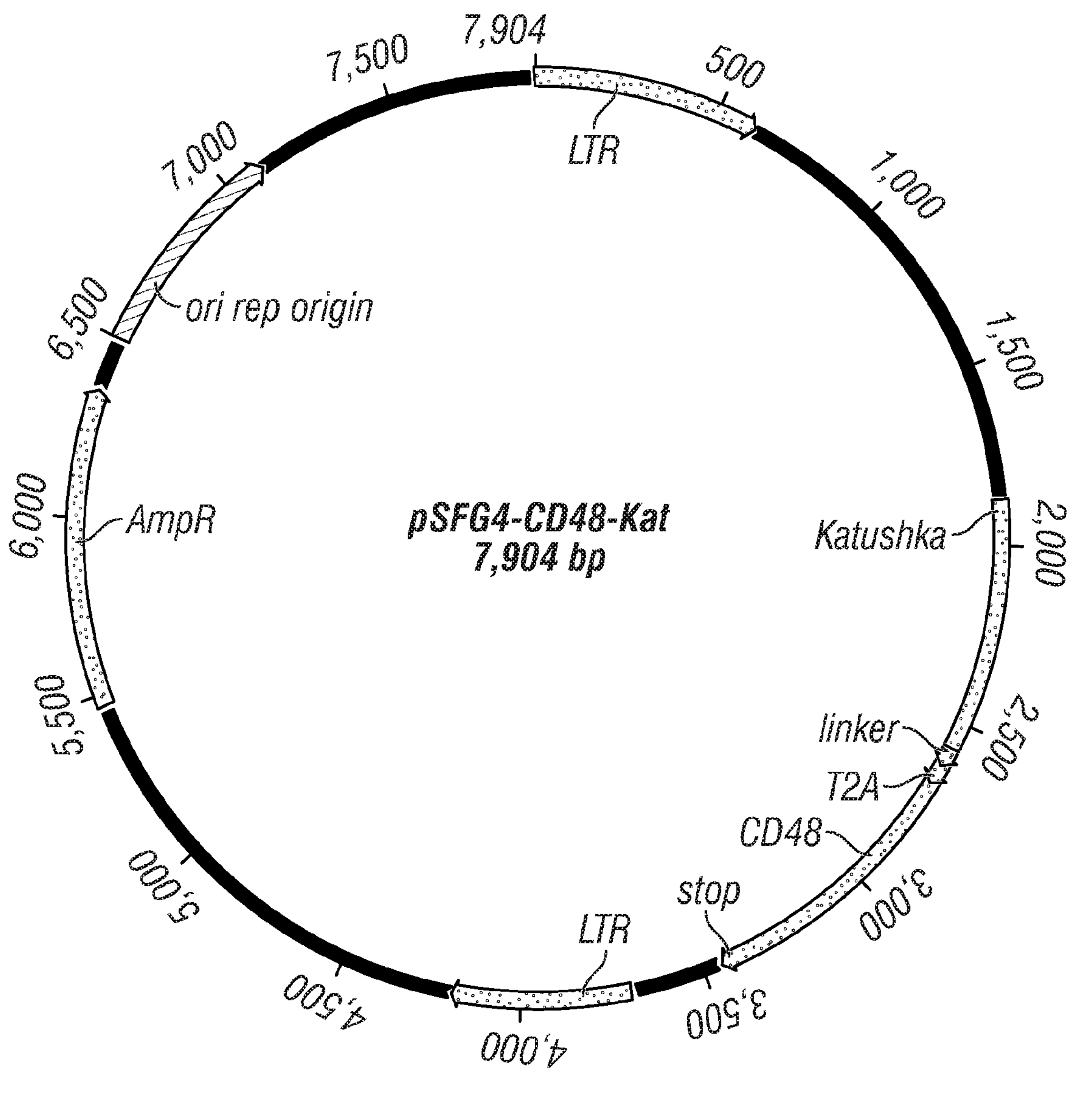

For efficient utilization of IL-21, expression of mbIL-21 (FIG. 4A) may be used to concentrate and localize trans interaction with IL21R on NK cells. The membrane proximity of mbIL21 ensures ready availability where it is needed, thus, it can sustain optimal cell proliferation without large quantities and concentrations of exogenously supplied IL-21. Co-cultures with irradiated K562-mb15-41BBL induced a median 21.6-fold expansion of CD56+CD3− NK cells from peripheral blood. This expansion is higher compared to stimulation with just soluble cytokines from the shared γc family including IL-2, IL-12, IL-15, IL-21 alone or in combinations. By comparison, the present UAPCS can expand NK cells by at least 1000-fold (3-log) over 14-21 days. Expression of mbIL21 on UAPCs can also obviate the need for exogenous clinical-grade cytokine.

B. 4-1BBL (4-1BB ligand, CD137 ligand, CD137L, TNFSF9)

In addition to the notion of cytokine priming of NK cell function, direct physical interactions with activating molecules in NK cells result in enhanced cellular proliferative responses. CD137 (4-1BB) is a member of the tumor necrosis receptor (TNF-R) gene family, which mediates cell proliferation, differentiation, and programmed cell death (apoptosis). The murine receptor was first characterized followed by the human homolog, which shares a 60% identity at the amino acid level, with significant conservation in the cytoplasmic/signaling domain. CD137 is mainly expressed in activated T-cells and NK cells, with varying levels detectable in thymocytes, myeloid cells, and endothelial cells at sites of inflammations. Physiological CD137 signaling is mediated via 1) NF-κB which promotes survival through Bcl-XL activation and 2) PI3K/ERK1/2 pathway which specifically drive cell cycle progression.

In activated NK cells, CD137 is a cytokine-inducible costimulatory molecule, which in turn drives anti-tumor responses in NK cells by increasing cellular proliferation and IFN-γ secretion. Studies using CD137L−/− knockout mice elucidated the importance of CD137/CD137L signaling in developing anti-tumor immune cells. CD137−/− knockout mice had a 4-fold higher frequency of tumor metastases compared to control mice.

CD137 ligand (CD137L, 4-1BB ligand), a 34 kDa glycoprotein member of the TNF superfamily, is detected mainly on activated antigen-presenting cells (APC), including B cells, macrophages, and dendritic cells as well as transiently expressed at low levels on activated T cells. Human CD137L is only 36% homologous compared to the murine counterpart. In line with anti-tumor efficacies of agonistic CD137 antibodies, CD137L binding has been shown to elicit CTL and anti-tumor activities.

Accordingly, the present UAPCS may be engineered to express 4-1BB ligand, the physiological counter-receptor for CD137 for stimulation.

C. SLAM/CD48

Apart from cytokine conditioning and 4-1BBL co-stimulation, direct physical interactions between NK and target cells also influence the cellular responses i.e. killing of the target cells. The signaling lymphocytic activating molecule (SLAM, previously also known as CD2 superfamily) family of homologous immunoglobulin receptors, which are widely expressed and play critical roles in the immune system, are especially important in terms of intercellular interactions.

Accordingly, the UAPCs of the present disclosure may express one or more SLAM family antigens. SLAM family members include CD2, CD48, CD58 (LFA-3), CD244 (2B4), CD229 (Ly9), CD319 (CS1 (CD2 subset 1); CRACC (CD2-like receptor activating cytotoxic cells)), and CD352 (NTB-A (NK-T-B antigen)). In particular aspects, the UAPCs express CD48 and/or CS1. NK cells express at least three members of the SLAM family (SLAMF). They are 2B4, NK, T- and B-cell antigen (NTB-A), and CD2-like receptor-activating cytotoxic cells (CRACC), which recognize their respective ligands CD48, NTB-A, and CRACC on target cells and possibly on other NK cells. While SLAMF1, 3, 5, 6, 7, 8, and 9 are homophilic (self-ligand) receptors, SLAMF2 and SLAMF4 are counter receptors (heterophilic) to each other. The broad range (three orders of magnitude) in known homophilic affinities (dissociation constant, Kd, of <1 μM to 200 μM) points to a mechanistic basis for the overlapping, but distinct, signaling mechanisms for the SLAM glycoproteins.

TABLE 1

SLAM family members binding affinities.

| SLAMF | CD | Name | Aliases | Interaction | Counter Receptor | Affinity |
|---|---|---|---|---|---|---|
| 1 | 150 | SLAM | SLAMF1, CD150, CDw150 | homophilic | | 200 |
| 2 | 48 | CD48 | BCM1, BLAST, BLAST1, MEM-102 | heterophilic | CD2 (rodents) | >500 |
| | | | | heterophilic | 2B4 | 8 |
| 3 | 229 | LY9 | hly9, mlymphocyte antigen 9 | homophilic | | |
| 4 | 244 | 2B4 | NAIL, NKR2B4, Nmrk | heterophilic | CD48 | 8 |
| 5 | 84 | CD84 | LY9B | homophilic | | <1 |
| 6 | 352 | NTB-A | KALI, KALIb, Ly108, NTBA, SF2000 | homophilic | | 2 |

TABLE 1-continued

SLAM family members binding affinities.

| SLAMF | CD | Name | Aliases | Interaction | Counter Receptor | Affinity |
|---|---|---|---|---|---|---|
| 7 | 319 | CRACC | CS1, 19A | homophilic | | |
| 8 | 353 | | BLAME, SBBI42 | homophilic | | |
| 9 | | | CD2F10, CD84H1, SF2001, CD2F-10, CD84-H1 | homophilic | | |

In particular embodiments, the present UAPCs are engineered to express CD48 to bolster cell-to-cell interaction to enhance NK cellular responses. CD48 is a glycosylphosphatidylinositol-anchored protein (GPI-AP) found on the surface of NK cells, T cells, monocytes, and basophils, and participates in adhesion and activation pathways in these cells. Despite its lack of an intracellular domain, stimulation of CD48 induces rearrangement of signaling factors in lipid rafts, Lck-kinase activity, and tyrosine phosphorylation. As an adhesion and co-stimulatory molecule, CD48 induces numerous effects in B and T lymphocytes, NK cells, mast cells, and eosinophils. In human NK cells, CD48 is the counter receptor for 2B426, an important activator of NK cells. The heterophilic interaction is thought to compete for CD244 interaction with MHC-I. 2B4/CD48 interaction thus induces activation signals in human NK cells, whereas in murine NK cells it sends inhibitory signals.

While 2B4-CD48 interactions between cells of the same population, i.e. NK cell-NK cell interactions or T cell-T cell interactions, leads to enhanced activation, by expressing CD48 on APCs, such as K562 myeloid cell line which is normally devoid of CD48, the UAPCs can turn on the potent 2B4 signaling pathway on NK cells in trans.

D. SLAM/CS1

In some embodiments, the present UAPCs are engineered to express CS1, another member of the SLAM family, as a co-stimulatory molecule to switch on the killing powers of NK cells. Unlike CD48 which counter binds to 2B4, CS1 interactions are homophilic, and can be characterized in the context of cis vs trans interactions. K562 cells which are normally free of CS1 may be engineered to express CS1.

E. Delivery of Nucleic Acids

The mbIL-21, 41BBL, and co-stimulatory antigen may be engineered by any of the methods known in the art. The nucleic acid typically is administered in the form of an expression vector, such as a viral expression vector. In some aspects, the expression vector is a retroviral expression vector, an adenoviral expression vector, a DNA plasmid expression vector, or an AAV expression vector. In some aspects, the delivery is by delivery of one or more vectors, one or more transcripts thereof, and/or one or more proteins transcribed therefrom, is delivered to the cell.

Methods for introducing a polynucleotide construct into animal cells are known and include, as non-limiting examples stable transformation methods wherein the polynucleotide construct is integrated into the genome of the cell, transient transformation methods wherein the polynucleotide construct is not integrated into the genome of the cell, and virus mediated methods. In some embodiments, the polynucleotides may be introduced into the cell by for example, recombinant viral vectors (e.g. retroviruses, adenoviruses), liposome and the like. For example, in some aspects, transient transformation methods include microinjection, electroporation, or particle bombardment. In some embodiments, the polynucleotides may be included in vectors, more particularly plasmids or virus, in view of being expressed in the cells.

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in (e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91117424; WO 91116024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer.

III. Immune Cells

Some embodiments of the present disclosure concern the isolation and expansion of immune cells, such as a NK cells or T cells, such as for cancer immunotherapy.

In certain embodiments, immune cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. Specifically, the immune cells may be isolated from cord blood (CB), peripheral blood (PB), bone marrow, or stem cells. In particular embodiments, the immune cells are isolated from pooled CB. The CB may be pooled from 2, 3, 4, 5, 6, 7, 8, 10, or more units. The immune cells may be autologous or allogeneic. The isolated immune cells may be haplotype matched for the subject to be administered the cell therapy. NK cells can be detected by specific surface markers, such as CD16, CD56, and CD8 in humans.

In certain aspects, the NK cells are isolated by the previously described method of ex vivo expansion of NK cells (Spanholtz et al., 2011; Shah et al., 2013). In this method, CB mononuclear cells are isolated by ficoll density gradient centrifugation. The cell culture may be depleted of any cells expressing CD3 and may be characterized to determine the percentage of $CD56^+/CD3^-$ cells or NK cells. In other methods, umbilical CB is used to derive NK cells by the isolation of $CD34^+$ cells. The method may comprise depletion of CD3, CD14, and/or CD19-positive cells.

The isolated immune cells may be expanded in the presence of the present UAPCs. The expansion may be for about 2-30 days, such as 3-20 days, particularly 12-16 days, such as 12, 13, 14, 15, 16, 17, 18, or 19 days, specifically about 14 days. The immune cells and UAPCS may be present at a ratio of about 3:1-1:3, such as 2:1, 1:1, 1:2, specifically about 1:2. The expansion culture may further comprise cytokines to promote expansion, such as IL-2. The IL-2 may be present at a concentration of about 10-500 U/mL, such as 100-300 U/mL, particularly about 200 U/mL. The IL-2 may be replenished in the expansion culture, such as every 2-3 days. The UAPCs may be added to the culture at least a second time, such as at about 7 days of expansion.

Following expansion, the immune cells may be immediately infused or may be stored, such as by cryopreservation. In certain aspects, the cells may be propagated for days, weeks, or months ex vivo as a bulk population within about 1, 2, 3, 4, 5 days.

Expanded NK cells can secrete type I cytokines, such as interferon-γ, tumor necrosis factor-α and granulocyte-macrophage colony-stimulating factor (GM-CSF), which activate both innate and adaptive immune cells as well as other cytokines and chemokines. The measurement of these cytokines can be used to determine the activation status of NK cells. In addition, other methods known in the art for determination of NK cell activation may be used for characterization of the NK cells of the present disclosure.

IV. Chimeric Antigen Receptors

In certain embodiments, the present immune cells, such as T cells or NK cells, are genetically modified to express a chimeric antigen receptor (CAR). In some embodiments, the CAR comprises: a) an intracellular signaling domain, b) a transmembrane domain, and c) an extracellular domain comprising an antigen binding region.

A CAR recognizes cell-surface tumor-associated antigen independent of human leukocyte antigen (HLA) and employs one or more signaling molecules to activate genetically modified NK cells for killing, proliferation, and cytokine production. In certain embodiments, the present NK cells may be genetically modified by methods comprising (i) non-viral gene transfer using an electroporation device (e.g., a nucleofector), (ii) CARs that signal through endodomains (e.g., CD28/CD3-ζ, CD137/CD3-ζ, or other combinations), (iii) CARs with variable lengths of extracellular domains connecting the antigen-recognition domain to the cell surface, and, in some cases, (iv) artificial antigen presenting cells (aAPCs) derived from K562 to be able to robustly and numerically expand $CAR^+$ NK cells (Singh et al., 2011).

Embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the present methods use a full-length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One of the Fc domains, e.g., either the CH2 or CH3 domain from human immunoglobulin may be used. The hinge, CH2 and CH3 region of a human immunoglobulin that has been modified to improve dimerization may be used. In other aspects, just the hinge portion of an immunoglobulin or portions of CD8α may be used.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, and 4-1BB (CD137). In addition to a primary signal initiated by CD3ζ, an additional signal provided by a human costimulatory receptor inserted in a human CAR is important for full activation of NK cells and could help improve in vivo persistence and the therapeutic success of the adoptive immunotherapy.

The intracellular signaling domain of a chimeric antigen receptor is responsible for activation of at least one of the normal effector functions of the immune cell in which the chimeric antigen receptor has been placed. The effector function is a specialized function of a differentiated cell, such as a NK cell. In specific embodiments, intracellular receptor signaling domains in the CAR include those of the T cell antigen receptor complex, such as the zeta chain of CD3, also Fcγ RIII costimulatory signaling domains, CD28, CD27, DAP10, CD137, OX40, CD2, alone or in a series with CD3zeta, for example. In specific embodiments, the intracellular domain (which may be referred to as the cytoplasmic domain) comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. Any part of the endogenous T cell receptor complex may be used in the intracellular domain. One or multiple cytoplasmic domains may be employed, as so-called third generation CARs have at least two or three signaling domains fused together for additive or synergistic effect, for example.

In certain embodiments of the CAR, the antigen-specific portion of the receptor (which may be referred to as an extracellular domain comprising an antigen binding region) comprises a tumor associated antigen or a pathogen-specific antigen binding domain. Antigens include carbohydrate antigens recognized by pattern-recognition receptors, such as Dectin-1. A tumor associated antigen may be of any kind so long as it is expressed on the cell surface of tumor cells. The tumor antigen-binding domain may be, but is not limited to, CD19, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, or VEGFR2. The CAR may comprise a humanized scFv, such as humanized CD19 or CD123.

In certain embodiments, the CAR may be co-expressed with a cytokine to improve persistence when there is a low amount of tumor-associated antigen. For example, CAR may be co-expressed with IL-15.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into NK cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into NK cells. Suitable vectors for use in accordance with the method of the present invention are non-replicating in the NK cells. A large number of vectors are known that are based on viruses, where the copy number of the virus maintained in the cell is low enough to maintain the viability of the cell, such as, for example, vectors based on HIV, SV40, EBV, HSV, or BPV.

The CAR may be co-expressed with a suicide gene, such as CD20, CD52, EGFRv3, or inducible caspase 9.

The CAR may comprise a tumor antigen-binding domain. The tumor antigen-binding domain may be, but is not limited to, CD19, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, or VEGFR2. The CAR may comprise a humanized scFv, such as humanized CD19, CD123, mesothelin, CD5, CD47, CLL-1, CD33, CD99, U5snRNP200, CD200, CS1, BAFF-R, ROR-1, or BCMA.

V. Methods of Use

Embodiments of the present disclosure concern methods for the use of the immune, such as NK or T, cells provided herein (e.g., expanded by the present UAPCs) for treating or preventing a medical disease or disorder by transfer of an immune cell population that elicits an immune response. The method includes administering to the subject a therapeutically effective amount of the expanded immune cells, thereby treating or preventing the disorder in the subject. In certain embodiments of the present disclosure, cancer or infection is treated by transfer of an immune cell population that elicits an immune response. Due to their release of pro-inflammatory cytokines, immune cells may reverse the anti-inflammatory tumor microenvironment and increase adaptive immune responses by promoting differentiation, activation, and/or recruitment of accessory immune cell to sites of malignancy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma;

glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

Acute leukemia is characterized by the rapid proliferation of immature blood cells. This crowding makes the bone marrow unable to produce healthy blood cells. Acute forms of leukemia can occur in children and young adults. Immediate treatment is required in acute leukemia due to the rapid progression and accumulation of the malignant cells, which then spill over into the bloodstream and spread to other organs of the body. Central nervous system (CNS) involvement is uncommon, although the disease can occasionally cause cranial nerve palsies. Chronic leukemia is distinguished by the excessive build up of relatively mature, but still abnormal, blood cells. Typically taking months to years to progress, the cells are produced at a much higher rate than normal cells, resulting in many abnormal white blood cells in the blood. Chronic leukemia mostly occurs in older people, but can theoretically occur in any age group. Whereas acute leukemia must be treated immediately, chronic forms are sometimes monitored for some time before treatment to ensure maximum effectiveness of therapy.

Furthermore, the diseases are classified into lymphocytic or lymphoblastic, which indicate that the cancerous change took place in a type of marrow cell that normally goes on to form lymphocytes, and myelogenous or myeloid, which indicate that the cancerous change took place in a type of marrow cell that normally goes on to form red cells, some types of white cells, and platelets.

Acute lymphocytic leukemia (also known as acute lymphoblastic leukemia, or ALL) is the most common type of leukemia in young children. This disease also affects adults, especially those aged 65 and older. Chronic lymphocytic leukemia (CLL) most often affects adults over the age of 55. It sometimes occurs in younger adults, but it almost never affects children. Acute myelogenous leukemia (also known as acute myeloid leukemia, or AML) occurs more commonly in adults than in children. This type of leukemia was previously called acute nonlymphocytic leukemia. Chronic myelogenous leukemia (CIVIL) occurs mainly in adults.

Lymphoma is a type of cancer that originates in lymphocytes (a type of white blood cell in the vertebrate immune system). There are many types of lymphoma. According to the U.S. National Institutes of Health, lymphomas account for about five percent of all cases of cancer in the United States, and Hodgkin's lymphoma in particular accounts for less than one percent of all cases of cancer in the United States. Because the lymphatic system is part of the body's immune system, patients with a weakened immune system, such as from HIV infection or from certain drugs or medication, also have a higher incidence of lymphoma.

In certain embodiments of the present disclosure, immune cells are delivered to an individual in need thereof, such as an individual that has cancer or an infection. The cells then enhance the individual's immune system to attack the respective cancer or pathogenic cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

The source of immune cells that are pre-activated and expanded may be of any kind, but in specific embodiments the cells are obtained from a bank of umbilical cord blood, peripheral blood, human embryonic stem cells, or induced pluripotent stem cells, for example. Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on Day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

In one exemplary method, the NK cells may be derived from a biological sample, such as one or more cord blood units. The cord blood unit may be a frozen cord blood unit. The cord blood unit may be thawed and subjected to a ficoll gradient to obtain mononuclear cells. The mononuclear cells may be depleted of CD3, CD14, and CD19 positive cells, such as by CliniMAS. The negatively-selected NK cells may then be cultured in the presence of APCs and IL-2 (e.g., 200 U/mL). The NK cells may then be transduced with retroviral supernatant expressing a CAR and cultured with γ-irradiated APCs and IL-2. Finally, the cells may be sorted for positive expression of the CAR, such as CD56, CD16, CD3, CD19, CD14, or CD45.

The immune cells generated according to the present methods have many potential uses, including experimental and therapeutic uses. In particular, it is envisaged that such cell populations will be extremely useful in suppressing undesirable or inappropriate immune responses. In such methods, a small number of immune cells are removed from a patient and then manipulated and expanded ex vivo before reinfusing them into the patient. Examples of diseases which may be treated in this way are autoimmune diseases and conditions in which suppressed immune activity is desirable, e.g., for allo-transplantation tolerance. A therapeutic method could comprise providing a mammal, obtaining immune cells from the mammal; expanding the immune cells ex vivo in accordance with the methods of the present methods as described above; and administering the expanded immune cells to the mammal to be treated.

A pharmaceutical composition of the present disclosure can be used alone or in combination with other well-established agents useful for treating cancer. Whether delivered alone or in combination with other agents, the pharmaceutical composition of the present disclosure can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

Certain embodiments of the present disclosure provide methods for treating or preventing an immune-mediated disorder. In one embodiment, the subject has an autoimmune disease. Non-limiting examples of autoimmune diseases include: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac spate-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune-mediated diabetes mellitus, myasthenia gravis, nephrotic syndrome (such as minimal change disease, focal glomerulosclerosis, or membranous nephropathy), pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjogren's syndrome, stiff-man syndrome, systemic lupus erythematosus, lupus erythematosus, ulcerative colitis, uveitis, vasculitides (such as polyarteritis nodosa, takayasu arteritis, temporal arteritis/giant cell arteritis, or dermatitis herpetiformis vasculitis), vitiligo, and Wegener's granulomatosis. Thus, some examples of an autoimmune disease that can be treated using the methods disclosed herein include, but are not limited to, multiple sclerosis, rheumatoid arthritis, systemic lupus erythematosis, type I diabetes mellitus, Crohn's disease; ulcerative colitis, myasthenia gravis, glomerulonephritis, ankylosing spondylitis, vasculitis, or psoriasis. The subject can also have an allergic disorder such as Asthma.

In yet another embodiment, the subject is the recipient of a transplanted organ or stem cells and immune cells are used to prevent and/or treat rejection. In particular embodiments, the subject has or is at risk of developing graft versus host disease. GVHD is a possible complication of any transplant that uses or contains stem cells from either a related or an unrelated donor. There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines. Any of the populations of immune cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. Immune cells can be administered prior to transplantation, concurrently with transplantation, or following transplantation. In some embodiments, the immune cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of immune cells occurs 3-5 days prior to transplantation.

In certain embodiments, the immune cells are administered in combination with a second therapeutic agent. For example, the second therapeutic agent may comprise T cells, an immunomodulatory agent, a monoclonal antibody, or a chemotherapeutic agent. In non-limiting examples, the immunomodulatory agent is lenalidomide, the monoclonal antibody is rituximab, ofatumab, or lumiliximab, and the chemotherapeutic agent is fludarabine or cyclophosphamide.

A composition of the present disclosure can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the isolated transduced immune cells is present in the composition and introduced into the subject such that long-term, specific, anti-tumor responses are established to reduce the size of a tumor or eliminate tumor growth or regrowth than would otherwise result in the absence of such treatment. Desirably, the amount of immune cells reintroduced into the subject causes a 10%, 20%, 30%, 40%, 50%, 60%, 70%, 80%, 90%, 95%, 98%, or 100% decrease in tumor size when compared to otherwise same conditions wherein the immune cells are not present.

Accordingly, the amount of immune cells administered should take into account the route of administration and should be such that a sufficient number of the immune cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of immune cells desirably should be sufficient to provide in the subject being treated at least from about $1\times10^6$ to about $1\times10^9$ immune cells, even more desirably, from about $1\times10^7$ to about $5\times10^8$ immune cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of immune cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

VI. Kits

In some embodiments, a kit that can include, for example, one or more media and components for the production of UAPCs and/or immune cells is provided. Such formulations may comprise a cocktail of factors, in a form suitable for combining with APCs and/or immune cells. The reagent system may be packaged either in aqueous media or in lyophilized form, where appropriate. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The components of the kit may be provided as dried powder(s). When reagents and/or components are provided as a dry powder, the powder can be reconstituted by the addition of a suitable solvent. It is envisioned that the solvent may also be provided in another container means. The kits also will typically include a means for containing the kit component(s) in close confinement for commercial sale. Such containers may include injection or blow molded plastic containers into which the desired vials are retained. The kit can also include instructions for use, such as in printed or electronic format, such as digital format.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Combination of mbIL21, 4-1BBL, and SLAM (CD48/CS1)

Figure 3A:
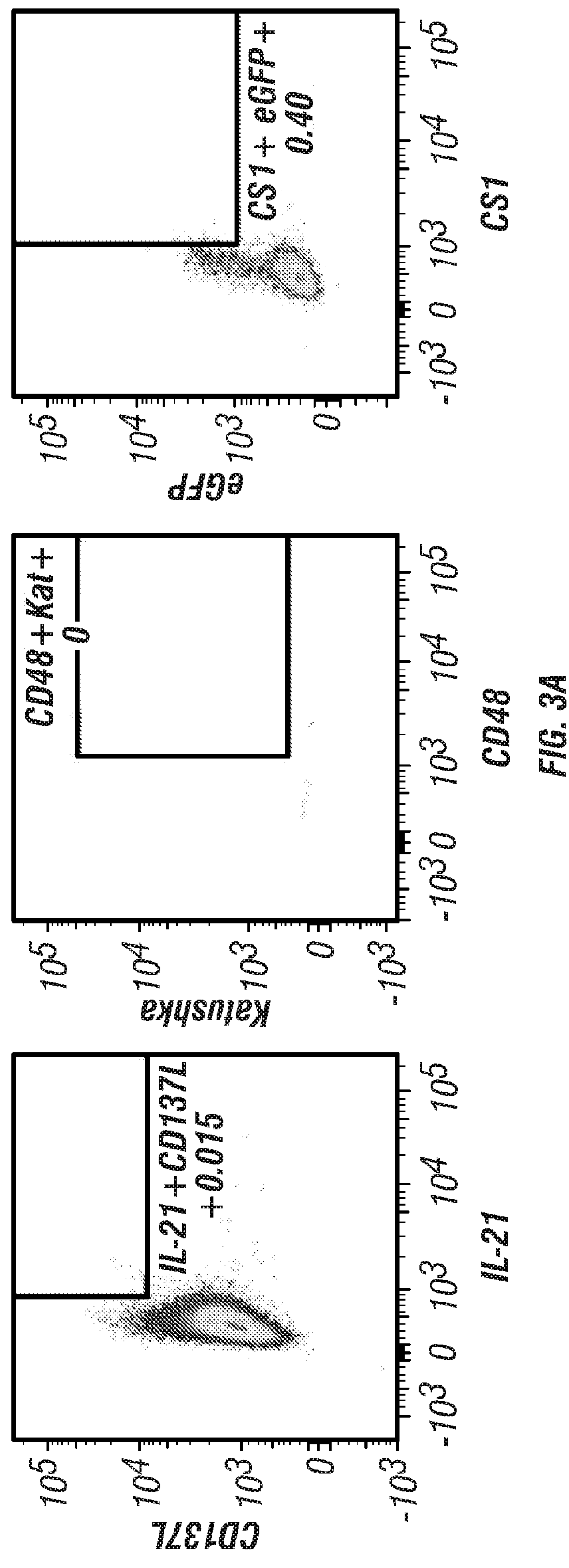
FIGS. 3A-3D.
Figure 3B:
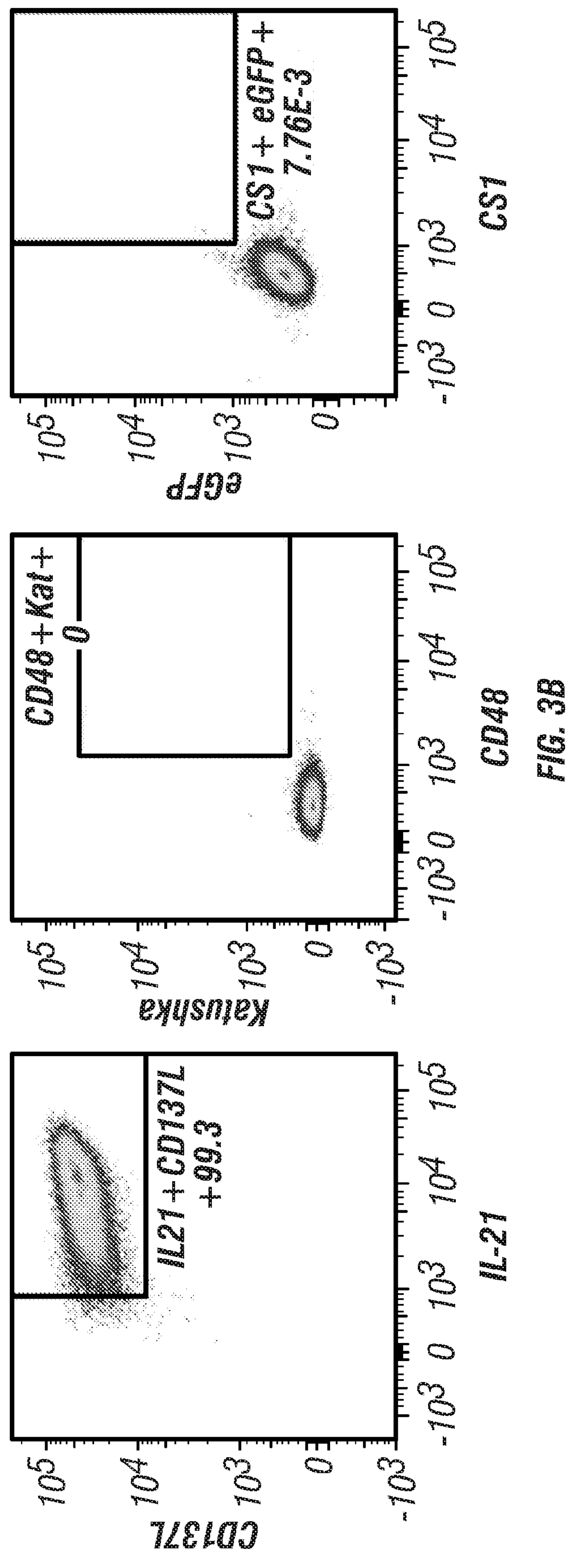
Figure 3C:
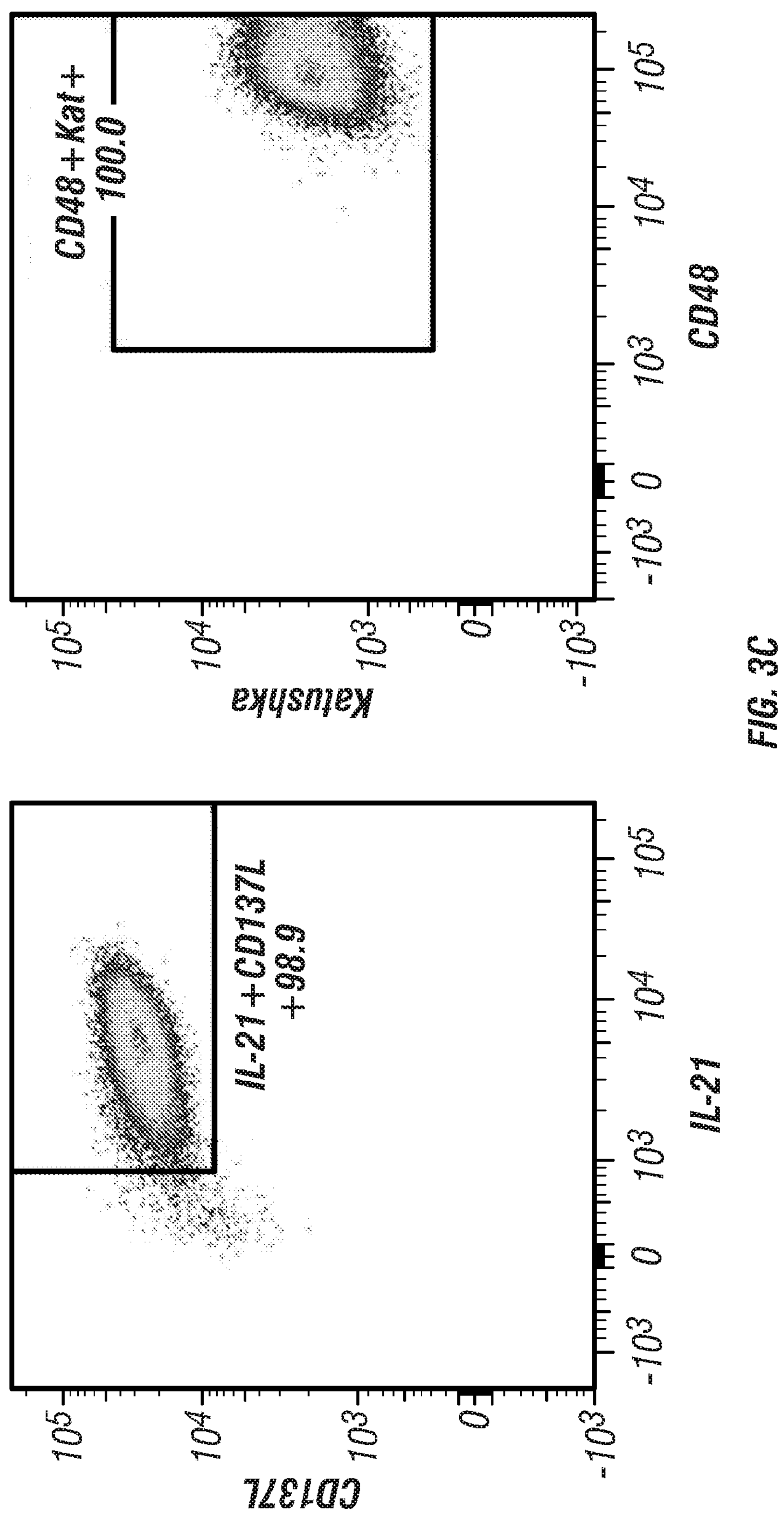
Figure 3D:
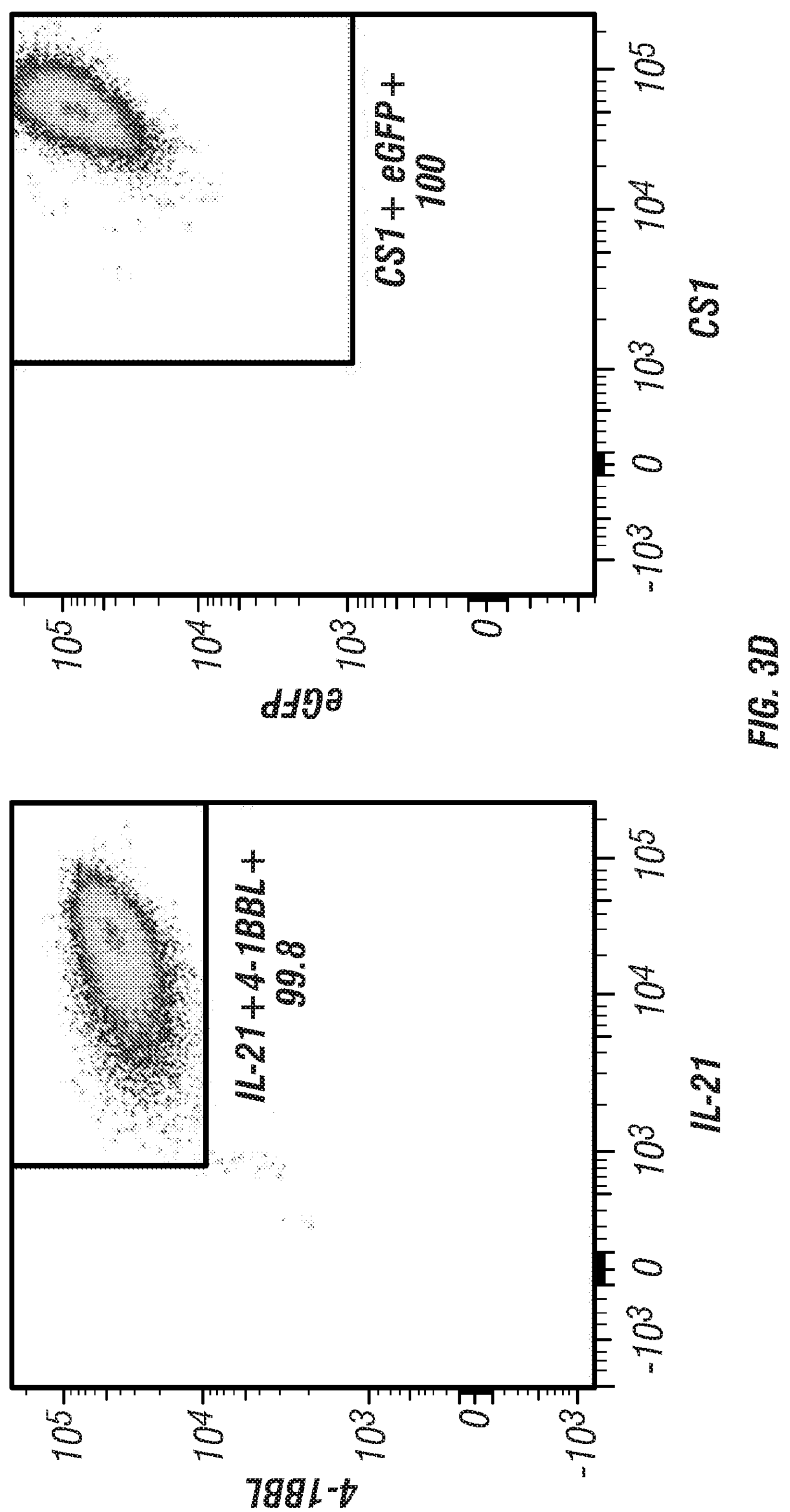

Universal antigen presenting cells (UAPCs) were generated by transduction of K562 cells with retroviral constructs for membrane-bound IL-21 and 41BBL (CD137 ligand) with either CD48-Katushka or CS1-EGFP. The MMLV-retroviral construct maps and annotations are shown in FIGS. 4A-4D. Clone 46 (FIG. 3B) was produced from enforced expression of mbIL-21 and 41BBL in NK cell-sensitive K562 (HLA-A$^-$, HLA-B$^-$) APCs (FIG. 3A). UAPC was generated by enforced expression of mbIL-1, 41BBL, and CD48 in the K562 cells (FIG. 3C). UAPC2 was generated by enforced expression of mbIL-21, 41BBL, and CS1 in the K562 cells (FIG. 3D).

Figure 2A:
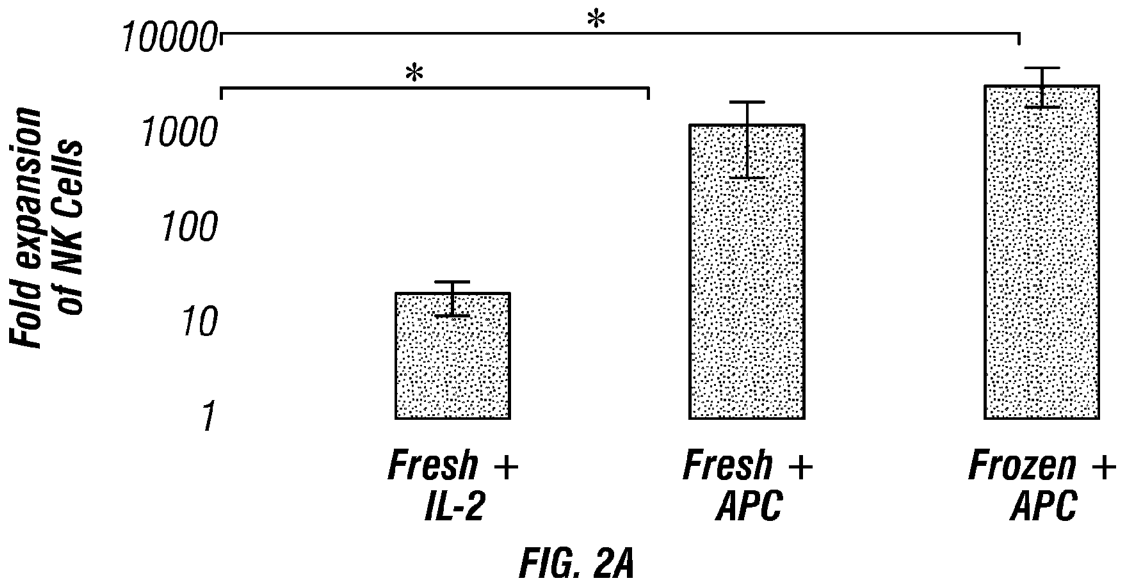
FIGS. 2A-2E.
Figure 2B:
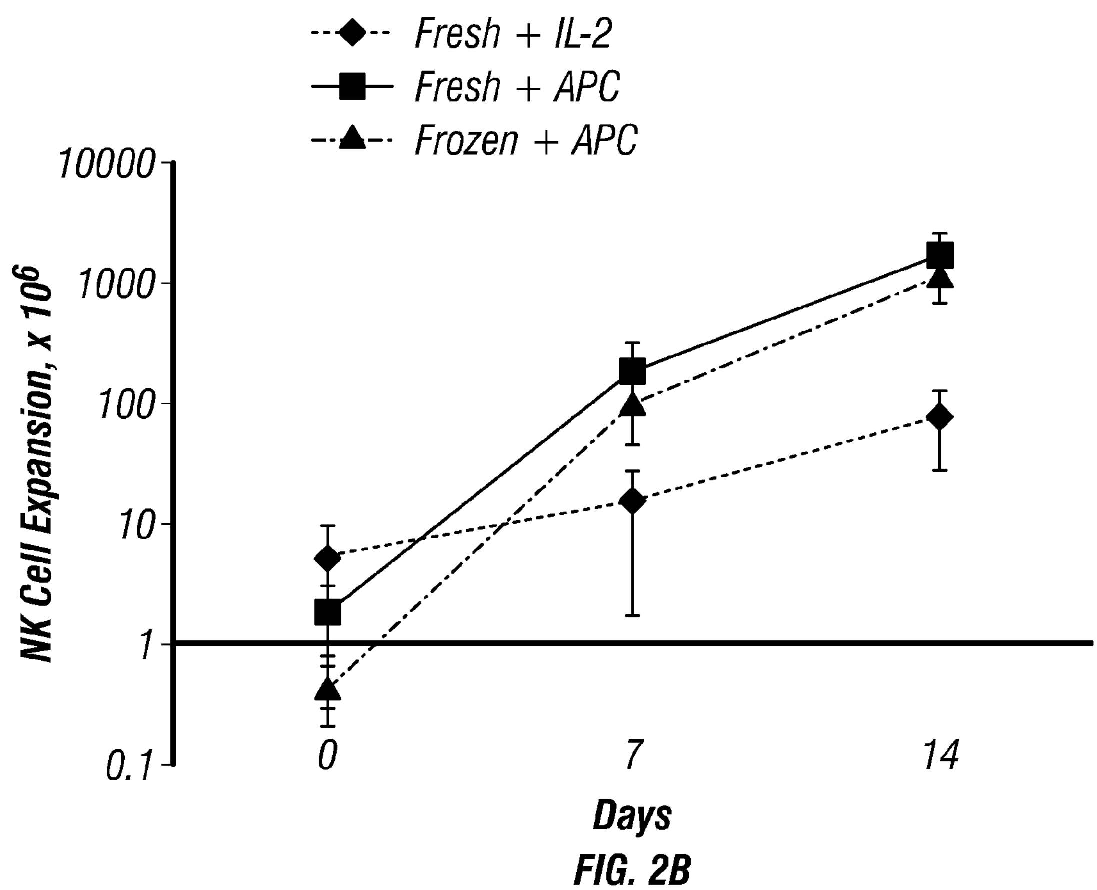
Figure 2C:
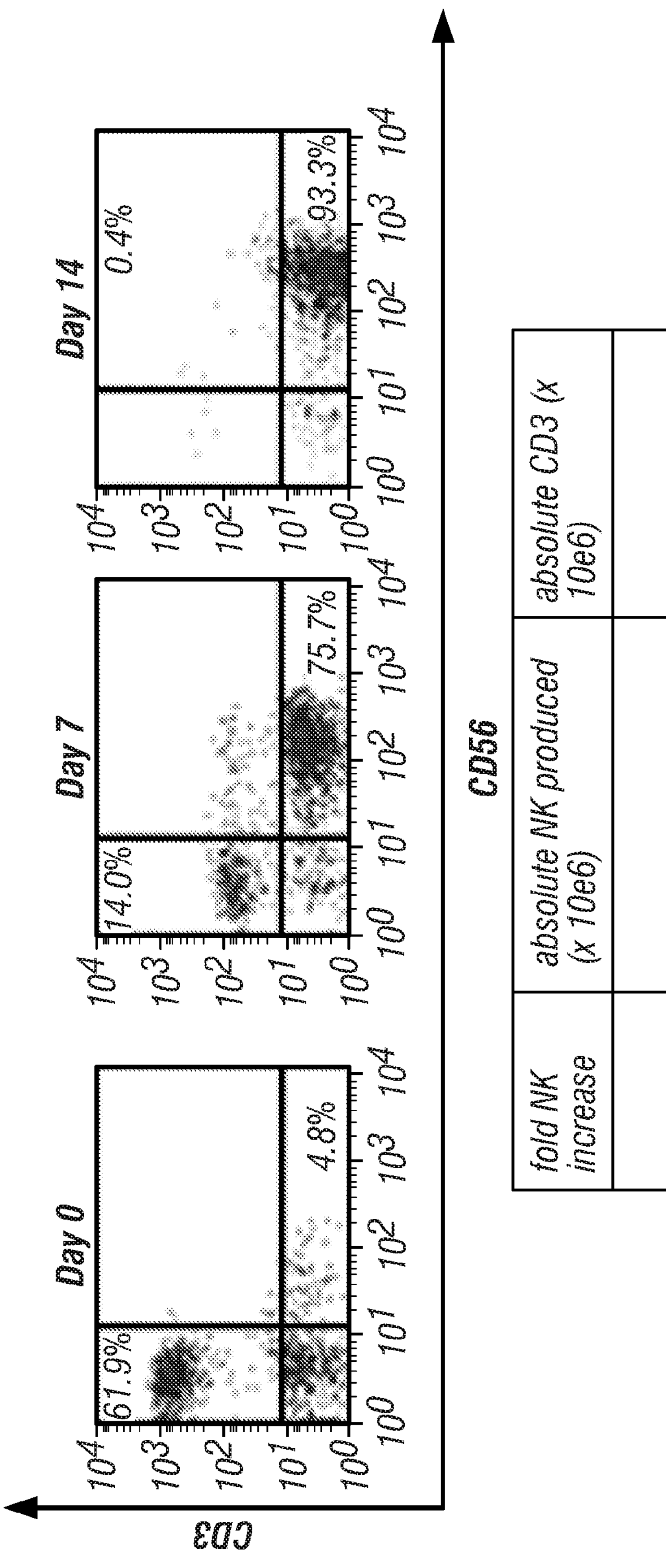
Figure 2D:
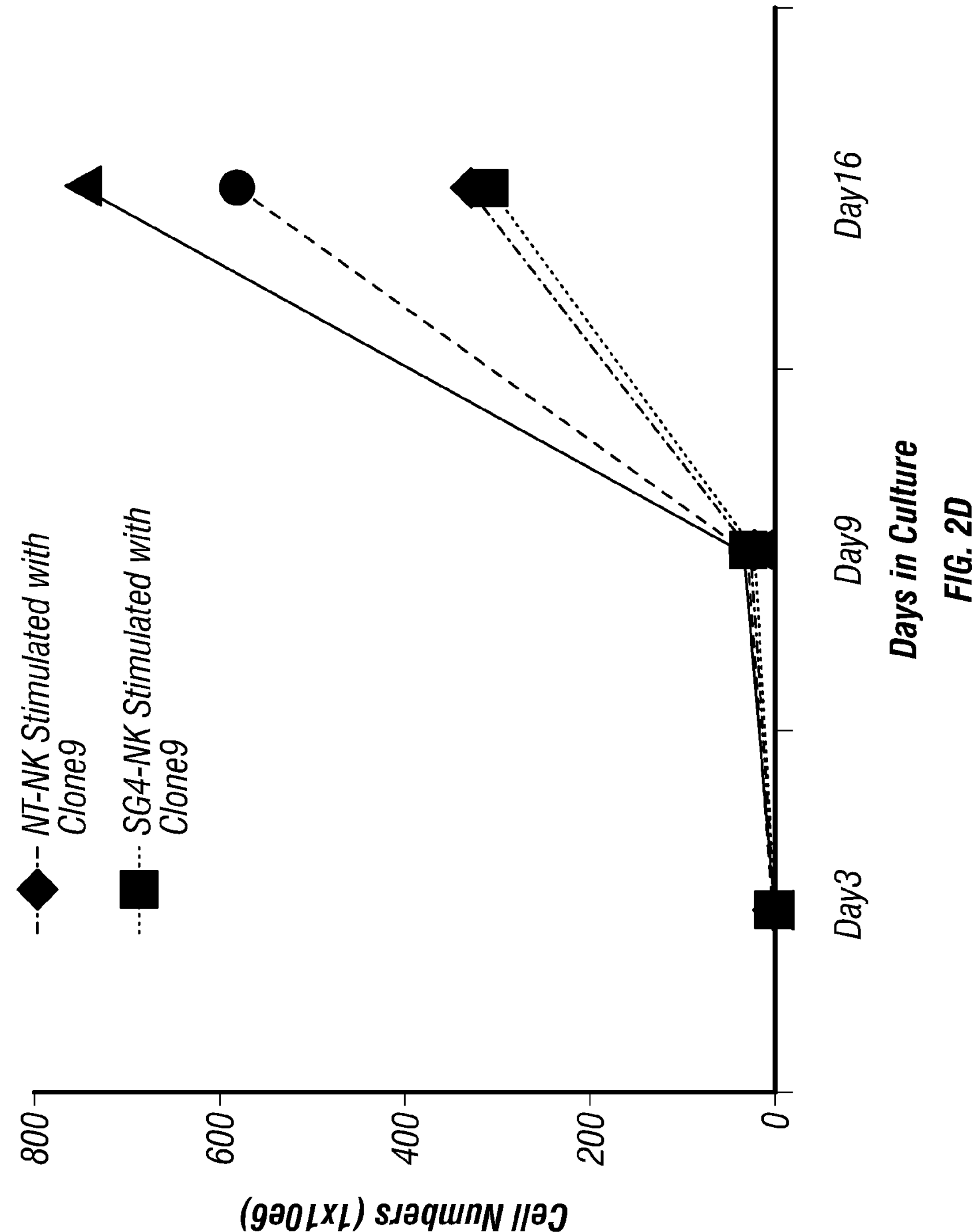

Numeric expansion of NK cells was performed with activation by clone 46, UAPC, or UAPC2. Proliferation and expansion of NK cells by APC co-culture showed that Clone 46 was superior in its ability to expand both non-transduced NK cells (NT-NK) and CAR-transduced (SG4-NK) as compared to the previously published clone 9 (FIG. 2B).

Figure 2E:
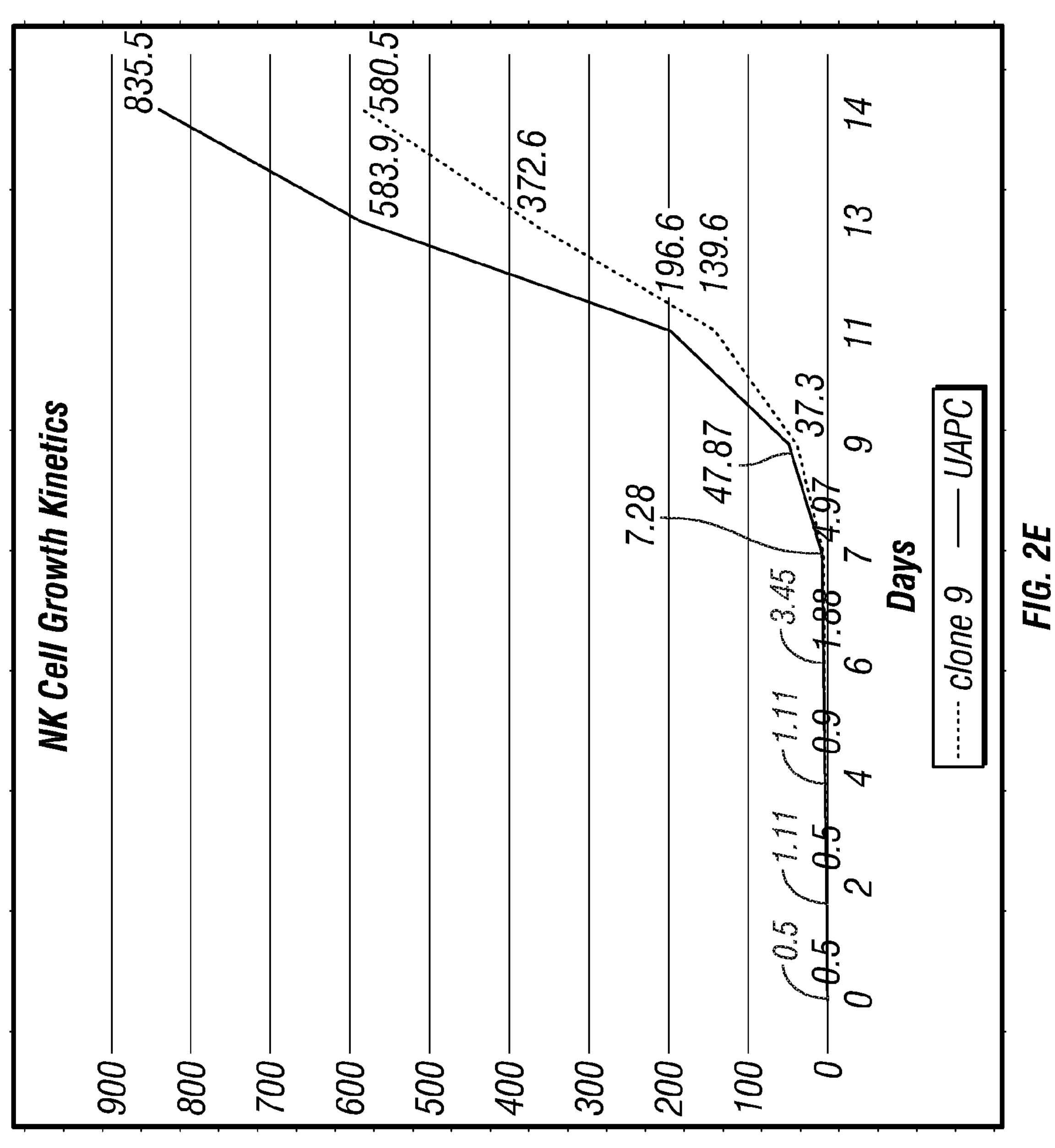

Expansion of NK cells by co-culture with UAPC was demonstrated to be superior in its ability to reduce NK cell doubling time to 31.38 hours compared to the previously published clone 9 (doubling time of 33 hours), yielding a proliferative advantage of 44% (1671-fold expansion for UAPC vs 1161-fold expansion for clone 9) over 2 weeks (FIG. 2E). The relationship between doubling time, fold expansion, and starting cell population is encapsulated by the following formula:

$$N_f = N_b e^{\frac{T}{T_D} ln2}$$

where $N_f$ is the final cell number, $N_b$ is the starting cell, e=2.71828 (mathematical constant also known as Euler's number), T is the time span of culture in hours, $T_D$ is the doubling time in hours. The doubling time affects the final cell number in an exponential manner, thus compounding the proliferative advantage over the designated cell culture period, enabling clinically relevant numbers of cells to be harvested in a compacted timeframe. Therefore, the present methods allow for the efficient production of NK cells by co-culture with the UAPCs.

The present platform technology takes advantage of specific combinatorial therapeutic pathways to provide practical methods for the manufacture of large numbers of clinical-grade highly functional and cytotoxic NK cells intended for cancer immunotherapy. The expanded cells are 100% NK cells, with no detectable T cells, avoiding unintended graft-versus-host side effects common in many immune cell preparations.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Czerkinsky et al., *J. Immunol. Methods* 1988; 110:29-36.
Fast et al., *Transfusion* 2004; 44:282-5.
He Y, et al. *Journal of immunology research.* 2014; 2014:7.
International Publication No. PCT/US95/01570
International Publication No. WO2000/06588
International Publication No. WO2005/035570
Olsson et al. *J. Clin. Invest.* 1990; 86:981-985.
Taitano et al., *The Journal of Immunology,* 196, 2016.
U.S. Pat. No. 5,939,281
U.S. Pat. No. 6,218,132
U.S. Pat. No. 6,264,951
U.S. Pat. No. 7,488,490
U.S. Patent Publication No. 2007/0078113

What is claimed is:

1. A K562 universal antigen presenting cell (UAPC) engineered to express (1) CD48, (2) membrane-bound interleukin-21 (mbIL-21), and (3) 41BB ligand (41BBL), wherein the K562 UAPC is essentially free of expression of endogenous HLA class I, II, or CD1d molecules, wherein the UAPC in co-culture with NK cells induces expansion of the NK cells.

2. The K562 UAPC of claim 1, wherein the K562 UAPC expresses CS1.

3. The K562 UAPC of claim 1, wherein the K562 UAPC expresses ICAM-1 (CD54) and LFA-3 (CD58).

4. The K562 UAPC of claim 1, wherein the K562 UAPC is a leukemia cell-derived UAPC.

5. The K562 UAPC of claim 1, wherein the K562 UAPC has been engineered by retroviral transduction.

6. The K562 UAPC of claim 5, wherein the retroviral transduction is further defined as transduction using a viral construct of SEQ ID NO: 1 and/or SEQ ID NO:2.

7. The K562 UAPC of claim 1, wherein the K562 UAPC is irradiated.

8. A method for expanding immune cells comprising culturing the immune cells in the presence of an effective amount of K562 UAPCs of claim 1, wherein the immune cells comprise NK cells.

9. The method of claim 8, wherein the immune cells and K562 UAPCs are cultured at a ratio of 3:1 to 1:3.

10. The method of claim 8, wherein the immune cells and K562 UAPCs are cultured at a ratio of 1:2.

11. The method of claim 8, wherein the expanding is in the presence of IL-2.

12. The method of claim 11, wherein the IL-2 is present at a concentration of 10-500 U/mL.

13. The method of claim 11, wherein the IL-2 is present at a concentration of 100-300 U/mL.

14. The method of claim 11, wherein the IL-2 is present at a concentration of 200 U/mL.

15. The method of claim 11, wherein the IL-2 is recombinant human IL-2.

16. The method of claim 11, wherein the IL-2 is replenished every 2-3 days.

17. The method of claim 8, wherein the K562 UAPCs are added at least a second time.

18. The method of claim 8, wherein the immune cells are derived from cord blood (CB), peripheral blood (PB), stem cells, or bone marrow.

19. The method of claim 8, wherein the stem cells are induced pluripotent stem cells.

20. The method of claim 8, wherein the immune cells are obtained from CB.

21. The method of claim 20, wherein the CB is pooled from 2 or more individual cord blood units.

22. The method of claim 20, wherein the CB is pooled from 3, 4, 5, 6, 7, or 8 individual cord blood units.

23. The method of claim 8, wherein the NK cells are CB mononuclear cells (CBMCs).

24. The method of claim 8, wherein NK cells are further defined as CD56+NK cells.

25. The method of claim 8, wherein the method is performed in serum-free media.

26. The method of claim 8, wherein the immune cells are engineered to express a chimeric antigen receptor (CAR).

27. The method of claim 26, wherein the CAR comprises a humanized antigen-binding domain.

28. The method of claim 26, wherein the CAR comprises a CD19, CD123, mesothelin, CD5, CD47, CLL-1, CD33, CD99, U5snRNP200, CD200, CS1, BAFF-R, ROR-1, or BCMA antigen-binding domain.

29. The method of claim 26, wherein the CAR comprises a CD19 or CD123 antigen-binding domain.

30. The method of claim 26, wherein the CAR-expressing immune cells co-express IL-15.

31. The method of claim 26, wherein the CAR-expressing immune cells co-express a suicide gene.

32. The method of claim 31, wherein the suicide gene is CD20, CD52, EGFRv3, or inducible caspase 9.

33. A population of expanded immune cells produced according to the methods of claim 8.

34. A pharmaceutical composition comprising the population of expanded immune cells of claim 33 and a pharmaceutically acceptable carrier.

35. A composition comprising an effective amount of the expanded immune cells of claim 33, for use in the treatment of a disease or disorder in a subject.

36. A method of treating a disease or disorder in a subject comprising administering a therapeutically effective amount of the expanded immune cells of claim 33 to the subject.

37. The method of claim 36, wherein the disease or disorder is cancer, inflammation, graft versus host disease, transplant rejection, an autoimmune disorder, an immunodeficiency disease, a B cell malignancy, or an infection.

38. The method of claim 37, wherein the cancer is a leukemia.

39. The method of claim 38, wherein the leukemia is an acute lymphoblastic leukemia (ALL), chronic lymphocytic leukemia (CLL), acute myelogenous leukemia (AML), or a chronic myelogenous leukemia (CML).

40. The method of claim 36, wherein the immune cells are allogeneic.

41. The method of claim 36, wherein the immune cells are autologous.

42. The method of claim 36, wherein the disorder is graft versus host disease (GVHD).

43. The method of claim 36, wherein the disorder is multiple sclerosis, inflammatory bowel disease, rheumatoid arthritis, type I diabetes, systemic lupus erythrematosus, contact hypersensitivity, asthma or Sjogren's syndrome.

44. The method of claim 36, wherein the subject is a human.

45. The method of claim 36, further comprising administering at least a second therapeutic agent.

46. The method of claim 45, wherein the at least a second therapeutic agent is a therapeutically effective amount of an anti-cancer agent, immunomodulatory agent, or an immunosuppressive agent.

47. The method of claim 46, wherein the anti-cancer agent is chemotherapy, radiotherapy, gene therapy, surgery, hormonal therapy, anti-angiogenic therapy or immunotherapy.

48. The method of claim 46, wherein the immunosuppressive agent is a calcineurin inhibitor, an mTOR inhibitor, an antibody, a chemotherapeutic agent irradiation, a chemokine, an interleukins or an inhibitor of a chemokine or an interleukin.

49. The method of claim 45, wherein immune cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion.

50. The method of claim 45, wherein the second therapeutic agent is an antibody.

51. The method of claim 50, wherein the antibody is a monoclonal, bispecific or trispecific antibody.

52. The method of claim 51, wherein the antibody is rituximab.

53. The K562 UAPC of claim 1, wherein the K562 UAPC in co-culture with NK cells can induce expansion of the NK cells at a rate of about or any value between any two of about 7 fold or more at day 7 of co-culture, about 40 fold or more at day 9 of co-culture, about 200 fold or more at day 11 of co-culture, about 400 fold or more at day 13 of co-culture, or about 600 fold or more at day 14 of co-culture.

54. The K562 UAPC of claim 1, wherein the K562 UAPC in co-culture with NK cells can induce expansion of the NK cells at a rate of about 800 fold or more at day 14 of co-culture.

55. The K562 UAPC of claim 1, wherein the rate of NK cell expansion is calculated using the formula $$N_f = N_b e^{\frac{T}{T_D} ln2},$$

wherein $N_f$ is the final cell number, $N_b$ is the starting cell, e=2.71828, T is the time span of culture in hours, and $T_D$ is the doubling time in hours.

56. The K562 UAPC of claim 1, wherein the K562 UAPC in co-culture with NK cells induces expansion of the NK cells at a rate greater than an antigen presenting cell not engineered to express CD48.

57. The K562 UAPC of claim 1, wherein the K562 UAPC in co-culture with NK cells induces expansion of the NK cells at a rate greater than an antigen presenting cell engineered to express mbIL-21 and 41BBL.

58. The K562 UAPC of claim 1, wherein the K562 UAPC in co-culture with NK cells induces expansion of the NK cells at a rate greater than an antigen presenting cell engineered to express mbIL-21 and 41BBL and not engineered to express CD48.

59. The K562 UAPC of claim 1, wherein the K562 UAPC in co-culture with NK cells can induce expansion of the NK cells at a rate of 10 fold to 1000 fold within 14-21 days of co-culture.

* * * * *

SEQUENCE LISTING

```
<160> NUMBER OF SEQ ID NOS: 2

<210> SEQ ID NO 1
<211> LENGTH: 8202
<212> TYPE: DNA
<213> ORGANISM: Artificial Sequence
<220> FEATURE:
<223> OTHER INFORMATION: CS1 Construct

<400> SEQUENCE: 1

aatgaaagac cccacctgta ggtttggcaa gctagcttaa gtaacgccat tttgcaaggc     60

atggaaaaat acataactga gaatagaaaa gttcagatca aggtcaggaa cagatggaac    120

agctgaatat gggccaaaca ggatatctgt ggtaagcagt tcctgccccg gctcagggcc    180

aagaacagat ggaacagctg aatatgggcc aaacaggata tctgtggtaa gcagttcctg    240

ccccggctca gggccaagaa cagatggtcc ccagatgcgg tccagccctc agcagtttct    300

agagaaccat cagatgtttc cagggtgccc caaggacctg aaatgaccct gtgccttatt    360

tgaactaacc aatcagttcg cttctcgctt ctgttcgcgc gcttatgctc cccgagctca    420

ataaaagagc ccacaacccc tcactcgggg cgccagtcct ccgattgact gagtcgcccg    480

ggtacccgtg tatccaataa accctcttgc agttgcatcc gacttgtggt ctcgctgttc    540

cttgggaggg tctcctctga gtgattgact acccgtcagc gggggtcttt catttggggg    600

ctcgtccggg atcgggagac ccctgcccag ggaccaccga cccaccaccg ggaggtaagc    660

tggccagcaa cttatctgtg tctgtccgat tgtctagtgt ctatgcgact gattttatgc    720

gcctgcgtcg gtactagtta gctaactagc tctgtatctg gcggacccgt gggctggaac    780
```

-continued

```
tgacgagttc ggaacacccg gccgcaaccc tgggagacgt cccagggact tcgggggccg     840
gctttttgtg gcccgacctg agtcctaaaa tcccgatcgt ttaggactct ttggtgcacc     900
ccccttaggc aggagggata tgtggttctg gtaggagacg agaacctaaa acagttcccg     960
cctccgtctg aatttttgct ttcggtttgg gaccgaagcc gcgccgcgcg tcttgtctgc    1020
tgcagcatcg ttctgtgttg tcgctctgtc tgactgtgtt tctgtatttg tctgaaaata    1080
tgggcccggg ctagcctgtt accactccct gctaagtttg accttaggtc actggaaaga    1140
tgtcgagcgg atcgctcaca accagtcggt agatgtcagc agaagagacg ttgggttacc    1200
ttctgctctg cagaatggcc aacctttaac gtcggatggc cgcgaggcac ggcaccttta    1260
accgagacct catcacccag gttaagatca aggtcttttc acctggcccg catggacacc    1320
cagaccaggt ggggtacatc gtgacctggg aagccttggc ttttgacccc cctccctggg    1380
tcaagccctt tgtacaccct aagcctccgc ctcctcttcc tccatccgcc ccgtctctcc    1440
cccttggcaa cctcctcgtt cgaccccgcc tcgatcctcc ctttatccag ccctcactcc    1500
ttctctaggc gcccccatat ggccatatga gatcttatat ggggcacccc cgccccttgt    1560
aaacttccct gaccctgaca tgacaagagt tactaacagc ccctctctcc aagctcactt    1620
acaggctctc tacttagtcc agcacggcaa gtctggagac ctctggcggc agcctaccaa    1680
gaacaactgg accgaccggt ggtacctcac ccttgcaccg agtcggcgac acagtgtggg    1740
tccgccgaca ccagactaag aacctagaac ctcgctggaa aggcgacctt acacagtcct    1800
gctgaccacc cccaccgccc tcaaagtaga cggcatcgca gcttggatac acgccgccca    1860
cgtgaaggct gccgaccccg ggggtggacc atcctctaga ctgccatgct cgaggccggc    1920
agccccacct gcctgaccct gatctacatc ctgtggcagc tgaccggcag cgccgccagc    1980
ggccccgtga aggagctggt gggcagcgtg ggcggcgccg tgaccttccc cctgaagagc    2040
aaggtgaagc aggtggacag catcgtgtgg accttcaaca ccacccccct ggtgaccatc    2100
cagcccgagg gcggcaccat catcgtgacc cagaacagaa acagagagag agtggacttc    2160
cccgacggcg gctacagcct gaagctgagc aagctgaaga agaacgacag cggcatctac    2220
tacgtgggca tctacagcag cagcctgcag cagcccagca cccaggagta cgtgctgcac    2280
gtgtacgagc acctgagcaa gcccaaggtg accatgggcc tgcagagcaa caagaacggc    2340
acctgcgtga ccaacctgac ctgctgcatg gagcacggcg aggaggacgt gatctacacc    2400
tggaaggccc tgggccaggc cgccaacgag agccacaacg gcagcatcct gcccatcagc    2460
tggagatggg gcgagagcga catgaccttc atctgcgtgg ccagaaaccc cgtgagcaga    2520
aacttcagca gccccatcct ggccagaaag ctgtgcgagg gcgccgccga cgaccccgac    2580
agcagcatgg tgctgctgtg cctgctgctg gtgcccctgc tgctgagcct gttcgtgctg    2640
ggcctgttcc tgtggttcct gaagagagag agacaggagg agtacatcga ggagaagaag    2700
agagtggaca tctgcagaga gacccccaac atctgccccc acagcggcga gaacaccgag    2760
tacgacacca tcccccacac caacagaacc atcctgaagg aggaccccgc caacaccgtg    2820
tacagcaccg tggagatccc caagaagatg gagaaccccc acagcctgct gaccatgccc    2880
gacaccccca gactgttcgc ctacgagaac gtgatcggca gcacctccgg cagcggcgcg    2940
cctggcagcg gcgagggcag caccaagggc atggtgagca agggcgagga gctgttcacc    3000
ggggtggtgc ccatcctggt cgagctggac ggcgacgtaa acggccacaa gttcagcgtg    3060
tccggcgagg gcgagggcga tgccacctac ggcaagctga ccctgaagtt catctgcacc    3120
accggcaagc tgcccgtgcc ctggcccacc ctcgtgacca ccctgaccta cggcgtgcag    3180
```

```
tgcttcagcc gctaccccga ccacatgaag cagcacgact tcttcaagtc cgccatgccc   3240
gaaggctacg tccaggagcg caccatcttc ttcaaggacg acggcaacta caagacccgc   3300
gccgaggtga agttcgaggg cgacaccctg gtgaaccgca tcgagctgaa gggcatcgac   3360
ttcaaggagg acggcaacat cctggggcac aagctggagt acaactacaa cagccacaac   3420
gtctatatca tggccgacaa gcagaagaac ggcatcaagg tgaacttcaa gatccgccac   3480
aacatcgagg acggcagcgt gcagctcgcc gaccactacc agcagaacac ccccatcggc   3540
gacggccccg tgctgctgcc cgacaaccac tacctgagca cccagtccgc cctgagcaaa   3600
gaccccaacg agaagcgcga tcacatggtc ctgctggagt tcgtgaccgc cgccgggatc   3660
actctcggca tggacgagct gtacaagtga cgcgtcatca tcgatccgga ttagtccaat   3720
ttgttaaaga caggatatca gtggtccagg ctctagtttt gactcaacaa tatcaccagc   3780
tgaagcctat agagtacgag ccatagataa aataaaagat tttatttagt ctccagaaaa   3840
aggggggaat gaaagacccc acctgtaggt ttggcaagct agcttaagta acgccatttt   3900
gcaaggcatg gaaaaataca taactgagaa tagagaagtt cagatcaagg tcaggaacag   3960
atggaacagc tgaatatggg ccaaacagga tatctgtggt aagcagttcc tgccccggct   4020
cagggccaag aacagatgga acagctgaat atgggccaaa caggatatct gtggtaagca   4080
gttcctgccc cggctcaggg ccaagaacag atggtcccca gatgcggtcc agccctcagc   4140
agtttctaga gaaccatcag atgtttccag ggtgccccaa ggacctgaaa tgaccctgtg   4200
ccttatttga actaaccaat cagttcgctt ctcgcttctg ttcgcgcgct tctgctcccc   4260
gagctcaata aaagagccca caacccctca ctcggggcgc cagtcctccg attgactgag   4320
tcgcccgggt acccgtgtat ccaataaacc ctcttgcagt tgcatccgac ttgtggtctc   4380
gctgttcctt gggagggtct cctctgagtg attgactacc cgtcagcggg ggtctttcac   4440
acatgcagca tgtatcaaaa ttaatttggt ttttttttctt aagtatttac attaaatggc   4500
catagtactt aaagttacat tggcttcctt gaaataaaca tggagtattc agaatgtgtc   4560
ataaatattt ctaattttaa gatagtatct ccattggctt tctacttttt cttttatttt   4620
tttttgtcct ctgtcttcca tttgttgttg ttgttgtttg tttgtttgtt tgttggttgg   4680
ttggttaagc ttttttttta aagatcctac actatagttc aagctagact attagctact   4740
ctgtaaccca gggtgagccc ttgaagtcat gggtagcctg ctgttttagc cttcccacat   4800
ctaagattac aggtatgagc tatcgcattt ttggtatatt gattgattga ttgattgatg   4860
tgtgtgtgtg tgattgtgtt tgtgtgtgtg acgctgtgaa aatgtgtgta tgggtgtgtg   4920
tgaatgtgtg tatgtatgtg tgtgtgtgag tgtgtgtgtg tgtgtgtgca tgtgtgtgtg   4980
tgtgactgtg tctatgtgta tgactgtgtg tgtgtgtgtg tgtgtggctg tgtgtgtgtg   5040
tgtgtgtgtg tgttgtgaaa aaatattcta tggtagtgag agccaacgct ccgggcctca   5100
ggtgtcaggt tggtttttga gacagagtct ttcacttagc ttggaattca ctggccgtcg   5160
ttgcttacaa cgtcgtgact gggaaaaccc tggcgttacc caacttaatc gccttgcagc   5220
acatccccct gcttcgccag ctggcgtaat agcgaagagg cccgcaccga tcgcccttcc   5280
caacagttgc gcagcctggc aatggcgaat ggcgcctgat gcggtatttt ctccttacgc   5340
atctgtgcgg tatttcacac cgcatagctg gtgcactctc agtacaatct gctctgatgc   5400
cgcatagtta agccagcccc gacacccgcc aacagccccg ctgacgcgcc ctgacgggct   5460
tgtctgctcc cggcatccgc ttacagacaa gctgtgaccg tcgctccggg agctgcatgt   5520
```

-continued

```
gtcagaggtt ttcaccgtca tcaccgaaac gcgcgagacg aaagggcctc gcgtgatacg   5580
cctattttta taggttaatg tcatgataat aatggtttct tagacgtcag gtggcacttt   5640
tcggggaaat gtgcgcggaa cccctatttg tttatttttc taaatacatt caaatatgta   5700
tccgctcatg agacaataac cctgataaat gcttcaataa tattgaaaaa ggaagagtat   5760
gagtattcaa catttccgtg tcgcccttat tccctttttt gcggcatttt gccttcctgt   5820
ttttgctcac ccagaaacgc tggtgaaagt aaaagatgct gaagatcagt tgggtgcacg   5880
agtgggttac atcgaactgg atctcaacag cggtaagatc cttgagagtt ttcgccccga   5940
agaacgtttt ccaatgatga gcacttttaa agttctgcta tgtggcgcgg tattatcccg   6000
tattgacgcc gggcaagagc aactcggtcg ccgcatacac tattctcaga atgacttggt   6060
tgagtactca ccagtcacag aaaagcatct tacggatggc atgacagtaa gagaattatg   6120
cagtgctgcc ataaccatga gtgataacac tgcggccaac ttacttctga caacgatcgg   6180
aggaccgaag gagctaaccg cttttttgca caacatgggg gatcatgtaa ctcgccttga   6240
tcgttgggaa ccggagctga atgaagccat accaaacgac gagcgtgaca ccacgatgcc   6300
tgtagcaatg gcaacaacgt tgcgcaaact attaactggc gaactactta ctctagcttc   6360
ccggcaacaa ttaatagact ggatggaggc ggataaagtt gcaggaccac ttctgcgctc   6420
ggcccttccg gctggctggt ttattgctga taaatctgga gccggtgagc gtgggtctcg   6480
cggtatcatt gcagcactgg ggccagatgg taagccctcc cgtatcgtag ttatctacac   6540
gacggggagt caggcaacta tggatgaacg aaatagacag atcgctgaga taggtgcctc   6600
actgattaag cattggtaac tgtcagacca agtttactca tatatacttt agattgattt   6660
aaaacttcat ttttaattta aaaggatcta ggtgaagatc ctttttgata atctcatgac   6720
caaaatccct taacgtgagt tttcgttcca ctgagcgtca gaccccgtag aaaagatcaa   6780
aggatcttct tgagatcctt tttttctgcg cgtaatctgc tgcttgcaaa caaaaaaacc   6840
accgctacca gcggtggttt gtttgccgga tcaagagcta ccaactcttt ttccgaaggt   6900
aactggcttc agcagagcgc agataccaaa tactgttctt ctagtgtagc cgtagttagg   6960
ccaccacttc aagaactctg tagcaccgcc tacatacctc gctctgctaa tcctgttacc   7020
agtggctgct gccagtggcg ataagtcgtg tcttaccggg ttggactcaa gacgatagtt   7080
accggataag gcgcagcggt cgggctgaac ggggggttcg tgcacacagc ccagcttgga   7140
gcgaacgacc tacaccgaac tgagatacct acagcgtgag ctatgagaaa gcgccacgct   7200
tcccgaaggg agaaaggcgg acaggtatcc ggtaagcggc agggtcggaa caggagagcg   7260
cacgagggag cttccagggg gaaacgcctg gtatctttat agtcctgtcg ggtttcgcca   7320
cctctgactt gagcgtcgat ttttgtgatg ctcgtcaggg gggcggagcc tatggaaaaa   7380
cgccagcaac gcggcctttt tacggttcct ggccttttgc tggccttttg ctcacatgtt   7440
ctttcctgcg ttatcccctg attctgtgga taaccgtatt accgcctttg agtgagctga   7500
taccgctcgc cgcagccgaa cgaccgagcg cagcgagtca gtgagcgagg aagcggaaga   7560
gcgcccaata cgcaaaccgc ctctccccgc gcgttggccg attcattaat gcagctggca   7620
cgacaggttt cccgactgga aagcgggcag tgagcgcaac gcaattaatg tgagttagct   7680
cactgccatt aggcacccca ggctttacac tttatgcttc cggctcgtat gttgtgtgga   7740
attgtgagcg gagctaacaa tttcacacag gaaacagcta tgaccatgat tacgccaagc   7800
tttgctctta ggagtttcct gcaatacatc ccaaactcaa atatataaag catttgactt   7860
gttctatgcc ctagggggcg gggggaaggc ctaagccagc ttttttttaac atttaaaatg   7920
```

ttaattccat tttaaatgca cagatgtttt tatttcgcat aagggtttca atgtgcatga 7980
atgctgcaat attcctgtta ccaaagctag tataaataaa aatagataaa cgtggaaatt 8040
acttagagtt tctgtcatta acgtttcctt cctcagttga caacataaat gcgcgctgct 8100
gagcaagcca gtttgcatct gtcaggatca atttcccatt atgccagtca tattaattgc 8160
actagtcaat tagttgattt ttatttttga catatacatg tg 8202

<210> SEQ ID NO 2
<211> LENGTH: 7935
<212> TYPE: DNA
<213> ORGANISM: Artificial Sequence
<220> FEATURE:
<223> OTHER INFORMATION: CD48 Construct

<400> SEQUENCE: 2
aatgaaagac cccacctgta ggtttggcaa gctagcttaa gtaacgccat tttgcaaggc 60
atggaaaaat acataactga gaatagaaaa gttcagatca aggtcaggaa cagatggaac 120
agctgaatat gggccaaaca ggatatctgt ggtaagcagt tcctgccccg gctcagggcc 180
aagaacagat ggaacagctg aatatgggcc aaacaggata tctgtggtaa gcagttcctg 240
ccccggctca gggccaagaa cagatggtcc ccagatgcgg tccagccctc agcagtttct 300
agagaaccat cagatgtttc cagggtgccc caaggacctg aaatgaccct gtgccttatt 360
tgaactaacc aatcagttcg cttctcgctt ctgttcgcgc gcttatgctc cccgagctca 420
ataaaagagc ccacaacccc tcactcgggg cgccagtcct ccgattgact gagtcgcccg 480
ggtacccgtg tatccaataa accctcttgc agttgcatcc gacttgtggt ctcgctgttc 540
cttgggaggg tctcctctga gtgattgact acccgtcagc gggggtcttt catttggggg 600
ctcgtccggg atcgggagac ccctgcccag ggaccaccga cccaccaccg ggaggtaagc 660
tggccagcaa cttatctgtg tctgtccgat tgtctagtgt ctatcgactg attttatgcg 720
cctgcgtcgg tactagttag ctaactagct ctgtatctgg cggacccgtg gctggaactg 780
acgagttcgg aacacccggc cgcaaccctg ggagacgtcc cagggacttc gggggccgct 840
ttttgtggcc cgacctgagt cctaaaatcc cgatcgttta ggactctttg gtgcaccccc 900
cttagcagga gggatatgtg gttctggtag gagacgagaa cctaaaacag ttcccgcctc 960
cgtctgaatt tttgctttcg gtttgggacc gaagccgcgc cgcgcgtctt gtctgctgca 1020
gcatcgttct gtgttgtcct ctgtctgact gtgtttctgt atttgtctga aaatatgggc 1080
ccgggctagc ctgttaccac tccctctaag tttgacctta ggtcactgga aagatgtcga 1140
gcggatcgct cacaaccagt cggtagatgt cacagaagag acgttgggtt accttctgct 1200
ctgcagaatg gccaaccttt aacgtcggat ggccgcgagc acggcacctt taaccgagac 1260
ctcatcaccc aggttaagat caaggtcttt tcacctggcc cgcatggaca cccagaccag 1320
gtggggtaca tcgtgacctg ggaagccttg gcttttgacc cccctccctg ggtcaagccc 1380
tttgtacacc ctaagcctcc gcctcctctt cctccatccg ccccgtctct ccccccttgca 1440 acctcctcgt tcgaccccgc ctcgatcctc cctttatcca gccctcactc cttctctagg 1500
cgcccccata tggccatatg agatcttata tggggcaccc ccgcccccttg taaacttccc 1560 tgaccctgac atgacaagag ttactaacag cccctctctc caagctcact tacaggctct 1620
ctacttagtc cagcacgcaa gtctggagac ctctggcggc agcctaccaa gaacaactgg 1680
accgaccggt ggtacctcac ccttcaccga gtcggcgaca cagtgtgggt ccgccgacac 1740

-continued

```
cagactaaga acctagaacc tcgctggaaa gcgaccttac acagtcctgc tgaccacccc   1800
caccgccctc aaagtagacg gcatcgcagc ttggatacac gccgcccacg tgaaggctgc   1860
cgaccccggg ggtggaccat cctctagact gccatgctcg aggtgggtga ggatagcgtg   1920
ctgatcaccg agaacatgca catgaaactg tacatggagg gcaccgtgaa cgaccaccac   1980
ttcaagtgca catccgaggg cgaaggcaag ccctacgagg gcacccagac catgaagatc   2040
aaggtggtcg agggcggccc tctcccctte gccttcgaca tcctggctac cagcttcatg   2100
tacggcagca aaacctttat caaccacacc cagggcatcc ccgacttctt taagcagtcc   2160
ttccctgagg gcttcacatg ggagaggatc accacatacg aagacggggg cgtgctgacc   2220
gctacccagg acaccagcct ccagaacggc tgcctcatct acaacgtcaa gatcaacggg   2280
gtgaacttcc catccaacgg ccctgtgatg cagaagaaaa cactcggctg ggaggccagc   2340
accgagatgc tgtaccccgc tgacagcggc ctgagaggcc atgcccagat ggccctgaag   2400
ctcgtgggcg gggctacct gcactgctcc ctcaagacca catacagatc caagaaaccc    2460
gctaagaacc tcaagatgcc cggcttctac ttcgtggacc ggagactgga aagaatcaag   2520
gaggccgaca aagagaccta cgtcgagcag cacgagatgg ctgtggccag atactgcgac   2580
ctgcctagca aactggggca cagcggcagc acctccggca gcggcgcgcc tggcagcggc   2640
gagggcagca ccaagggcga gggcaggga agtcttctaa catgcgggga cgtggaggaa    2700
aatcccgggc ccatgtgcag cagaggctgg gacagctgcc tggccctgga gctgctgctg   2760
ctgcccctga gcctgctggt gaccagcatc cagggccacc tggtgcacat gaccgtggtg   2820
agcggcagca acgtgaccct gaacatcagc gagagcctgc ccgagaacta caagcagctg   2880
acctggttct acaccttcga ccagaagatc gtggagtggg acagcagaaa gagcaagtac   2940
ttcgagagca agttcaaggg cagagtgaga ctggaccccc agagcggcgc cctgtacatc   3000
agcaaggtgc agaaggagga caacagcacc tacatcatga gagtgctgaa gaagaccggc   3060
aacgagcagg agtggaagat caagctgcag gtgctggacc ccgtgcccaa gcccgtgatc   3120
aagatcgaga agatcgagga catggacgac aactgctacc tgaagctgag ctgcgtgatc   3180
cccggcgaga gcgtgaacta cacctggtac ggcgacaaga gacccttccc caaggagctg   3240
cagaacagcg tgctggagac caccctgatg ccccacaact acagcagatg ctacacctgc   3300
caggtgagca acagcgtgag cagcaagaac ggcaccgtgt gcctgagccc ccccctgcacc  3360
ctggccagaa gcttcggcgt ggagtggatc gccagctggc tggtggtgac cgtgcccacc   3420
atcctgggcc tgctgctgac ctgacgcgtc atcatcgatc cggattagtc caatttgtta   3480
aagacaggat atcagtggtc caggctctag ttttgactca acaatatcac cagctgaagc   3540
ctatagagta cgagccatag ataaaataaa agattttatt tagtctccag aaaaaggggg   3600
gaatgaaaga ccccacctgt aggtttggca agctagctta agtaacgcca ttttgcaagg   3660
catggaaaaa tacataactg agaatagaga agttcagatc aaggtcagga acagatggaa   3720
cagctgaata tgggccaaac aggatatctg tggtaagcag ttcctgcccc ggctcagggc   3780
caagaacaga tggaacagct gaatatgggc caaacaggat atctgtggta agcagttcct   3840
gccccggctc agggccaaga acagatggtc cccagatgcg gtccagccct cagcagtttc   3900
tagagaacca tcagatgttt ccagggtgcc ccaaggacct gaaatgaccc tgtgccttat   3960
ttgaactaac caatcagttc gcttctcgct tctgttcgcg cgcttctgct ccccgagctc   4020
aataaaagag cccacaaccc ctcactcggg gcgccagtcc tccgattgac tgagtcgccc   4080
gggtacccgt gtatccaata aaccctcttg cagttgcatc cgacttgtgg tctcgctgtt   4140
```

-continued

```
ccttgggagg gtctcctctg agtgattgac tacccgtcag cgggggtctt tcacacatgc   4200
agcatgtatc aaaattaatt tggttttttt tcttaagtat ttacattaaa tggccatagt   4260
acttaaagtt acattggctt ccttgaaata aacatggagt attcagaatg tgtcataaat   4320
atttctaatt ttaagatagt atctccattg gctttctact tttctttta ttttttttg   4380
tcctctgtct tccatttgtt gttgttgttg ttctgtttgt ttgtttgttg gttggttggt   4440
taattttttt ttaaagatcc tacactatag ttcaagctag actattagct actctgtaac   4500
ccagggtgac cttgaagtca tgggtagcct gctgttttag ccttccccac atctaagatt   4560
acaggtatga gctatcattt ttggtatatt gattgattga ttgattgatg tgtgtgtgtg   4620
tgattgtgtt tgtgtgtgtg actgtgaaaa tgtgtgtatg ggtgtgtgtg aatgtgtgct   4680
atgtatgtgt gtgtgtgagt gtgtgtgtgt gtgtgtgcat gtgtgtgtgt gtgactgtgt   4740
ctatgctgta tgactgtgtg tgtgtgtgtg tgtgtgtgtg tgtgtgtgtg tgtgtgtgtg   4800
ttgtgaaaaa atcattctat ggtagtgaga gccaacgctc cggctcaggt gtcaggttgg   4860
tttttgagac agagtctttc cacttagctt ggaattcact ggccgtcgtt ttacaacgtc   4920
gtgactggga aaaccctggc gttacccaac ttaatcgcct tgcagcacat ccccctttcg   4980
ccagctggcg taatagcgaa gaggcccgca cccgatcgcc cttcccaaca gttgcgcagc   5040
ctgaatggcg aatggcgcct gatgcggtat tttctccttc acgcatctgt gcggtatttc   5100
acaccgcata tggtgcactc tcagtacaat ctgctctgat gccgcatagt taagccagcc   5160
ccgacacccg ccaacacccg ctgacgcgcc ctgacgggct tgtctgctcc cgcgcatccg   5220
cttacagaca agctgtgacc gtctccggga gctgcatgtg tcagaggttt tcaccgtcat   5280
caccgaaacg cgcgagacga aagggcctcg tgatacgcct atttttatag gttaatgtca   5340
tgatacataa tggtttctta gacgtcaggt ggcacttttc ggggaaatgt gcgcggaacc   5400
cctatttgtt tatttttcta aatacattca aatatgtatc cgctcatgag acaataaccc   5460
tgataaatgc ttcaataata ttgaaaaagg aagagtatga gtattcaaca tttccgtgtc   5520
gcccttattc cctttttgc ggcattttgc cttcctgttt ttgctcaccc agaaacgctg   5580
gtgaaagtaa aagatgctga agatcagttg ggtgcacgag tgggttacat cgaactggat   5640
ctcaacagcg gtaagatcct tgagagtttt cgccccgaag aacgttttcc aatgatgagc   5700
acttttaaag ttctgctatg tggcgcggta ttatcccgta ttgacgccgg gcaagagcaa   5760
ctcggtcgcc gcatacacta ttctcagaat gacttggttg agtactcacc agtcacagaa   5820
aagcatctta cggatggcat gacagtaaga gaattatgca gtgctgccat aaccatgagt   5880
gataacactg cggccaactt acttctgaca acgatcggag gaccgaagga gctaaccgct   5940
tttttgcaca acatggggga tcatgtaact cgccttgatc gttgggaacc ggagctgaat   6000
gaagccatac caaacgacga gcgtgacacc acgatgcctg tagcaatggc aacaacgttg   6060
cgcaaactat taactggcga actacttact ctagcttccc ggcaacaatt aatagactgg   6120
atggaggcgg ataaagttgc aggaccactt ctgcgctcgg cccttccggc tggctggttt   6180
attgctgata aatctggagc cggtgagcgt gggtctcgcg gtatcattgc agcactgggg   6240
ccagatggta agccctcccg tatcgtagtt atctacacga cggggagtca ggcaactatg   6300
gatgaacgaa atagacagat cgctgagata ggtgcctcac tgattaagca ttggtaactg   6360
tcagaccaag tttactcata tatactttag attgatttaa aacttcattt ttaatttaaa   6420
aggatctagg tgaagatcct ttttgataat ctcatgacca aaatccctta acgtgagttt   6480
```

-continued

```
tcgttccact gagcgtcaga ccccgtagaa aagatcaaag gatcttcttg agatcctttt   6540
tttctgcgcg taatctgctg cttgcaaaca aaaaaaccac cgctaccagc ggtggtttgt   6600
ttgccggatc aagagctacc aactcttttt ccgaaggtaa ctggcttcag cagagcgcag   6660
ataccaaata ctgttcttct agtgtagccg tagttaggcc accacttcaa gaactctgta   6720
gcaccgccta catacctcgc tctgctaatc ctgttaccag tggctgctgc cagtggcgat   6780
aagtcgtgtc ttaccgggtt ggactcaaga cgatagttac cggataaggc gcagcggtcg   6840
ggctgaacgg ggggttcgtg cacacagccc agcttggagc gaacgaccta caccgaactg   6900
agatacctac agcgtgagct atgagaaagc gccacgcttc ccgaagggag aaaggcggac   6960
aggtatccgg taagcggcag ggtcggaaca ggagagcgca cgagggagct tccaggggga   7020
aacgcctggt atctttatag tcctgtcggg tttcgccacc tctgacttga gcgtcgattt   7080
ttgtgatgct cgtcaggggg gcggagccta tggaaaaacg ccagcaacgc ggccttttta   7140
cggttcctgg ccttttgctg gccttttgct cacatgttct ttcctgcgtt atcccctga    7200
ttctgtggat aaccgtatta ccgcctttga gtgagctgat accgctcgcc gcagccgaac   7260
gcaccgagcg cagcgagtca gtgagcgagg aagcggaaga gcgcccaata cgcaaaccgc   7320
ctctccccg cgcgttggcc gattcattaa tgcagctggc acgacaggtt tcccgactgg    7380
aaagcgggca gtgagcgcaa cgcaattaat gtgagttagc tcactcatta ggcaccccag   7440
gctttacact ttatgcttcc gcgctcgtat gttgtgtgga attgtgagcg gataacaatt   7500
tcacacagga aacagctatg accatgatct acgccaagct ttgctcttag gagtttccta   7560
atacatccca aactcaaata tataaagcat ttgacttgtt ctatgcccta gggggcgggg   7620
ggaagctaag ccagcttttt ttaacattta aaatgttaat tcccatttta aatgcacaga   7680
tgtttttatt tcataagggt ttcaatgtgc atgaatgctg caatattccc tgttaccaaa   7740
gctagtataa ataaaaatag ataaacgtgg aaattactta gagtttctgt cattacacgt   7800
ttccttcctc agttgacaac ataaatgcgc tgctgagcaa gccagtttgc atctgtcagg   7860
atccaatttc ccattatgcc agtcatatta attactagtc aattagttga tttttatttt   7920
tgacatatac atgtg                                                    7935
```